United States Patent
Coy et al.

(10) Patent No.: US 9,358,272 B2
(45) Date of Patent: Jun. 7, 2016

(54) MULTICOMPONENT COMPOSITIONS AND THEIR USES

(75) Inventors: David H. Coy, Metairie, LA (US); Lichun Sun, Matairie, LA (US)

(73) Assignee: THE ADMINISTRATORS OF THE TULANE EDUCATIONAL FUND, New Orleans, LA (US)

( * ) Notice: Subject to any disclaimer, the term of this patent is extended or adjusted under 35 U.S.C. 154(b) by 16 days.

(21) Appl. No.: 13/985,051

(22) PCT Filed: Feb. 16, 2012

(86) PCT No.: PCT/US2012/025479
§ 371 (c)(1),
(2), (4) Date: Aug. 20, 2013

(87) PCT Pub. No.: WO2012/112792
PCT Pub. Date: Aug. 23, 2012

(65) Prior Publication Data
US 2014/0045752 A1    Feb. 13, 2014

Related U.S. Application Data

(60) Provisional application No. 61/558,227, filed on Nov. 10, 2011, provisional application No. 61/463,482, filed on Feb. 17, 2011.

(51) Int. Cl.
*A61K 45/06* (2006.01)
*A61K 31/19* (2006.01)
*A61K 38/31* (2006.01)

(52) U.S. Cl.
CPC ............... *A61K 38/31* (2013.01); *A61K 31/19* (2013.01); *A61K 45/06* (2013.01)

(58) Field of Classification Search
None
See application file for complete search history.

(56) References Cited

U.S. PATENT DOCUMENTS

| | | |
|---|---|---|
| 7,326,685 B2 | 2/2008 | Coy et al. |
| 7,771,727 B2 | 8/2010 | Fuselier et al. |
| 7,919,092 B2 | 4/2011 | Lewicki et al. |

FOREIGN PATENT DOCUMENTS

| | | | |
|---|---|---|---|
| CN | 1964714 A | | 5/2007 |
| CN | 101325955 A | | 12/2008 |
| WO | 0210215 A1 | | 2/2002 |
| WO | WO 03/028527 | * | 4/2003 |
| WO | 03042246 A2 | | 5/2003 |
| WO | 2005/023179 A2 | | 3/2005 |
| WO | 2007/056135 A1 | | 5/2007 |
| WO | 2012112792 A2 | | 8/2012 |

OTHER PUBLICATIONS

Platta et al., J. Surg. Res., 2008, 148(1), 31.*
Macaulay et al., Br. J. Cancer, 1991, 64(3), 451.*
Sun et al., Clinical Medicine: Oncology, 2008, 491-499.*
Patel, YC., "Somatostatin and its receptor family" Front Neuroendocrinol (1999) vol. 20, pp. 157-198.
Pereira, David Valter et al., "Effects of an Antagonist of the Gastrin-Releasing Peptide Receptor in an Animal Model of Uveitis" Investigative Ophthalmology & Visual Science (2009) vol. 50, No. 11, pp. 5300-5303.
Perez-Plasencia, C. et al., "Second hit in cervical carcinogenesis process: involvement of wnt/beta catenin pathway" Int Arch Med (2008) vol. 1, pp. 10-17.
Proweller, A. et al., "Impaired notch signaling promotes de novo squamous cell carcinoma formation" Cancer Res (2006) vol. 66, No. 15, pp. 7438-7444.
Pyronnet, S. et al., "Antitumor effects of somatostatin" Mol Cell Endocrinol (2008) vol. 286, pp. 230-237.
Rajeswaran, W.G. et al., "Exploration of the DTrp-NMeLys Motif in the Search for Potent Somatostatin Antagonists" Bioorganic & Medicinal Chemistry (2002) vol. 10, pp. 2023-2029.
Ramdass, B. et al., "Coexpression of Notch1 and NF-κB signaling pathway components in human cervical cancer progression" Gynecologic Oncol (2007) vol. 104, pp. 352-361.
Reubi, JC et al., "Vasoactive intestinal peptide/pituitary adenylate cyclase-activating peptide receptor subtypes in human tumors and their tissues of origin" Cancer Res (2000) vol. 60, pp. 3105-3112.
Reubi, JC., "Peptide receptors as molecular targets for cancer diagnosis and therapy" Endocr Rev (2003) vol. 24, No. 4, pp. 389-427.
Reubi, JC. et al., "Somatostatin receptors and their subtypes in human tumors and in peritumoral vessels" Metabolism (1996) vol. 45, No. 8, Suppl 1, pp. 39-41.
Rincón-Arano, H. et al., "Rosales R, Mora n. et al. R-Ras promotes tumor growth of cervical epithelial cells" Cancer (2003) vol. 97, pp. 575-585.
Roy, M. et al., "The multifaceted role of Notch in cancer" Curr Opin Genet Devel (2007) vol. 17, pp. 52-59.
Schwarz, K. et al., "The deacetylase inhibitor LAQ824 induces notch signalling in haematopoietic progenitor cells" Leukemia Research (2011) vol. 35, pp. 119-125.

(Continued)

*Primary Examiner* — Karlheinz R Skowronek
*Assistant Examiner* — Roy Teller
(74) *Attorney, Agent, or Firm* — Calfee, Halter & Griswold LLP; Harry J. Guttman

(57) ABSTRACT

Multicomponent compositions and methods of use thereof are disclosed herein. Some embodiments of the present invention include multicomponent compositions comprising a first component and a second component, where the first component comprises a notch influencing molecule and the second component comprises a GPCR targeted molecule. Kits comprising the multicomponent composition are also disclosed. Methods for providing the multicomponent composition to one or more cells are additionally provided. Further embodiments include methods of using the multicomponent composition such as, for example, methods of administering the multicomponent composition and method of treating organisms (such as mammals) using the multicomponent composition.

13 Claims, 55 Drawing Sheets

(56) References Cited

OTHER PUBLICATIONS

Sjölund J et al., "The Notch pathway in cancer: differentiation gone awry" Eur J Cancer (2005) vol. 41, pp. 2620-2629.
Sparrow, Angela M. et al., "Central Neuropeptide Y Modulates Binge-Like Ethanol Drinking in C57BL/6J Mice via Y1 and Y2 Receptors" Neuropsychopharmacology (2012) vol. 37, pp. 1409-1421.
Srinivasan, Venkatramanujam et al., "Melatonin and Its Agonist Ramelteon in Alzheimer's Disease: Possible Therapeutic Value" International Journal of Alzheimer's Disease (2011), Art. ID 741974, 15 pages.
Srivastava, S. et al., "Notch1 regulates the functional contribution of RhoC to cervical carcinoma progression" Br J Cancer (2010) vol. 102, pp. 196-205.
Stefan, H. et al., "Novel anticonvulsant drugs" Pharmacol Ther (2007) vol. 113, pp. 165-183.
Sun, Lichun et al., "Examination of the 1,4-disubstituted azetidinone ring system as a template for combretastatin A-4 conformationally restricted analogue design" Bioorganic & Medicinal Chemistry Letters (2004a) vol. 14, pp. 2041-2046.
Sun, Lichun et al., "Effects of Camptothecin Conjugated to a Somatostatin Analog Vector on Growth of Tumor Cell Lines in Culture and Related Tumors in Rodents" Drug Delivery (2004b) vol. 11, pp. 231-238.
Sun, Li-Chun et al., "Effects of camptothecin on tumor cell proliferation and angiogenesis when coupled to a bombesin analog used as a targeted delivery vector" Anti-Cancer Drugs (2007a) vol. 18, pp. 341-348.
Sun, L. et al., "Aberrant expression of Notch1 in cervical cancer" Chinese J of Clin Oncol (2007b) vol. 4, No. 1, pp. 38-41.
Sun, L. et al., "Cytotoxic conjugates of peptide hormones for cancer chemotherapy" Drugs of the Future (2008a) vol. 33, No. 3, pp. 217-223.
Sun, Li-Chun et al., "Targeted Chemotherapy Using a Cytotoxic Somatostatin Conjugate to Inhibit Tumor Growth and Metastasis in Nude Mice" Clinical Medicine: Oncology (2008b) vol. 2, pp. 491-499.
Sun L. et al., "Somatostatin Receptor-targeted Anti-cancer Therapy" Current Drug Delivery (2011a) vol. 8, pp. 2-10.
Sun, L. et al., "Investigation of Cancer Cell Lines for Peptide Receptor-targeted Drug Development" J Drug Target (2011b) vol. 19, No. 8, pp. 719-730.
Susini, C. et al., "Rationale for the use of somatostatin analogs as antitumor agents" Ann Oncol (2006) vol. 17, pp. 1733-1742.
Talora, C. et al., "Constitutively active Notch1 induces growth arrest of HPV-positive cervical cancer cells via separate signaling pathways" Exp Cell Res (2005) vol. 305, pp. 343-354.
Talora, C. et al., "Cross talk among Notch3, pre-TCR, and Tal1 in T-cell development and leukemogenesis" Blood (2006) vol. 107, No. 8, pp. 3313-3320.
Talora, C. et al., "Specific down-modulation of Notch1 signaling in cervical cancer cells is required for sustained HPV-E6/E7 expression and late steps of malignant transformation" Genes & Dev (2002) vol. 16, pp. 2252-2263.
Tewari, KS. et al., "Development and assessment of a general theory of cervical carcinogenesis utilizing a severe combined immunodeficiency murine-human xenograft model" Gynecol Oncol (2000) vol. 77, pp. 137-148.
Thiery, JP., "Epithelial-mesenchymal transitions in tumour progression" Nat Rev Cancer (2002) vol. 2, pp. 442-454.
Tsai, Cheguo et al., "Valproic acid suppresses cervical cancer tumor progression possibly via activating Notch1 signaling and enhances receptor-targeted cancer chemotherapeutic via activating somatostatin receptor type II" Arch Gynecol Obstet (2013) vol. 288, Issue 2, pp. 393-400.
Wang Z, et al., "Down-regulation of Notch-1 and Jagged-1 inhibits prostate cancer cell growth, migration and invasion, and induces apoptosis via inactivation of Akt, mTOR, and NF-kappaB signaling pathways" J Cell Biochem (2010) vol. 109, pp. 726-736.

Wang, L., et al., "Overexpressed active Notch1 induces cell growth arrest of HeLa cervical carcinoma cells" Int J Gynecol Cancer (2007) vol. 17, pp. 1283-1292.
Weijzen, S., et al., "HPV16 E6 and E7 oncoproteins regulate Notch-1 expression and cooperate to induce transformation" J Cell Physiol (2003) vol. 194, pp. 356-362.
Weng, AP et al., "Multiple niches for Notch in cancer: context is everything" Curr Opin Genet Dev (2004) vol. 14, pp. 48-54.
Wu, L. et al., "MAML1, a human homologue of Drosophila mastermind, is a transcriptional co-activator for NOTCH receptors" Nat Genet (2000) vol. 26, pp. 484-489.
Wu, L. et al., "Modulation of Notch signaling by mastermind-like (MAML) transcriptional co-activators and their involvement in tumorigenesis" Semin Cancer Biol. (2004) vol. 14, pp. 348-356.
Xiao, D. et al., "The human gastrin-releasing peptide receptor gene structure, its tissue expression and promoter" Gene (2001) vol. 264, pp. 95-103.
Yao, J., et al., "Notch1 induces cell cycle arrest and apoptosis in human cervical cancer cells: involvement of nuclear factor kappa B inhibition" Int J Gynecol Cancer (2007) vol. 17, pp. 502-510.
Yu, H. et al., "Blocking Notch1 signaling by RNA interference can induce growth inhibition in HeLa cells" Int J Gynecol Cancer (2007) vol. 17, pp. 511-516.
Yue, Xu et al., "Effects of the novel glycopeptide opioid agonist MMP-2200 in preclinical models of Parkinson's disease" Brain Research (2011) vol. 1413, pp. 72-83.
Zagouras, P. et al., "Alterations in Notch signaling in neoplastic lesions of the human cervix" PNAS (1995) vol. 92, pp. 6414-6418.
_PCT/US2012/025479, International Search Report, mailed Dec. 17, 2012, 8 pages.
_PCT/US2012/025479, Written Opinion, mailed Dec. 17, 2012, 5 pages.
Adler, JT. et al., "Inhibition of growth in medullary thyroid cancer cells with histone deacetylase inhibitors and lithium chloride" J Surg Res (2010) vol. 159, pp. 640-644 Epub 2008; Sep 4.
Allenspach, EJ et al., "Notch signaling in cancer" Cancer Biol Ther (2002) vol. 1, Issue 5, pp. 466-476.
Arimura, Akira et al., "Potential protective action of pituitary adenylate cyclase-activating polypeptide (PACAP38) on in vitro and in vivo models of myeloma kidney injury" Blood Journal, American Society of Hematology (2006) vol. 107, No. 2, pp. 661-668.
Bellavia, D. et al., "Combined expression of pTalpha and Notch3 in T cell leukemia identifies the requirement of preTCR for leukemogenesis" PNAS (2002) vol. 99, No. 6, pp. 3788-3793.
Bellavia, D. et al., "Notch3 and the Notch3-upregulated RNA-binding protein HuD regulate ikaros alternative splicing" EMBO J (2007) vol. 26, No. 6, pp. 1670-1680.
Bolós V. et al., "Notch signalling in cancer stem cells" Clin Transl Oncol (2009) vol. 11, pp. 11-19.
Bolós V. et al., "The transcription factor Slug represses E-cadherin expression and induces epithelial to mesenchymal transitions: a comparison with Snail and E47 repressors" J Cell Sci (2003) vol. 116, pp. 499-511.
Burian, Bernhard et al., "Vasoactive intestinal peptide (VIP) receptor expression in monocyte-derived macrophages from COPD patients" Peptides (2010) vol. 31, pp. 603-608.
Calzavara, E. et al., "Reciprocal regulation of Notch and PI3K/Akt signalling in T-ALL cells in vitro" J Cell Biochem. (2008) vol. 103, pp. 1405-1412.
Celinski, SA. et al., "Somatostatin receptor gene transfer inhibits established pancreatic cancer xenografts" J Surg Res (2003) vol. 115, pp. 41-47.
Chateauvieux, S. et al., "Molecular and therapeutic potential and toxicity of valproic acid" J Biomed Biotechnol (2010) Article ID 479364, 18 pages.
Decressac, Mickael et al., "Neuroprotection by neuropeptide Y in cell and animal models of Parkinson's disease" Neurobiology of Aging (2012) vol. 33, pp. 2125-2137.
Dorsam, Robert T. et al., "G-protein-coupled receptors and cancer" Nature Reviews/Cancer (2007) vol. 7, pp. 79-94.
Dotto, GP, "Notch tumor suppressor function" Oncogene (2008) vol. 27, pp. 5115-5123.

(56) References Cited

OTHER PUBLICATIONS

Dragicevic, Natasa et al., "Melatonin treatment restores mitochondrial function in Alzheimer's mice: a mitochondrial protective role of melatonin membrane receptor signaling" Journal of Pineal Research (2011) vol. 51, pp. 75-86.
Du, ZY, et al., "Gene transfer of somatostatin receptor type 2 by intratumoral injection inhibits established pancreatic carcinoma xenografts" World J Gastroenterol (2005) vol. 11, No. 4, pp. 516-520.
Dueñas-González, A. et al., "Epigenetics of cervical cancer. An overview and therapeutic perspectives" Mol Cancer (2005) vol. 4, pp. 38-61.
Dueñas-González,, Alfonso et al., "Valproic acid as epigenetic cancer drug: Preclinical, clinical and transcriptional effects on solid tumors" Cancer Treatment Reviews (2008) vol. 34, pp. 206-222.
Engel, J.B. et al., "Targeted cytotoxic bombesin analog AN-215 effectively inhibits experimental human breast cancers with a low induction of multi-drug resistance proteins" Endocr Relat Cancer (2005) vol. 12, pp. 999-1009.
Franko-Tobin, Laura G. et al., "Notch1-mediated Tumor Suppression in Cervical Cancer with the Involvement of SST Signaling and its Application in Enhanced SSTR-targeted Therapeutics" Oncologist (2012) Epub 30 vol. 17, pp. 220-232.
Fuselier, Joseph et al., "An Adjustable Release Rate Linking Strategy for Cytotoxin-Peptide Conjugates" Bioorganic & Medicinal Chemistry Letters (2003) vol. 13, pp. 799-803.
Georgeseu, M-M., "PTEN Tumor Suppressor Network in PI3K-Akt Pathway Control" Genes & Cancer (2010) vol. 1, No. 12, pp. 1170-1177.
Ghosh, S. et al., "Somatostatin modulates PI3K-Akt, eNOS and NHE activity in the ciliary epithelium" Mol Cell Endocrinol. (2006) vol. 253, pp. 63-75.
Greenblatt, DY. et al., "Valproic acid activates Notch1 signaling and induces apoptosis in medullary thyroid cancer cells" Ann Surg (2008) vol. 247, pp. 1036-1040.
Greenblatt, DY. et al., "Valproic acid activates notch-1 signaling and regulates the neuroendocrine phenotype in carcinoid cancer cells", Oncologist (2007) vol. 12, pp. 942-951.
Grozinsky-Glasberg, S. et al., "Somatostatin analogues in the control of neuroendocrine tumours: efficacy and mechanisms" Endocr Relat Cancer (2008) vol. 15, pp. 701-720.
Guan, E. et al., "T cell leukemia-associated human Notch/translocation-associated Notch homologue has I kappa B-like activity and physically interacts with nuclear factor-kappa B proteins in T cells" J Exp Med (1996) vol. 183, pp. 2025-2032.
Johannessen, CU et al., "Valproate: past, present, and future" CNS Drug Rev (2003) vol. 9, No. 2, pp. 199-216.
Kasperlik-Zaluska, Anna A. et al., "ACTH responses to somatostatin, valproic acid and dexamethasone in Nelson's syndrome" Neuroendocrinology Letters (2005) vol. 26, No. 6, pp. 709-712.
Koch, U. et al., "Notch and cancer: a double-edged sword" Cell Mol Life Sci. (2007) vol. 64, pp. 2746-2762.
Kulkarni, S. et al., "Cyclooxygenase-2 is overexpressed in human cervical cancer" Clin Cancer Res (2001) vol. 7, pp. 429-434.
Kunnimalaiyaan M, et al., "Overexpression of the NOTCH1 intracellular domain inhibits cell proliferation and alters the neuroendocrine phenotype of medullary thyroid cancer cells" J Biol Chem (2006) vol. 281, No. 52, pp. 39819-39830.

Kunnimalaiyaan, M. et al., "Tumor suppressor role of Notch-1 signaling in neuroendocrine tumors" Oncologist (2007) vol. 12, pp. 535-542.
Kunnimalaiyaan, M. et al., "Conservation of the Notch1 signaling pathway in gastrointestinal carcinoid cells" Am J Physiol Gastrointest Liver Physiol (2005) vol. 289, pp. G636-G642.
Leong, KG et al., "Recent insights into the role of Notch signaling in tumorigenesis" Blood (2006) vol. 107, pp. 2223-2233.
Li, Min et al., "Renoprotection by pituitary adenylate cyclase-activating polypeptide in multiple myeloma and other kidney diseases" Regulatory Peptides (2008) vol. 145, pp. 24-32.
Livak, Kenneth J. et al., "Analysis of Relative Gene Expression Data Using Real-Time Quantitative PCR and the 2 ΔΔCT Method" Methods (2001) vol. 25, pp. 402-408.
Loeken, MR., "Effects of mutation of the CREB binding site of the somatostatin promoter on cyclic AMP responsiveness in CV-1 cells" Gene Expr (1993) vol. 3, No. 3, pp. 253-264.
Ma, YY et al., "PIK3CA as an oncogene in cervical cancer" Oncogene (2000) vol. 19, pp. 2739-2744.
Maillard I and Pear, WS., "Notch and cancer: best to avoid the ups and downs" Cancer Cell (2003) vol. 3, pp. 203-205.
Maillard, I. et al., "Regulation of lymphoid development, differentiation, and function by the Notch pathway" Annu Rev Immunol (2005) vol. 23, pp. 945-974.
Malinowski, DP, "Multiple biomarkers in molecular oncology. I. molecular diagnostics applications in cervical cancer detection" Expert Rev Mol Diagn (2007) vol. 7, No. 2, pp. 117-131.
Marks, PA.' "Histone deacetylase inhibitors: a chemical genetics approach to understanding cellular functions" . Biochim Biophys Acta. (2010) vol. 1799, pp. 717-725.
Mohammed, TA. et al., "Pilot Phase II Study of Valproic Acid for Treatment of Low-Grade Neuroendocrine Carcinoma" Oncologist (2011) vol. 16, pp. 835-843.
Moody, Terry W. et al., "In Vitro and in Vivo Antitumor Effects of Cytotoxic Camptothecin-Bombesin Conjugates Are Mediated by Specific Interaction with Cellular Bombesin Receptors" The Journal of Pharmacology and Experimental Therapeutics (2006) vol. 318, No. 3, pp. 1265-1272.
Nakakura, EK, et al., "Regulation of neuroendocrine differentiation in gastrointestinal carcinoid tumor cells by Notch signaling". J Clin Endocrinol Metab (2005) vol. 90, No. 7, pp. 4350-4356.
Ning, L. et al., "Suberoyl Bis-Hydroxamic Acid Activates Notch-1 Signaling and Induces Apoptosis in Medullary Thyroid Carcinoma Cells" The Oncologist (2008) vol. 13, pp. 98-104.
Panetta, R. et al., "Expression of mRNA for all five human somatostatin receptors (hSSTR1-5) in pituitary tumors" Life Sciences (1995) vol. 56, No. 5, pp. 333-342.
Chinese Application No. 201280009550.9, English-language translation of First Office Action mailed Aug. 5, 2014, 8 pages.
Chinese Application No. 201280009550.9, English-language translation of Second Office Action mailed Apr. 13, 2015, 9 pages.
Macaulay et al., "Experimental and clinical studies with somatostatin analogue octreotide in small cell lung cancer" Br. J. Cancer (1991), vol. 64, pp. 451-456.
Platta et al., "Valproic Acid Induces Notch1 Signaling in Small Cell Lung Cancer Cells" J Surg Res. (2008) vol. 148, No. 1, pp. 31-37.

* cited by examiner

MTT assay

Hela-GFP Control

Hela-ICN1 & Apoptosis
(Arrow shows apoptosis)

Pancreatic carcinoid BON cells

*Cervical cancer Hela cells*

SEQUENCE LISTING

```
<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: Mammal

<400> SEQUENCE: 1

Ala Gly Cys Lys Asn Phe Phe Trp Lys Thr Phe Thr Ser Cys
1               5                   10
```

MULTICOMPONENT COMPOSITIONS AND THEIR USES

CROSS-REFERENCE TO RELATED APPLICATIONS

This application is the U.S. national stage entry of PCT/US2012/025479, with an international filing date of Feb. 16, 2012, which is herein incorporated by reference in its entirety, which claims the benefit of (a) U.S. Provisional Application No. 61/463,482, filed Feb. 17, 2011, which is herein incorporated by reference in its entirety and (b) U.S. Provisional Application No. 61/558,227, filed Nov. 10, 2011, which is herein incorporated by reference in its entirety.

BACKGROUND

The Notch gene family encodes single-pass, heterodimeric type I trans-membrane receptors. Notch signaling is activated by the DSL (Delta, Serrate, Lag-2) family of trans-membrane ligands between two neighboring cells and involves cell-cell communication. There are four Notch receptors and at least five mammalian ligands identified to date. Notch receptors are heterodimers, each consisting of an extracellular domain (ECN), a transmembrane domain, and an intracellular domain (ICN). ICN contains a RAM domain involved in CSL binding, ankyrin repeats (ANK), nuclear localization signals (NLS), and a PEST sequence. Transcriptional activation domain (TAD) differs among the four receptors. ECN contains multiple EGF-like repeats and LIN12/Notch repeats (LNR).

Notch signaling can begin with a ligand binding to the extracellular domain of Notch (ECN), which induces proteolytic cleavage and releases the active intracellular domain of Notch (ICN). ICN then translocates to the nucleus and binds to CSL, a DNA-binding transcriptional factor, and initiates the transcription of CSL-dependent Notch target genes.

G protein-coupled receptors (GPCRs) are known as seven-transmembrane domain receptors. GPCRs can mediate downstream signaling pathways via G proteins. Two of the signal transduction pathways involving GPCRs are cAMP and phosphatidylinositol signal pathways. There are five somatostatin receptor (SSTR) subtypes, three bombesin receptor subtypes, and three PACAP receptor subtypes, which belong to the GPCR superfamily Somatostatin (SST), a somatotropin release-inhibiting factor (SRIF), also known as a growth hormone-inhibiting hormone (GHIH), is a peptide hormone with two active forms (SST-14 and SST-28) and can be secreted by endocrine cells. SST can act as an endogenous inhibitory regulator of a diverse array of cellular functions such as cell proliferation and hormone-release. SST can exert its functions by activating G protein-coupled SSTR or inhibiting release of growth factors.

Some embodiments of the invention include compositions comprising compositions or molecules that may take advantage of the above functions. Other embodiments, objects, and advantages of this invention will become readily apparent from the ensuing description.

SUMMARY

Some embodiments of the invention include a multicomponent composition comprising a first component and a second component, where the first component is a composition comprising a notch influencing molecule and the second component is a composition comprising a GPCR targeted molecule. The notch influencing molecule can, in some instances, be a notch ligand, a notch receptor, a molecule that activates notch signaling, or a molecule that inhibits notch signaling. In certain embodiments, the notch influencing molecule can be VPA, SBHA, DBZ, or NLE. In certain embodiments, the GPCR targeted molecule is cytotoxic. In other embodiments, the GPCR targeted molecule is cytotoxic to cancer cells. The GPCR targeted molecule can, in some instances, be a conjugate chosen from Formula (I), can be SST-14, or can be an SST analog. For example, the conjugate can be COL-SST, CPT-SST, or CPT-BN. In some embodiments, the notch influencing molecule is VPA and the GPCR targeted molecule is CPT-SST. In other embodiments, the notch influencing molecule is VPA and the GPCR targeted molecule is COL-SST. In some exemplary embodiments, the notch influencing molecule is VPA at a concentration ranging from about 0.25 mM to about 20 mM and the GPCR targeted molecule is CPT-SST at a concentration ranging from about 0.01 µM to about 50 µM. And in other embodiments, the notch influencing molecule is VPA at a concentration ranging from about 0.25 mM to about 20 mM and the GPCR targeted molecule is COL-SST at a concentration ranging from about 0.01 µM to about 50 µM.

Still other embodiments of the invention include pharmaceutical compositions comprising the multicomponent composition. In some instances, the notch influencing molecule is VPA at a dosage concentration ranging from about 1 mg/kg to about 50 mg/kg. In still other embodiments, the notch influencing molecule is SBHA at a dosage concentration ranging from about 0.01 mg/kg to about 25 mg/kg. In other embodiments, the GPCR targeted molecule is CPT-SST, COL-SST, or CPT-BN, and dosage concentration of the GPCR targeted molecule ranges from about 0.01 mg/kg to about 10 mg/kg. Other examples include a pharmaceutical composition where the notch influencing molecule is VPA at a dosage concentration ranging from about 1 mg/kg to about 50 mg/kg and the GPCR targeted molecule is CPT-SST at a concentration ranging from about 0.01 mg/kg to about 10 mg/kg. In other examples of this pharmaceutical composition, the notch influencing molecule is VPA at a dosage concentration ranging from about 1 mg/kg to about 50 mg/kg and the GPCR targeted molecule is COL-SST at a concentration ranging from about 0.01 mg/kg to about 10 mg/kg. And yet other examples include pharmaceutical compositions where the notch influencing molecule is SBHA at a dosage concentration ranging from about 0.01 mg/kg to about 25 mg/kg, the GPCR targeted molecule is CPT-SST, COL-SST, or CPT-BN, and the GPCR targeted molecule concentration ranges from about 0.01 mg/kg to about 10 mg/kg.

Other embodiments of the invention include methods comprising administering the multicomponent composition to at least one cell. In some instances, the multicomponent composition is a pharmaceutical composition. In some embodiments of this method, the cell is a cancer cell which can be a cell from cervical cancer, pancreatic cancer, pancreatic carcinoid, lung cancer, small cell lung cancer (SCLC), skin cancer, medullary thyroid cancer (MTC), cutaneous squamous cell carcinoma, colonrectal cancer, osteosarcoma, hepatoma, leukemia, ovarian cancer, tumors, or endocrine tumors. In still other embodiments, the administering is to an organism, such as an animal (e.g., a human or a rodent). The method of administering can be, for example, orally, intranasally, or via injection (e.g., via intravenous, intraperitoneal, intramuscular, or subcutaneous injection).

Other embodiments of the invention include methods for treating cancer in animals comprising administering the multicomponent composition to the animal. In some instances, the multicomponent composition is a pharmaceutical composition. The animal can be, for example, a mammal such as a human or a rodent. The administration can occur, for example, orally, intranasally, or by injection (e.g., by intravenous, by intraperitoneal, by intramuscular, or by subcutaneous injection). In some embodiments, the cancer to be treated can be cervical cancer, pancreatic cancer, pancreatic carcinoid, lung cancer, small cell lung cancer (SCLC), skin cancer, medullary thyroid cancer (MTC), cutaneous squamous cell carcinoma, colonrectal cancer, osteosarcoma, hepatoma, leukemia, ovarian cancer, tumors, or endocrine tumors. In some instances the treating suppresses epithelial-mesenchymal transition in cancer cells.

Other embodiments of the invention include kits that comprise the multicomponent composition.

BRIEF DESCRIPTION OF THE DRAWINGS

The following drawings form part of the present specification and are included to further demonstrate certain aspects of the present invention. The invention may be better understood by reference to one or more of these drawings in combination with the description of specific embodiments presented herein.

DETAILED DESCRIPTION

Figure 1:
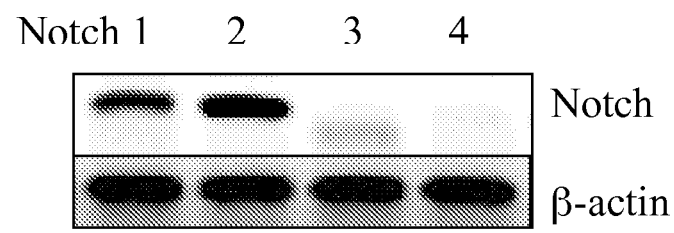
FIG. 1. RT-PCR detection for the expression of four Notch receptors in normal Hela cells. Notch1 and Notch2 were expressed and no expression or trace expression of Notch3 and Notch4 occurred.

Some embodiments of the invention include a multicomponent composition comprising two components, a first component and a second component.

The first component comprises a first composition that can comprise a notch influencing molecule. Notch-influencing molecules can include, but are not limited to notch ligands (e.g., Jagged1, Jagged2, Delta1, Delta-like 1(Dll1), Dll3, and Dll4), notch receptors (e.g., Notch1, Notch2, Notch3, and Notch4), molecules that activate notch signaling (e.g., valproic acid (VPA) and suberoyl bis-hydroxamic acid (SBHA)), or molecules that inhibit notch signaling (e.g., Z-Leu-Leu-Nle-CHO (Nle=Norleucine) (NLE) and dibenzazepine (DBZ)). In some embodiments, the notch influencing molecule is a histone deacetylase inhibitor which can be, but is not limited to carboxylates (e.g., sodium butyrate, valproic acid, sodium phenylbutyrate and pivaloyloxymethyl butyrate), hydroxamic acids (e.g., suberoylanilide hydroxamic acid (SAHA), trichostatin A (7-[4-(dimethylamino)phenyl]-N-hydroxy-4,6-dimethyl-7-oxohepta-2,4-dienamide), SBHA), benzamides (e.g., CI-994 (4-Acetylamino-N-(2'-aminophenyl)benzamide) and MS-275 (N-(2-aminophenyl)-4-[N-(pyridine-3-yl-methoxy-carbonyl)aminomethyl]benzamide), epoxyketones (e.g., Trapoxin B and 2-amino-8-oxo-9,10-epoxydecanoic acid), cyclic peptides (e.g., Apicidin (cyclo(N-β-methyl-L-tryptophanyl-L-isoleucinyl-D-pipecolinyl-L-2-amino-8-oxodecanoyl)) and depsipeptides), hybrid molecules (e.g., CHAP31 and CHAP50), cyclostellettamines, and carbamazepines. In other embodiments, the notch influencing molecule can be a notch inhibitor, such as, but not limited to, Z-Leu-Leu-Nle-CHO (Nle=Norleucine) (NLE), dibenzazepine (DBZ), gamma-secretase inhibitor (e.g., MRK003), Benzyloxycarbonyl-Leu-Leu-Nle-CHO (LLNle), N—[N-(3,5-difluorophenacetyl)-L-alanyl]-S-phenylglycine t-butyl ester (DAPT), and L685458 ((5S)-(t-Butoxycarbonylamino)-6-phenyl-(4R)hydroxy-(2R)benzylhexanoyl)-L-leu-L-phe-amide). In some embodiments, the histone deacetylase (HDAC) inhibitor, can be, but not limited to, valproic acid (VPA) or suberoyl bis-hydroxamic acid (SBHA).

In some embodiments, the notch influencing molecule is targeted to a notch receptor. In some embodiments, the notch influencing molecule results in an increased expression of SST, in an increased expression of one or more SSTRs, in an up-regulation of SST signaling, in a change in expression of a GPCR, or combinations thereof. In some instances, the GPCR can be an SSTR (e.g., SSTR1, SSTR2, SSTR3, SSTR4, or SSTR5), a gastrin-releasing peptide receptor (GRPR), BRS3, NMBR, PAC1, VPAC1, and VPAC2. In some embodiments, the notch influencing molecule increases the expression of intracellular domain of Notch (ICN), increases the intracellular amount of the ICN, or increases the extracellular amount of the ICN.

In some embodiments, the notch influencing molecule is VPA and the VPA concentration ranges from about 0.1 mM to about 50 mM, about 1 mM to about 10 mM, and can be, for example, about 0.1 mM, about 0.2 mM, about 0.3 mM, about 0.4 mM, about 0.5 mM, about 0.6 mM, about 0.7 mM, about 0.8 mM, about 0.9 mM, about 10 mM, or about 25 mM. In some embodiments, the notch influencing molecule is SBHA, DBZ, or NLE and the notch influencing molecule concentration ranges from about 0.1 µM to about 100 µM, about 0.1 µM to about 50 µM, or about 1 µM to about 10 µM, and can be, for example, about 0.1 µM, about 0.2 µM, about 0.3 µM, about 0.4 µM, about 0.5 µM, about 0.6 µM, about 0.7 µM, about 0.8 µM, about 0.9 µM, about 10 µM, about 20 µM, about 30 µM, about 40 µM, or about 50 µM.

The second component of the multicomponent composition comprises a second composition that can comprise a GPCR targeted molecule. In some instances, the GPCR targeted molecule can be a conjugate or a polypeptide (e.g., SST-14, SST-28, or an SST analog). In some embodiments, the GPCR targeted molecule is cytotoxic to cells. In other embodiments, the GPCR targeted molecule is cytotoxic to cancer cells. In some instances, the targeted GPCR can be an SSTR (e.g., SSTR1, SSTR2, SSTR3, SSTR4, or SSTR5), a gastrin-releasing peptide receptor (GRPR), BRS3, NMBR, PAC1, VPAC1, or VPAC2. In other embodiments, the GPCR targeted molecule can result in an increased expression of SST, in an increased expression of one or more SSTRs, in an up-regulation of SST signaling, or combinations thereof. In still other embodiments, the notch influencing molecule can increase the expression of GPCR (e.g., an SSTR) which can then enhance the effect of the GPCR targeted molecule. The GPCR targeted molecule enhancement can, for example, result in enhanced treatments for cancer, including but not limited to cancer cell growth suppression or tumor growth suppression.

In some embodiments when the GPCR targeted molecule is a polypeptide, it can be an SST-14 or an SST analog. SST-14 is Ala-Gly-Cys-Lys-Asn-Phe-Phe-Trp-Lys-Thr-Phe-Thr-Ser-Cys (SEQ ID NO:1). SST-14 is also referred to herein as DC-53-99. In certain embodiments, an SST analog can be a polypeptide that is similar in sequence to SST-14, but still targets GPCR. In some instances, the SST analog comprises one or more conservative mutations from SST-14. In other instances, the SST analog comprises at least 4, 5, 6, 7, 8, 9, 10, 11, 12, 13, or 14 amino acids that are the same (e.g., in the same relative position) as SST-14. In some instances, the SST analog comprises 5, 6, 7, 8, 9, 10, 11, 12, 13, 14, 15, 16, 17, 18, 19, 20, 21, 22, 23, 24, 25, 26, 27, 28, 29, or 30 amino acids. In some embodiments, the SST analog can be a somatostatin analog. In certain embodiments, the SST analog can be cyclic or comprises at least one cyclic structure; cyclization can occur, for example, by forming a disulfide bold between two cysteines. In some embodiments, the SST analog can be octreotide, octreotate, lanreotide, or pasireotide.

In some embodiments, when GPCR targeted molecule is a conjugate, the conjugate can be:

X—Y—Z-Q (Formula I)

where X is a univalent moiety, Y is a bond or a bivalent first linker, Z is a bond or a bivalent second linker, and Q is a univalent amino acid chain. In some embodiments, X is cytotoxic. In other embodiments, X is an anti-cancer moiety. In still other embodiments, Q can comprise D-amino acids, L-amino acids, or both. Q can, for example, comprise cyclic amino acid structures (e.g., cyclic structures created by a disulfide bond between two cysteines).

In some embodiments, X can be

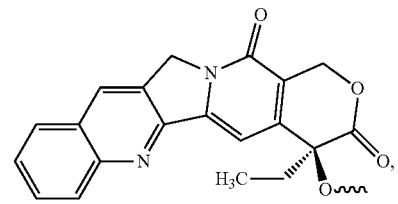

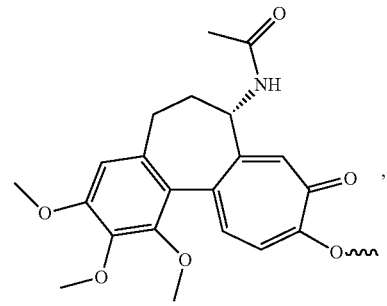

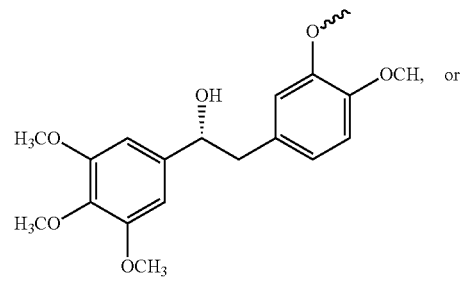

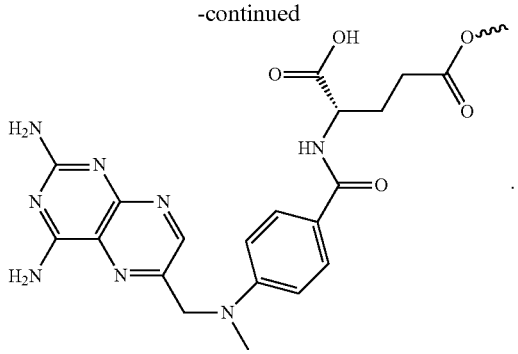

In some embodiments, Y can be a bond, or

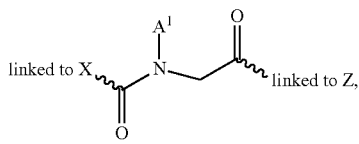

where $A^1$ can be —$CH_2$—$CH_2$—$NH_2$, —$CH_2$—$CH_2$—NH—$CH_3$, —$CH_2$—$CH_2$—N—$(CH_3)_2$, —$CH_2$—$CH_2$—$CH_2$—$NH_2$, or —$CH_2$—$CH_2$—OH.

In some embodiments, Z can be a bond,
{linked to Y}-NMeAmEtGly-Gaba-{linked to Q},
{linked to Y}-Gly-(Gaba)-{linked to Q},
{linked to Y}-(Gaba)-{linked to Q},
{linked to Y}-(D-Lys)-(D-Tyr)-Lys-(D-Tyr)-(D-Lys)-{linked to Q}, or
{linked to Y}-(D-Ser)-(Nle)-(D-Tyr)-(D-Ser)-{linked to Q}. Nle is norleucine.

In some embodiments, Q can be wwwCys-Phe-(D-Trp)-Lys-Thr-Cys-Thr-NH₂,
 |                              |
 S——————————————————————————————S
www(D-Phe)-Cys-Phe-(D-Trp)-Lys-Thr-Cys-Thr-NH₂,
        |                              |
        S——————————————————————————————S
www(D-Ser)-(D-Lys)-Gln-Trp-Ala-Val-(β-Ala)-His-Phe-Nle-NH₂,
www(D-,L-Ser)₁₄-(D-Ser)-(D-Lys)-Gln-Trp-Ala-Val-(β-Ala)-His-Phe-Nle-NH₂,
www(D-Ser)-(D-Tyr)-Gln-Trp-Ala-Val-(β-Ala)-His-Phe-Nle-NH₂,
wwwGly-(D-Ser)-(D-Tyr)-Gln-Trp-Ala-Val-(β-Ala)-His-Phe-Nle-NH₂,
wwwCys-Lys-Asn-Phe-Phe-(D-Trp)-Lys-Thr-Phe-Thr-Ser-Cys-NH₂,
 |                                                    |
 S————————————————————————————————————————————————————S
wwwGaba-Cys-Lys-Asn-Phe-Phe-(D-Trp)-Lys-Thr-Phe-Thr-Ser-Cys-NH₂,
         |                                                    |
         S————————————————————————————————————————————————————S
wwwHis-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-NH₂, or
wwwHis-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg-Val-Lys-Asn-Lys-NH₂.

The above cyclic structures for Q are formed by disulfide linkages between the cysteines; the diagram emphasizes the linkage but the linked sulfurs are from the cysteines; no additional sulfur atoms are used to form those cyclic moieties.

In some embodiments, X is directly bonded to Q. In some embodiments, Z is a bond and Y is not a bond. In some embodiments, Y is a bond and Z is not a bond. In some embodiments, Formula I is (I-1)

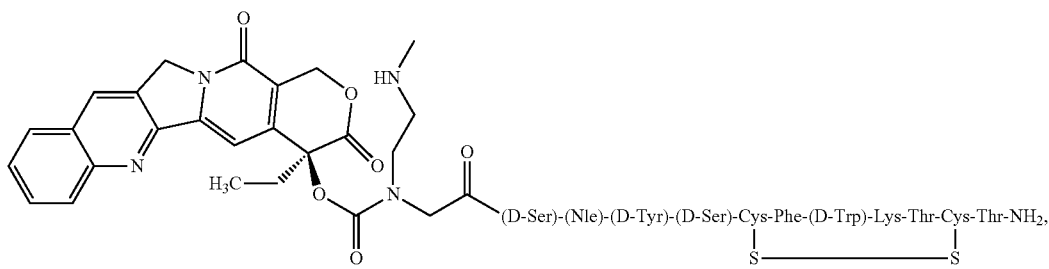

(I-2)

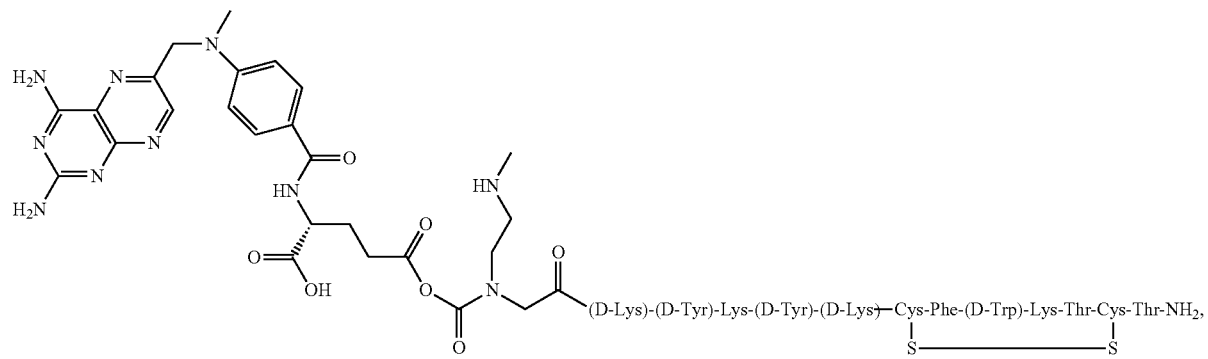

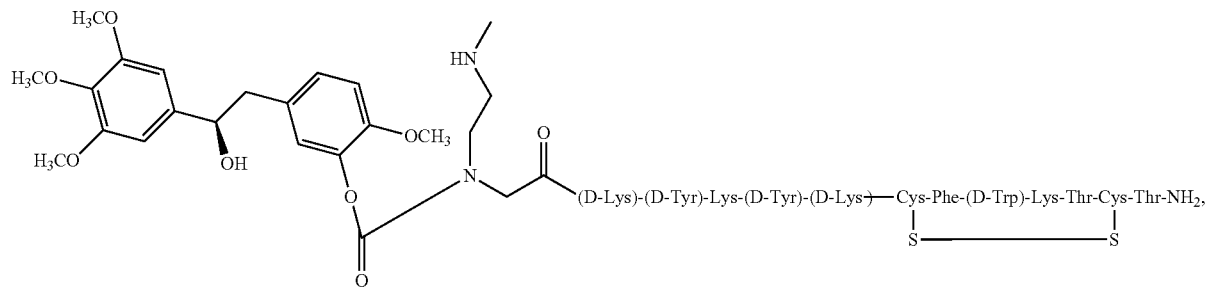
(I-3)
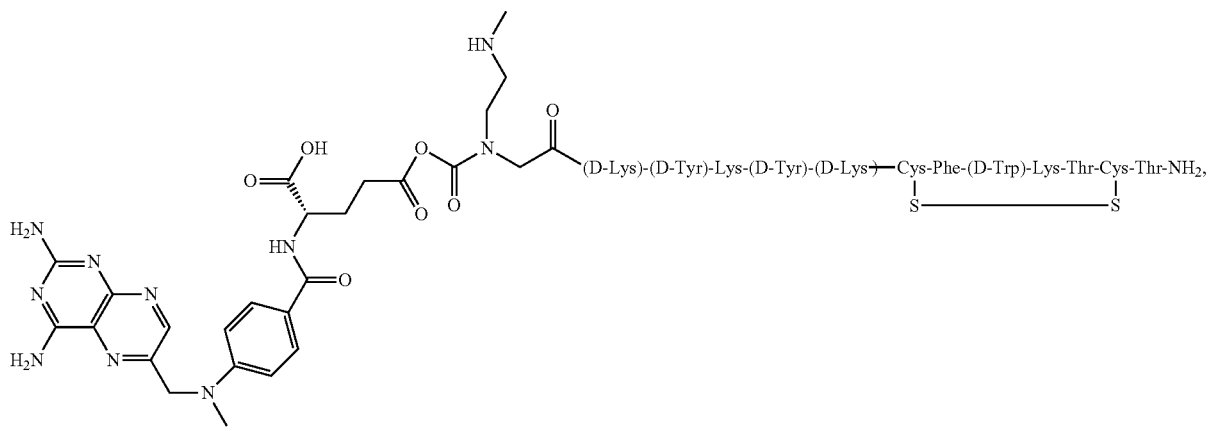
(I-4)
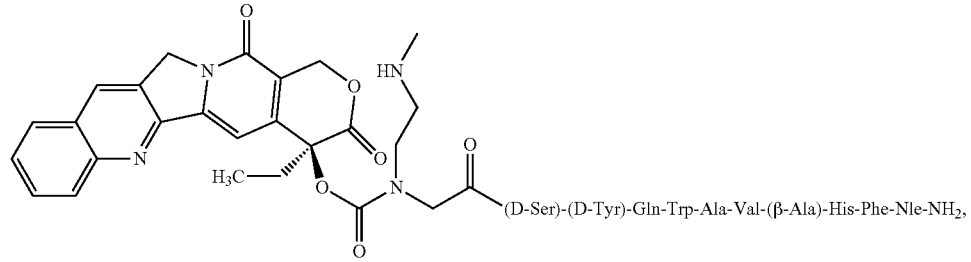
(I-5)
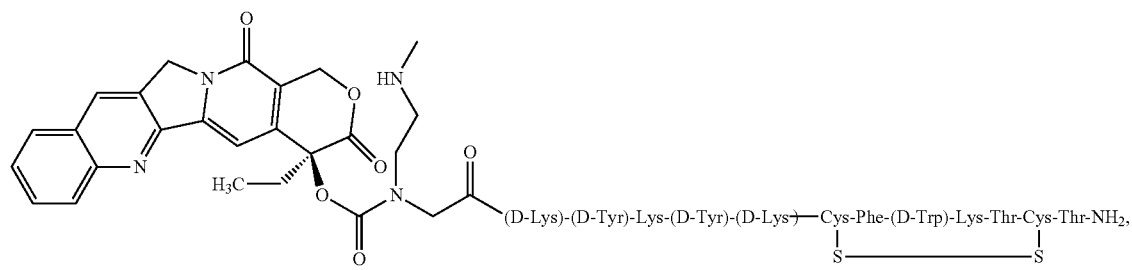
(I-6)
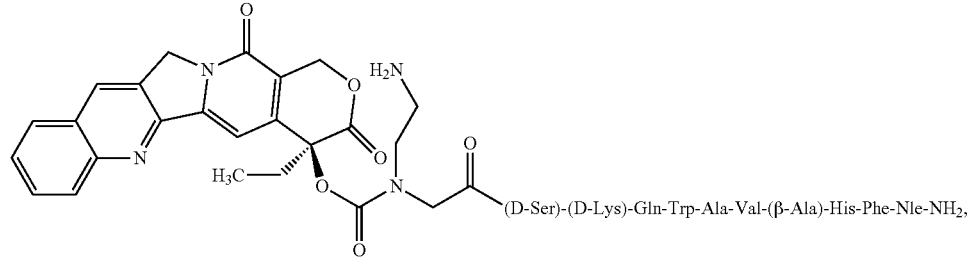
(I-7)

-continued

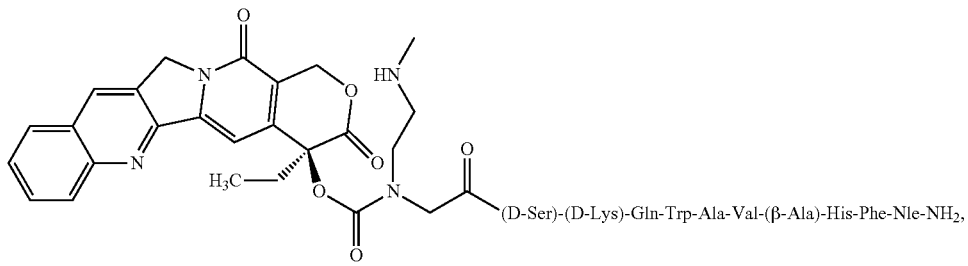
(I-8)

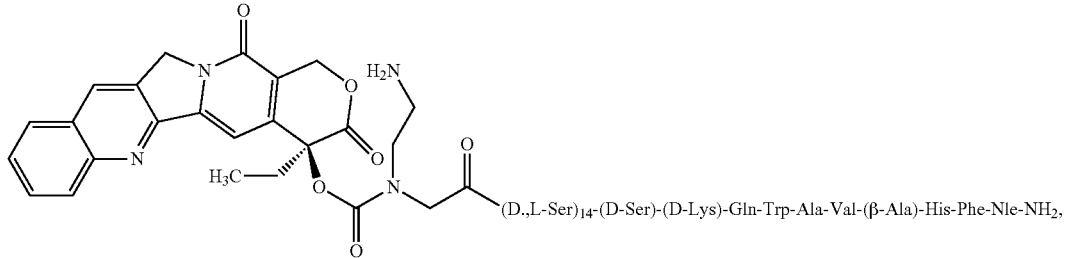
(I-9)

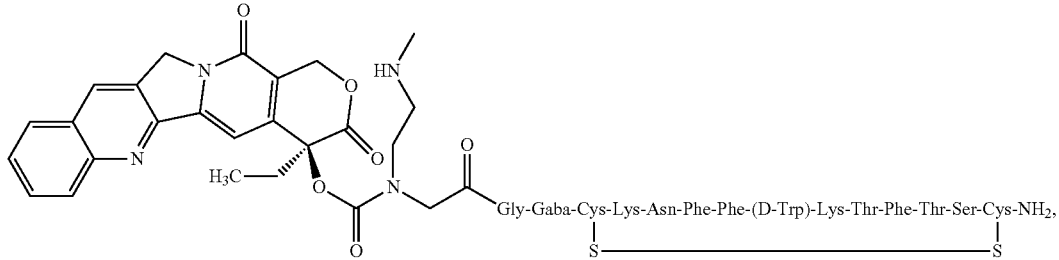
(I-10)

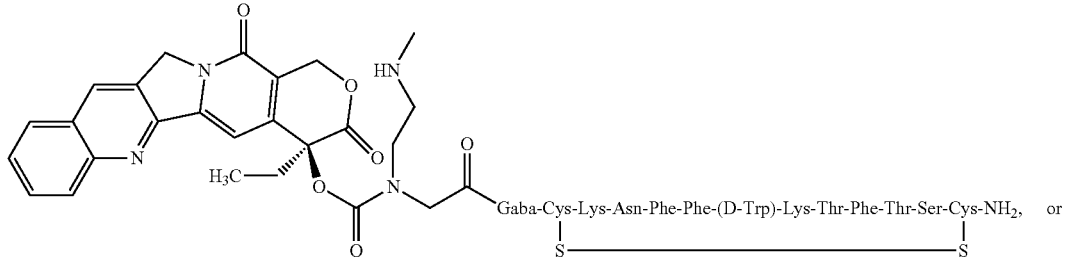
(I-11)

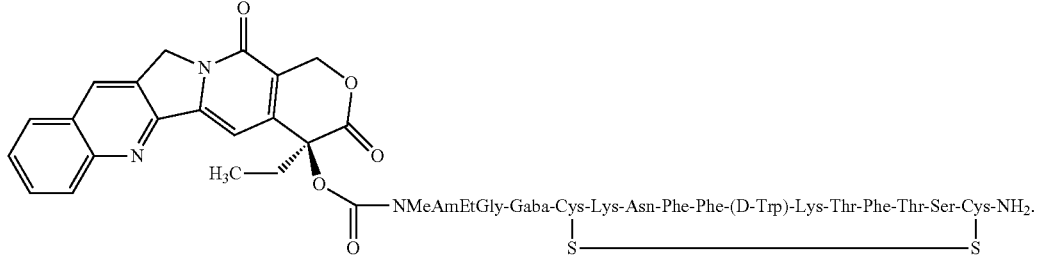
(I-12)

Formula (I-1) is referred to herein as CPT-SST or JF-10-81. Formula (I-2) is referred to herein as COL-SST or JF-16-87. Formula (I-3) is referred to herein as CA-SST. Formula (I-4) is referred to herein as MTX-SST. Formula (I-5) is referred to herein as CPT-BN. Formula (I-12) is referred to herein as DC-53-22. In some embodiments, the conjugate can be, but is not limited to, COL-SST, CPT-SST, CPT-BN, CA-SST, or MTX-SST. The Q portions of formulas (I-1)-(I-4) and (I-6) are formed by disulfide linkages between the cysteines; the diagram emphasizes the linkage but the linked sulfurs are from the cysteines, with no additional sulfur atoms used to form those cyclic moieties.

In some embodiments, the GPCR targeted molecule concentration ranges from about 0.1 µM to about 100 µM, about 0.1 µM to about 50 µM, or about 1 µM to about 10 µM, and can be, for example, about 0.1 µM, about 0.2 µM, about 0.3 µM, about 0.4 µM, about 0.5 µM, about 0.6 µM, about 0.7 µM, about 0.8 µM, about 0.9 µM, about 10 µM, about 20 µM, about 30 µM, about 40 µM, or about 50 µM.

In some embodiments, the GPCR targeted molecule is COL-SST or CST-SST and the GPCR targeted molecule concentration ranges from about 0.1 µM to about 100 µM, about 0.1 µM to about 50 µM, or about 1 µM to about 10 µM, and can be, for example, about 0.1 µM, about 0.2 µM, about 0.3 µM, about 0.4 µM, about 0.5 µM, about 0.6 µM, about 0.7 µM, about 0.8 µM, about 0.9 µM, about 10 µM, about 20 µM, about 30 µM, about 40 µM, or about 50 µM.

In some embodiments the multicomponent composition does not include one or more of cisplatin-topotecan, hydralazine, or topotecan. In some embodiments, the notch influencing molecule and the GPCR targeted molecule are not the same (e.g., they are not used together in a single species of the multicomponent composition). In some embodiments, the genus describing the notch influencing molecule and the genus describing the GPCR targeted molecule do not overlap.

Some embodiments of the invention include methods to administer the multicomponent composition to one or more cells. In some instances, the one or more cells can be cancer cells. In certain embodiments, the cell can be human pancreatic carcinoid BON cells (such as those in Dr. Courtney Townsend's laboratory at the University of Texas—Galveston), human T-cell acute lymphoblastic leukemia (T-ALL) HPB-ALL cells, osteosarcoma U2OS cells, lymphoma Jurkat cells, cervical cancer Hela cells, small cell lung cancer (SCLC) DMS-53, medullary thyroid cancer (MTC) TT cells, hepatoma HB-8064 (Hep3B), HTB-52 cells, ovarian cancer OVCAR8, SKOV3, NCI/ADR-RES cells, prostate cancer DU-145 cells, prostate cancer PC-3 cells, pancreatic cancer CFPAC-1 cells, lung cancer A549, leukemia MOLT-4 cells, and colon cancer HT-29 cells. In some embodiments, the cells can have normal, limited, or no expression of SST/SSTR(s). In some embodiments the cells are cancer cells that have normal, limited, or no expression of SST/SSTR(s).

Some embodiments of the inventions include methods to administer the composition to organisms (e.g., animals). In some instances the animal is a mammal, for example, but not limited to, a human, a rodent (e.g., a rat or a mouse), a horse, a dog, a cat, a pig, a cow, or a goat.

In still other embodiments of the invention, methods are used to treat animals using the composition. In certain embodiments, the method can be used to treat cancer. For example, the method can be used to treat cervical cancer, pancreatic cancer, pancreatic carcinoid, lung cancer, small cell lung cancer (SCLC), skin cancer, medullary thyroid cancer (MTC), cutaneous squamous cell carcinoma, colonrectal cancer, osteosarcoma, hepatoma, leukemia, ovarian cancer, tumors, and endocrine tumors. In still other embodiments, the treatment can suppress epithelial-mesenchymal transition (EMT) in cancer cells. In some embodiments the cancer type is glioma, neuroblastoma, breast, colon, prostate, hepatoma, endometrial, neuroectodermal, melanoma, teratocarcinoma, meduloblastoma, thoracic tumors (e.g., lung, esopagheal or mesothelioma), bladder, EBV-related tumors, carcinoid (e.g., gastrointestinal or lung), or fibrosarcoma. In some embodiments, the treatment results in one or more of the following to the cancer: suppression of cancer proliferation, suppression of tumor growth, apoptosis of cancer cells, anti-angiogenesis, anti-metastatic effects, chemo-sensitation, radio-sensitation, facilitation of an immune response against the tumor, arrest of growth of cancer cells, or arrest of tumor growth.

In some embodiments, the mammal is a human in need of treatment for a disease, condition, or disorder. For example, a mammal (e.g., human) can be in need of treatment for cancer, including any of those mentioned herein.

The methods of administering or treating an organism may occur in any manner, including, but not limited to oral treatment, intranasal treatment, or injection. For example, injection may include, but not be limited to, intravenous, intraperitoneal, intramuscular, or subcutaneous injection.

In some embodiments, the methods of treating an organism will involve treatment using a combination of a first component and a second component. The amount of the notch influencing molecule in the multicomponent composition will depend on numerous factors, including, for example, the disease state of the organism, the specific organism, the weight of the organism, the maturation state of the organism, and the amount and identity of the conjugate. The amount of the GPCR targeted molecule will depend on numerous factors, including, for example, the disease state of the organism, the specific organism, the weight of the organism, the maturation state of the organism, and the amount and identity of the notch influencing molecule. In some embodiments, the amount of the notch-influencing molecule in the multicomponent composition is about 0.05 to about 1000 mg/kg body weight, about 0.2 to about 500 mg/kg body weight, about 0.5 to about 200 mg/kg body weight, about 0.1 mg/kg, about 0.5 mg/kg, about 0.6 mg/kg, about 0.7 mg/kg, about 0.8 mg/kg, about 0.9 mg/kg, about 1.0 mg/kg, about 1.2 mg/kg, about 1.4 mg/kg, about 1.6 mg/kg, about 1.8 mg/kg, about 2.0 mg/kg, about 5.0 mg/kg, about 10.0 mg/kg, about 20.0 mg/kg, about 50.0 mg/kg, about 75.0 mg/kg, about 100.0 mg/kg, about 200.0 mg/kg, about 300.0 mg/kg, about 500.0 mg/kg, about 750.0 mg/kg, about 1000.0 mg/kg, about 1500.0 mg/kg, or about 2000.0 mg/kg. In regard to some conditions, the amount of the notch influencing molecule in the multicomponent composition will be about 100 mg/kg body weight. In some embodiments, the amount of the GPCR targeted molecule in the multicomponent composition is about 0.05 to about 1000 mg/kg body weight, about 0.2 to about 500 mg/kg body weight, about 0.5 to about 200 mg/kg body weight, about 0.1 mg/kg, about 0.5 mg/kg, about 0.6 mg/kg, about 0.7 mg/kg, about 0.8 mg/kg, about 0.9 mg/kg, about 1.0 mg/kg, about 1.2 mg/kg, about 1.4 mg/kg, about 1.6 mg/kg, about 1.8 mg/kg, about 2.0 mg/kg, about 5.0 mg/kg, about 10.0 mg/kg, about 20.0 mg/kg, about 50.0 mg/kg, about 75.0 mg/kg, about 100.0 mg/kg, about 200.0 mg/kg, about 300.0 mg/kg, about 500.0 mg/kg, about 750.0 mg/kg, about 1000.0 mg/kg, about 1500.0 mg/kg, or about 2000.0 mg/kg. In regard to some conditions, the amount of the GPCR targeted molecule in the multicomponent composition will be about 1 mg/kg body weight. Of course, it is possible to employ many concentrations in the methods of the present invention, and they can be adjusted in order to achieve the desired result in a given circumstance.

Some embodiments of the invention include pharmaceutical compositions. For example, pharmaceutical compositions can comprise an effective amount of the components in the multicomponent composition, therapeutic agents, or additional agents dissolved or dispersed in a pharmaceutically acceptable carrier. Aqueous compositions of the present invention can comprise an effective amount of components in the multicomponent composition, dissolved or dispersed in a pharmaceutically acceptable carrier or aqueous medium. The phrases "pharmaceutically or pharmacologically acceptable" refer to molecular entities and compositions that do not produce an adverse, allergic, or other untoward reaction when administered to an animal, or a human, as appropriate.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof. Supplementary active ingredients can also be incorporated in the compositions.

Some embodiments of the invention encompass kits that comprise the multicomponent composition. In some instances the kit comprises a concentrated or dried form of the multicomponent composition, where water, buffer, or inert product is added to the concentrated or dried (e.g., lyophilized) form to adjust the component amounts for administration. In some instances, the kit comprises separate containers, where for example, one container in the kit comprises the first component and another container in the kit comprises the second component. All or some of the components in the kit containers may be in a concentrated or dried form.

EXAMPLES

Examples and methods of use are described herein as a basis for teaching one skilled in the art to employ the invention in any appropriate manner. These examples disclosed herein are not to be interpreted as limiting.

Example Set A

Materials and Methods

Vaproic Acid (VPA) was purchased from Sigma (St. Louis, Mo.), with SBHA from Santa Cruz (Santa Cruz, Calif.). The conjugates COL-SST and CPT-SST were synthesized in our laboratories as described previously in Sun et al., Anticancer Drugs, 2007, Vol. 18, pp. 341-348 (Sun et al. 2007). The conjugate DC-53-22 was made by coupling CPT to N terminus of DTrp$^8$-SST-14 as described in Fuselier et al., Bioorg & Med Chem Lett., 2003, vol. 13, pp. 799-803. DC-50-101, an SST analog, was made as described in Rajeswaran et al., Bioorg Med Chem., 2002, Vol. 10, pp. 2023-2029.

Plasmid Constructs and Virus Packaging:

ICN1 (the Notch1 active form) were amplified by RT-PCR and inserted into retroviral vector pMSCV-GFP (pGFP). The new construct named as pICN1-GFP and vector pGFP, were co-transfected respectively with pVSV-G into a packaging cell line to achieve entire virus particles, respectively. These virus particles were measured for viral titer and transduced into HeLa cells.

Cell Culture

Human cervical cancer Hela cells from ATCC (American Type Culture Collection, Manassas, Va.) and the new established cells Hela-GFP and Hela-ICN1 were maintained in MEM medium with 10% fetal calf serum and were incubated at 37° C. in a 5% $CO_2$ atmosphere.

RT-PCR, Real-Time PCR and PCR Array

Total RNAs were isolated from tumor cells as described in the kit protocol (Invitrogen, Carlsbad, Calif.). The primers and PCR conditions for RT-PCR are shown in Table 1.

As for real-time PCR, the primers are the same as described in Table 1. Real-time PCR assays were performed on a Bio-Rad iCycler (Hercules Calif.). Assays were set up using iScript™ cDNA Synthesis Kit and iQ™ SYBR Green Supermix (Bio-Rad). The cDNA synthesis was run for one cycle of 25° C. for 5 min, 42° C. for 30 min, 85° C. for 5 min, and held at 4° C. PCR reactions were run in 10 µl reactions. Each 10 µl reaction contained 4 µl template (either cDNA, genomic or plasmid DNA), 5 µl iQ SYBR Green Supermix (BioRad), and 0.25 µM each of the corresponding forward and reverse primers. PCR was further run under the conditions below: one cycle of 95° C. for 5 min for initial denaturation and 40 cycles of 95° C. for 30 s and 56° C. (SST), 57° C. (SSTR2) for 30 s for primer annealing and product elongation. For melt curve data collection and analysis, one cycle of 95° C. for 1 min and 55° C. for 1 min was run with an increase of the temperature at a rate of 0.5° C. from 55° C. to 95° C. The experiments were done by holding at 15° C. β-actin was used as internal control. Results were calculated using the comparative $2^{-\Delta\Delta CT}$ methods as described in Livak et al., Methods, 2001, Vol. 25, pp. 402-408.

TABLE 1

Primer sequences for PCR amplification

| Receptor | Primers | PCR conditions | PCR products (bp) | Ref. or GeneBank No. |
|---|---|---|---|---|
| SST | F: 5' CCA ACCAGA CGG AGA ATG ATG C 3'<br>R: 5' TTA GGG AAG AGA GAT GGG GTG TGG3' | 40 cycles<br>(95° C., 40 s, 64° C., 30 s, 72° C., 30 s) | 243 | J00306 |
| SSTR2 | F: 5' GAG AAG AAG GTC ACC CGA ATG G 3'<br>R: 5' TTG TCC TGC TTA CTG TCA CTC CGC 3' | 40 cycles<br>(95° C., 30 s, 57° C., 30 s, 72° C., 60 s). | 290 | NM_001050 |
| Notch1 | F: 5' GGC CAC CTG GGC CGG AGC TTC 3'<br>R: 5' GCG ATC TGG GAC TGC ATG CTG 3' | 35 cycles<br>(95° C., 40 s, 65° C., 30 s, 72° C., 30 s) | 365 | Ref. 1 |
| Notch2 | F: 5' GGC CCC CTG CCC ACC ATG TAC 3'<br>R: 5' CCC GCT GAC CTC CTC CAG C 3' | 35 cycles<br>(95° C., 40 s, 65° C., 30 s, 72° C., 30 s) | 343 | Ref. 1 |
| Notch3 | F: 5' TTC TTA GAT CTT GGG GGC CT 3'<br>R: 5' GGA AGA AGG AGG TCC CAG AC 3' | 35 cycles<br>(95° C., 40 s, 58° C., 30 s, 72° C., 30 s) | 218 | Ref. 2 |

TABLE 1-continued

Primer sequences for PCR amplification

| Receptor | Primers | PCR conditions | PCR products (bp) | Ref. or GeneBank No. |
|---|---|---|---|---|
| Notch4 | F: 5' AGC AGA CAA ACT GCA GTG GA 3'<br>R: 5' CTG TTG TCC TGG GCA TCT TT 3' | 35 cycles<br>(95° C., 40 s, 55° C., 30 s, 72° C., 30 s) | 233 | NM_004557 |
| DLL1 | F: 5' AGC ACG CAC CCT GCC ACA AT 3'<br>R: 5' ACA GCC CAG CAG CAG CAT GA 3' | 35 cycles<br>(95° C., 60 s, 63.8° C., 30 s, 72° C., 60 s) | 230 | NM_005618 |
| DLL3 | F: 5' AAC AGC CCG GTG AAT GCC GA 3'<br>R: 5' ACA CAA GCC GCC GTT GAA GCA 3' | 35 cycles<br>(95° C., 60 s, 55° C., 30 s, 72° C., 60 s) | 287 | NG_008256 |
| DLL4 | F: 5' TGA TTC CTG CCG CCC AGC TT 3'<br>R: 5' TGT AAC CGC AGT GGC GCC TT 3' | 35 cycles<br>(95° C., 60 s, 63.8° C., 30 s, 72° C., 60 s) | 205 | NM_019074 |
| JAG1 | F: 5' AAC GAC CGC AAC CGC ATC GT 3'<br>R: 5' AAA GTG GGC AAC GCC CGT GT 3' | 35 cycles<br>(95° C., 60 s, 58.9° C., 30 s, 72° C., 60 s) | 195 | NM_000214 |
| JAG2 | F: 5' TGT GGT GCG GAT GGA AGC CT 3'<br>R: 5' AAT GCA AGG TGA GGC GGG CA 3' | 35 cycles<br>(95° C., 60 s, 63.8° C., 30 s, 72° C., 60 s) | 219 | NM_002226 |

Ref 1 - Primer sequence found in Talora et al. Genes & Dev., 2002, Vol. 16, pp. 22520-2263.
Ref. 2 - Primer sequence found in Bellavia et al., EMBO J., 2007, Vol. 26, pp. 1670-1680.

PCR array was performed as described in the kit instructions (SABiosciences Corporation, Frederick, Md. 21703). Firstly, total RNA was isolated from Hela cells by following the protocol of Qiagen RNeasy Mini kit (Valencia, Calif. 91355). For genomic DNA elimination, 5 μg of total RNA for 96-well plate, 2 μl 5× gDNA Elimination Buffer and RNase-free water were added to a final volume of 10 μl in a 0.5 ml tube. The Genomic DNA Elimination Mixture was mixed gently, incubated at 42° C. for 5 min, and put on ice immediately for at least 1 min. Then, the reverse transcription (RT) cocktail was prepared by adding 4 μl 5×RT Buffer, 1 μl Primer and External Control Mix, 2 μl RT Enzyme Mix, and RNase-free water to a final volume of 10 μl. For first strand RT reaction, 10 μl of RT cocktail and 10 μl of Genomic DNA Elimination Mixture were mixed together, incubated at 42° C. for exactly 15 min and the cDNA synthesis reaction was immediately stopped by heating at 95° C. for 5 min. Ninety μl of ddH2O was added to each 20 μl of cDNA synthesis reaction. The real-time PCR was performed in 96-well plate formats. A total volume 2550 μl of experimental cocktail were prepared by adding 1275 μl 2× SABiosciences RT qPCR Mater Mix, 102 μl diluted first strand cDNA synthesis reaction and 1173 μl ddH2O. Using an eight-channel pipettor, 25 μl of the experimental cocktail was added to each well of the 96-well PCR array plate. The real-time PCR detection was performed on BioRad CFX96 Real-Time System with the condition of 1 cycle (95° C. for 10 min) and 40 cycles (95° C. for 15 seconds and 60° C. for 1 min). Results were analyzed by applying the comparative $2^{-\Delta\Delta C_T}$ methods, as described above.

Western Blot

The protocol was employed as described (Santa Cruz Biotechnology, Inc., Santa Cruz, Calif. 95060). Briefly, cells were harvested, resuspended in RIPA buffer with cocktail inhibitors, homogenized by passing through 21 gauge needle, mixed with loading buffer containing fresh DTT and heated for 5 min at 95° C. Supernatants were loaded to run on 8-16% Tris-glycine gel after centrifugation at 10,000×g. Protein was transferred from gel to nitrocellulose membrane which was then blocked with 5% fat-free milk, washed and incubated respectively with Notch1 (sc-6014-R), SSTR2 (sc-11609) antibodies (Santa Cruz). The membrane was washed again and incubated with second antibody (Santa Cruz). Eventually, films were developed according to the ECL system protocol (Amersham Biosciences, England).

ELISA

SST concentration in medium and inside cells was measured by ELISA following the kit instructions (Phoenix Pharmaceuticals, Burlingame, Calif. 94010). Briefly, fifty μl of controls, prepared samples, and prepared peptide standards were added in each well of 96-well plate, respectively. Twenty-five μl of rehydrated primary antibody was added to each well. The plate was gently tapped to ensure thorough mixing and then incubated overnight at 4° C. Twenty-five μl of rehydrated biotinylated peptide was added into each well except the blank wells. The plate was incubated for 90 min at room temperature. The content of each well was discarded. The plate was washed with 350 μl of assay buffer for 4 times. To each well was added 100 μl of streptavidin-horseradish peroxidase (SA-HRP). The plate was incubated for 1 hr at room temperature, washed, and dried. One hundred μl of prepared substrate solution was added to each well, mixed well, and incubated for 15-20 min. Fluorescence will be measured using a Victor Reader (PerkinElmer, Boston, Mass.) at the wavelengths of 325/420 nm (excitation and emission).

Fluorescence Polarization (FP) cAMP Assay

The FP cAMP assay (FPA202) was performed according to the manufacturer's protocol (PerkinElmer, Boston, Mass. 02118-2512). Briefly, ten μl of forskolin at different concentrations were added to each well, then to each well ten μl of cell suspended in Stimulation Mix (made fresh before use by mixing anti-cAMP antibody in stimulation buffer) was added. Plates were incubated 30 minutes at 37° C. Twenty μl of Detection Mix (Fluo-cAMP stock diluted in Detection Buffer) was added and continued incubation 30 minutes at 37° C. Meanwhile, the standard curve, and controls were done. The cAMP was measured by Victor Reader (PerkinElmer).

Cell Proliferation Assay (MTT)

The cell proliferation assay (Promega, Madison, Wis.) was performed as described previously in Sun et al., Bioorg Med Chem Lett, 2004, Vol. 14, pp. 2041-2046. Briefly, fifty μl of medium with or without tested compounds was added to 96-well plates. Another 50 μl of tested cancer cells ($1 \times 10^5$ cells/ml) suspended in culture medium was dispensed into each well. The plates were incubated at 37° C. for 3 days. Afterward, plates were added with a 15 μl dye solution per well and incubated at 37° C. for 4 hours. To each well was then added 100 μl of the solubilization solution and the plates were incubated at 37° C. again until the contents in each well became a uniformly colored solution. The plates were measured at 570 nm by a Victor Reader (PerkinElmer).

In Vivo Tumor Growth and Treatment

After being harvested at exponential growth phase and washed 3 times with ice-cold PBS, pancreatic carcinoid BON cells, cervical cancer Hela-GFP and Hela-ICN1 cells ($4 \times 10^6$ cells/100 μl/mouse) were subcutaneously implanted in each side of the two flanks of nude mice with 5-7 weeks of age upon arrival (NCI, Frederick, Md.) as described previously as described previously in Sun et al., Drug Deliv., 2004, Vol. 11, pp. 231-238. All mice were monitored weekly. Tumor volumes were measured at 11 days post-implantation and body-weights taken once a week. Tumors were weighed and photographed when experiments were over.

Results

Generation of Hela Cells with Activated Notch1 Signaling

Figure 2:
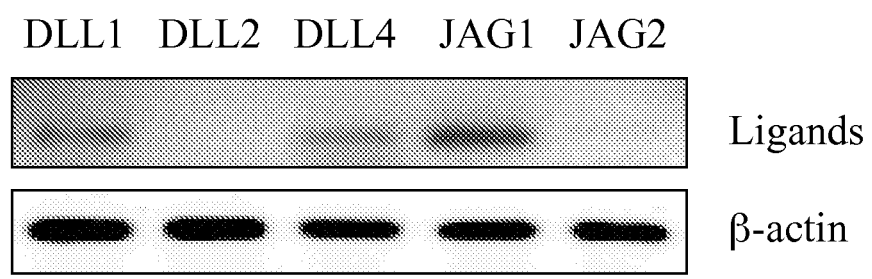
FIG. 2. RT-PCR detection for the expression of five Notch ligands in normal Hela cells. Notch ligand JAG1 is expressed.

We investigated the expression levels of Notch receptors and ligands in parental Hela cells by RT-PCR. Our results showed that receptors NOTCH1, NOTCH2, and ligand JAG1 are easily detectable, while there is little or no expression of NOTCH3, NOTCH4, DLL1, DLL2, DLL4, and JAG2 (FIGS. 1 & 2).

Figure 3:
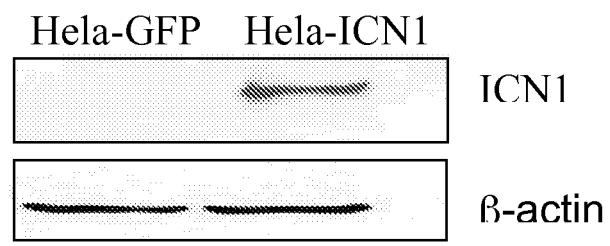
FIG. 3. Establishment of the stable cell lines Hela-ICN1 with activation of Notch1 signaling. Anti-Notch1 antibody (sc-6014-R) was used for Western blotting.

To determine the potential effects of Notch signaling on cell growth, Hela cells were transduced with retroviruses expressing the constitutively activated form of Notch1 receptor, the intracellular domain of Notch1 (ICN1) with the bis-cistronic expression of GFP as well as retroviruses that express GFP as controls. The pair of transduced cells, Hela-ICN1 and Hela-GFP, were sorted by FACS for GFP expression and confirmed for ICN1 protein expression by Western blot analysis (FIG. 3).

Activation of Notch1 Signaling Suppresses Cell Proliferation In Vitro and Tumor Growth In Vivo.

Figure 4:
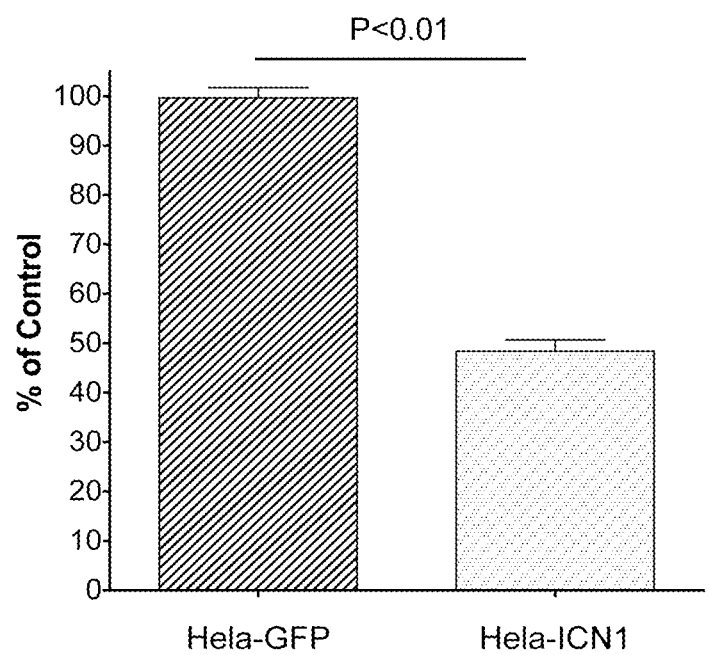
FIG. 4. Activation of Notch signaling suppressed Hela cell proliferation (Hela-ICN1) via a cell proliferation assay (MTT).
Figure 5:
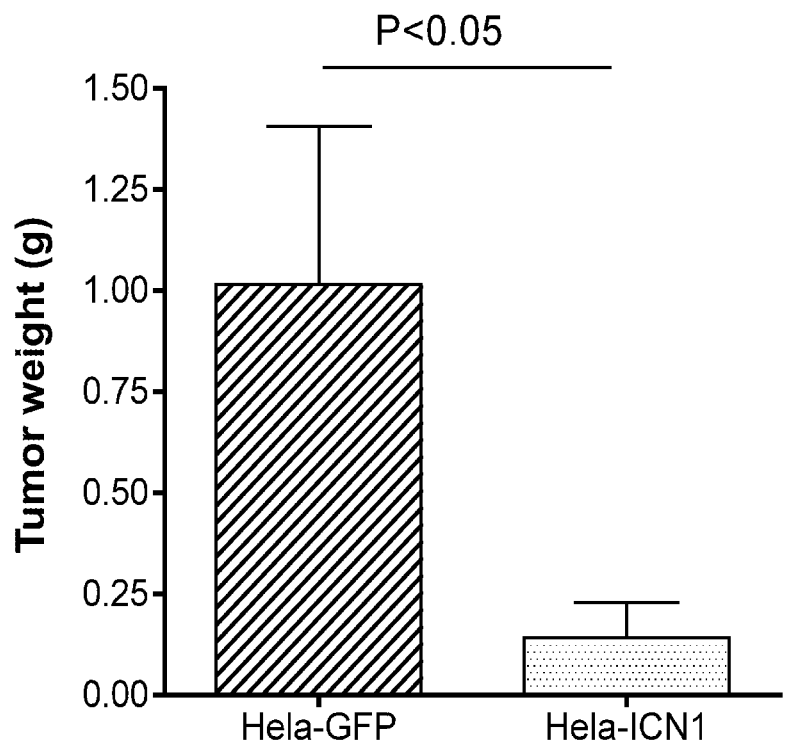
FIG. 5. The activation of Notch signaling suppressed tumor growth, via measurements of tumor weights. Hela-ICN1 tumors demonstrated lower tumor weight in vivo compared to control Hela-GFP tumors.
Figure 6:
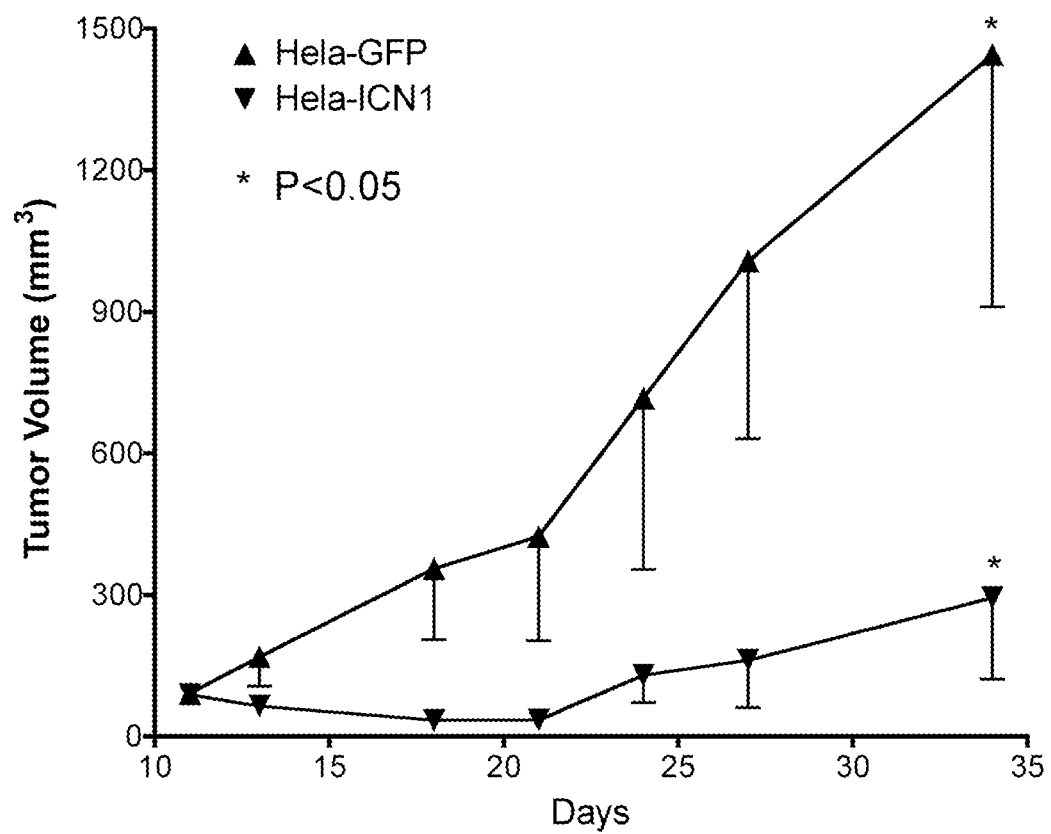
FIG. 6. Activation of Notch signaling suppressed Hela tumor growth (Hela-ICN1) via measurements of tumor growth curves.

We determined whether Notch1 signaling affects cell growth by performing in vitro cell proliferation assay (MTT assay) (FIG. 4) and in vivo tumor growth (FIGS. 5 & 6). We found that activation of Notch1 signaling resulted in over 50% inhibition (51.42%) of cell growth compared to control cells (FIG. 4). For the in vivo experiment, the results showed that activated Notch1 signaling (Hela-ICN1) significantly suppressed Hela tumor growth. At 34 days post-implantation, tumor volume in the control group (Hela-GFP) had increased from 91.27±23.46 mm$^3$ to 1445±534.6 mm$^3$ (FIG. 6). Tumor volumes in the Hela-ICN1 group increased from 88.56±11.05 mm$^3$ to 294.1±172 5 mm$^3$ at 34 days post-implantation. The inhibitory rate associated with Notch1 activation was over 80% (tumor weight: 86.18% and tumor volume: 84.82%) (FIGS. 5 & 6).

Notch1 Activation Stimulates Forskolin-Induced cAMP Accumulation

Figure 7:
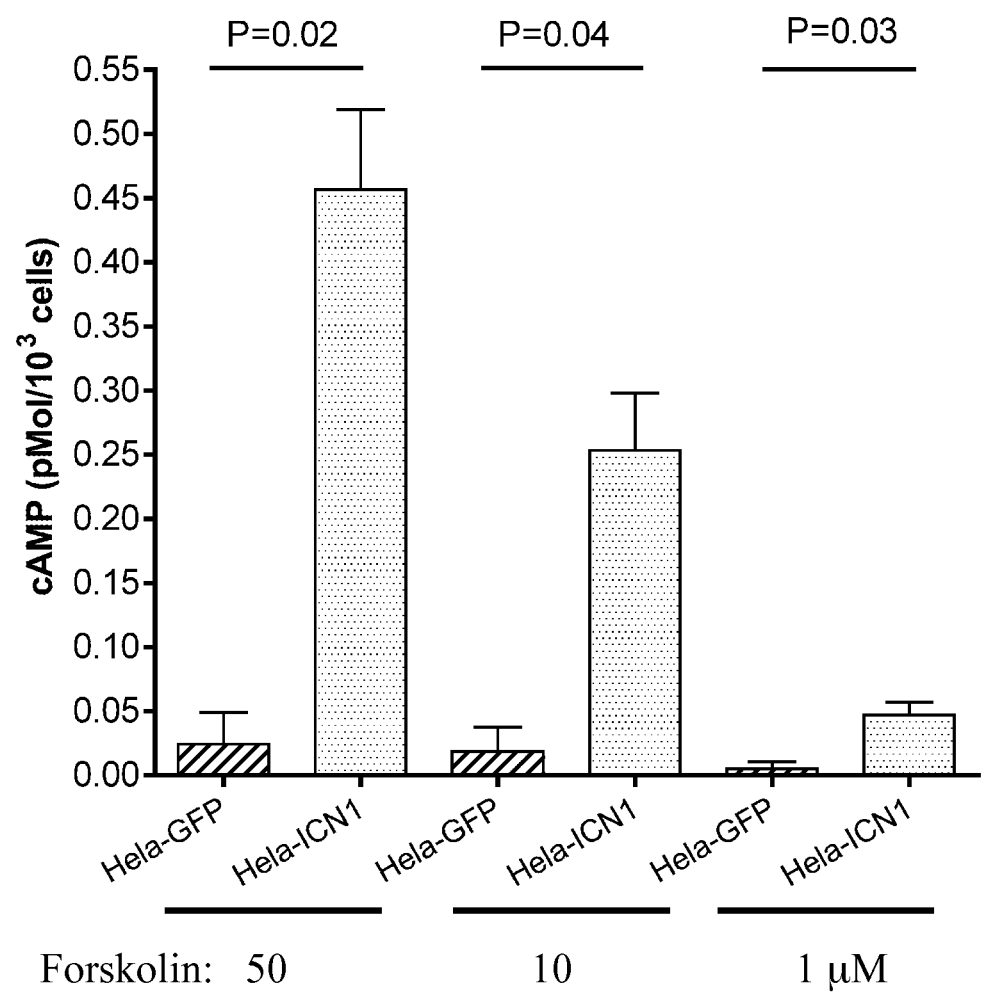
FIG. 7. The effects of Notch1 signaling activation on cAMP production. Forskolin stimulated cAMP production in both Hela-GFP and Hela-ICN1 cells, but Notch1 activation (in Hela-ICN1 cells) enhanced cAMP production, and it was dose-dependent.

G protein-coupled receptors (GPCRs) include a large family of transmembrane receptors including SSTRs. Cyclic AMP (cAMP) is a second messenger of GPCRs. To determine whether the activation of Notch1 signaling in Hela cells affects cAMP accumulation and further confirm GPCR involvement, we performed cAMP assays. Forskolin, a receptor-independent cAMP activator that stimulates cAMP production via activating adenylate cyclase, was applied for the investigation. We found that a dose-dependent forskolin-stimulated increase of cAMP production in both Hela-GFP (control) and Hela-ICN1 cells. Treatment of forskolin at 1, 10, and 50 μM resulted in the production of 0.005, 0.018, and 0.024 pMol cAMP per 10$^3$ cells in control Hela cells and 0.05, 0.25, and 0.46 pMol cAMP per 10$^3$ cells in Hela cells with activated Notch1 signaling. These data are surprising since the cAMP production stimulated by forskolin in Hela-ICN1 cells is much higher than that in the control Hela-GFP cells (FIG. 7), cAMP concentration in Hela-ICN1 cells is 10, 14, and 19-fold more than that in Hela-GFP cells when treated with forskolin at 1, 10, and 50 μM, respectively. Thus, the results suggest that activated Notch1 signaling may affect cAMP-associated signaling pathways.

Establishment of Gene Expression Profile in Hela Cells with Activation of Notch1 Signaling Based on the results above, we then tested if genes participating in the cAMP and GPCR signaling pathways might be involved in Notch1-mediated tumor suppression. We applied pathway-specific PCR arrays to profile the expression of genes involved in cAMP/Ca$^{++}$ (PAHS-066A, SABsciences), GPCR (PAHS-071A) and cancer (PAHS-033A) signaling pathways.

We found that a panel of genes that are responsive to cAMP/Ca$^{2+}$ and that contain the CRE, SRE, or SRE-like enhancer sequences in their promoters appear mediated by Notch1 activation. For example, some genes, such as SST, FOS, COX-2, PIK3R1 (PI3K p85α), THBS1, CDKN1A (p21), and COX-2, are upregulated (Table 2). Some genes such as RB1, JUNB, PCNA, STAT3, Akt (PKB), and MYC are down-regulated (Table 2). Some of these genes are involved in regulating cell functions such as DNA repair, transcription, and cell cycle. Furthermore, we found that only three (SSTR2, ADRB2, and AGTR2) out of 41 tested GPCR genes were significantly upregulated in Hela-ICN1 cells. Thus SST and SSTR2 appear to be involved in Notch1-mediated pathways.

TABLE 2

Effects of Notch signaling on gene expression by real-time PCR.

| Symbol | Description | Fold (ICN:GFP) Δ |
|---|---|---|
| *Up-regulated genes* | | |
| ANGPT1 | Angiopoietin 1 | 8.98 ± 2.78 ↑ |
| ANGPT2 | Angiopoietin 2 | 7.25 ± 1.33 ↑ |
| CDKN1A | Cyclin-dependent kinase inhibitor 1A (p21) | 7.36 ± 1.79 ↑ |
| COX-2 | Prostaglandin-endoperoxide synthase 2 (Cyclooxygenase) | 11.56 ± 1.58 ↑ |
| COL1A1 | Collagen, type I, alpha 1 | 11.61 ± 3.67 ↑ |
| CTGF | Connective tissue growth factor | 3.64 ± 0.32 ↑ |
| FOS | V-fos FBJ murine osteosarcoma viral oncogene homolog | 3.90 ± 0.52 ↑ |
| IL1R1 | Interleukin 1 receptor, type I | 22.23 ± 1.26 ↑ |
| ITGA1 | Integrin alpha 1 | 10.13 ± 1.40 ↑ |
| ITGA4 | Integrin alpha 4 | 8.56 ± 0.40 ↑ |
| ITGAV | Integrin alpha V | 89.86 ± 37.95 ↑ |
| ITGB3 | Integrin beta 3 | 91.77 ± 64.86 ↑ |
| MMP2 | Matrix metallopeptidase 2 | 49.33 ± 16.12 ↑ |
| MMP9 | Matrix metallopeptidase 9 | 7.25 ± 1.33 ↑ |
| MTSS1 | Metastasis suppressor 1 | 6.26 ± 1.68 ↑ |
| PI3KR1 | PI3K p85alpha | 9.30 ± 3.20 ↑ |
| S100A4 | S100 Ca binding protein A4 (relevant to tumor metastasis) | 4.82 ± 0.40 ↑ |
| SOCS1 | Suppressor of cytokine signaling 1 | 3.6 ± 0.02 ↑ |
| Serpine1 | Serpin peptidase inhibitor, clade E | 27.43 ± 9.2 ↑ |
| SST | Somatostatin (SST) | 2229.4 ± 164 ↑ |
| SSTR2 | SST receptor type II | 20.77 ± 3.46 ↑ |
| TWIST1 | Twist homolog 1 (*Drosophila*) | 12.38 ± 3.44 ↑ |
| THBS1 | Thrombospondin 1 | 73.77 ± 18.12 ↑ |
| *Down-regulated genes* | | |
| AKT1 | Vakt murine thymoma viral oncogene homolog 1 (AKT/PKB) | −4.06 ± 0.63 ↓ |
| E6/E7 | Human papillomavirus type 18 proteins E6 and E7 | −10.38 ± 4.58 ↓ |
| JUNB | Jun B proto-oncogene (AP-1) | −3.88 ± 0.77 ↓ |
| MAP2K1 | Mitogen-activated protein kinase kinase 1 (MAPKK1/MEK1) | −3.90 ± 1.68 ↓ |
| MYC | V-myc myelocytomatosis viral oncogene homolog | −3.61 ± 1.20 ↓ |
| PCNA | Proliferating cell nuclear antigen | −2.16 ± 0.02 ↓ |
| STAT3 | Signal transducer and activator of transcription 3 | −3.58 ± 0.88 ↓ |
| *Genes with no obvious change* | | |
| BRCA1 | Breast cancer 1, early onset | −1.47 ± 0.08 → |
| p53 | Tumor protein 53, a tumor suppressor | 1.48 ± 0.32 → |
| NFκB | Nuclear transcription factor | 1.60 ± 0.24 → |

We performed PCR arrays of genes associated with cancer signaling pathways (PAHS-033A). Some genes (these genes in the gene panel covered by cancer pathway PCR array) related to apoptosis, proliferation, cell cycle, signal transduction, and transcription factors were up-regulated (such as integrin alpha1, integrin alpha4, MMP2, MMP9, TWIST1) or down-regulated (such as MAP2K, RB1, E6/E7) in Hela-ICN1 besides the genes mentioned above (Table 2). However, the expression of certain genes such as p53, NFκB, BRCA1, had no obvious change. These data suggest that Notch1-mediated tumor suppression may be mediated through the signaling pathway cascade involving with the components of the cAMP/Ca$^{++}$, GPCR, and cancer signaling pathways.

Confirmation of the Upregulation of SST and SSTR2 Via Notch1 Signaling Activation To confirm the expression of SST and SSTR2 in Notch1-activated HeLa-ICN1 cells, we performed real-time PCR, ELISA, and western blot analysis.

Figure 8:
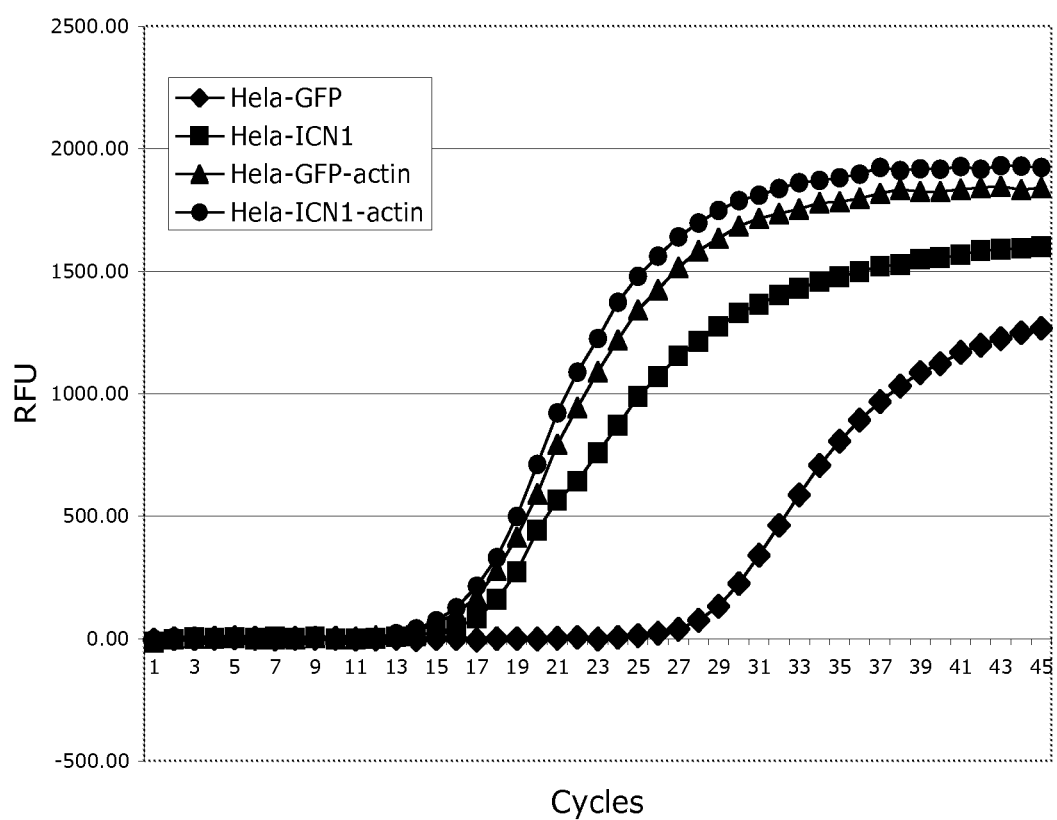
FIG. 8. Up-regulation of SST expression in Notch-activated Hela-ICN1 cells at the mRNA level using real-time PCR. SST in Hela-ICN1 cells increased over 2200-fold than that in Hela-GFP cells.
Figure 9:
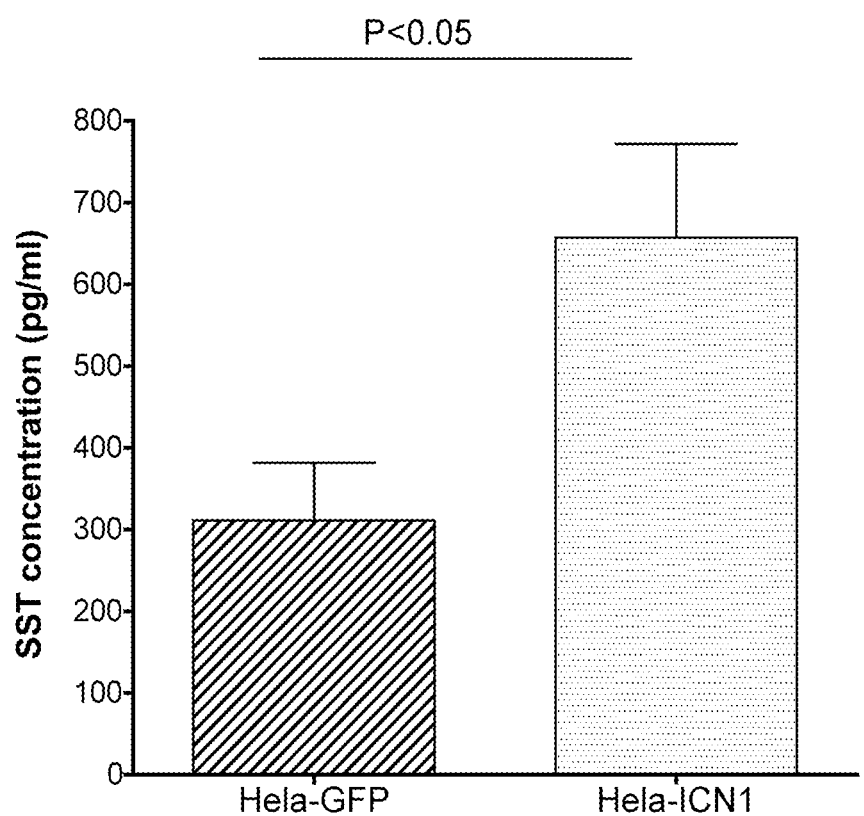
FIG. 9. An increase of SST at the protein level in the culture medium from Notch-activated Hela-ICN1 cells compared to control Hela-GFP cells using ELISA.

As for SST expression, our results showed that activated Notch1 signaling increased SST transcription at the mRNA level with over 2200-fold higher in Hela-ICN1 than that in Hela-GFP (FIG. 8 and Table 2). We further did ELISA analysis and found an increase of SST at the protein level, showing the same trend as the real-time PCR results. SST concentration was over 2-fold higher in Hela-ICN1 culture medium (657 pg/ml) than that of Hela-GFP (311 pg/ml) (FIG. 9), but it was undetectable in cells.

Figure 10:
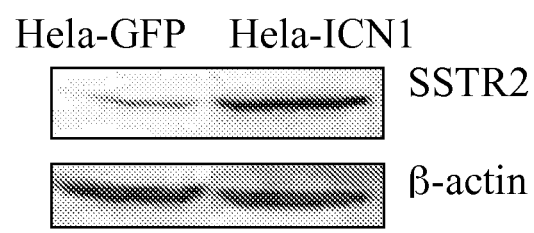
FIG. 10. SSTR2 expression increased in Notch-activated Hela-ICN1 cells using western blot.
Figure 11:
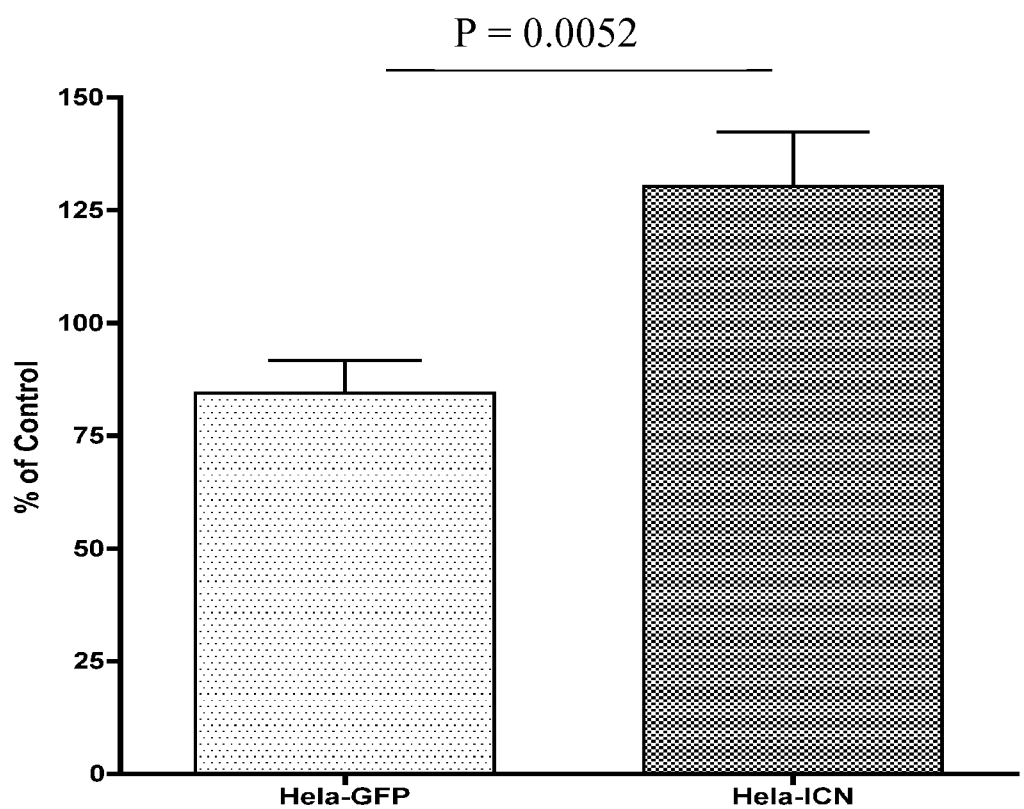
FIG. 11. A receptor-binding assay demonstrated the increase of SSTR2 density via Notch1 activation in Hela-ICN1.

As for SSTR2 expression, we found a 21-fold higher amount of SSTR2 expression at the mRNA level and over 70% higher of SSTR protein at the protein level in Hela-ICN1 cells than that in Hela-GFP cells (Table 2 and FIG. 10), Moreover, our further binding assay (as described in Sun et al., Clinical Medicine: Oncology, 2008, Vol. 2, pp. 1-9) displayed an over 10% increase of SSTR density on Hela-ICN1 cell surfaces compared to Hela-GFP cells (FIG. 11).

Figure 12:
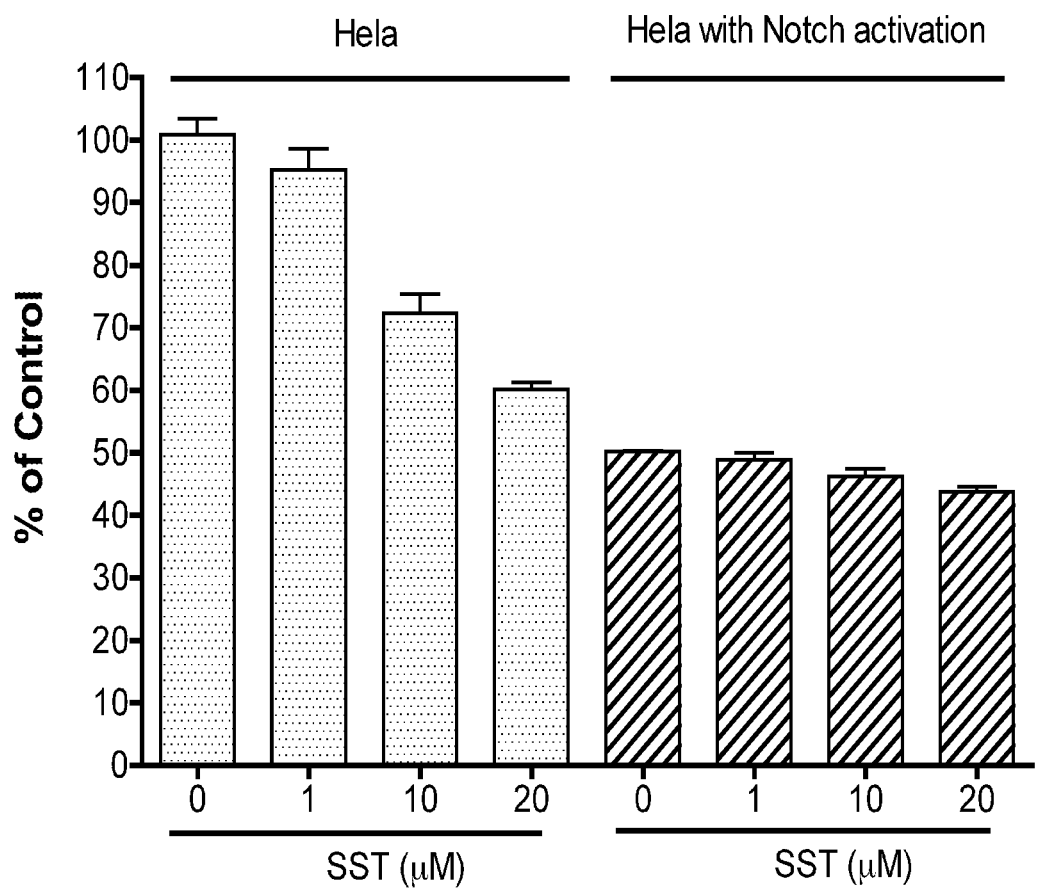
FIG. 12. Native SST-14 suppressed Hela-GFP cell proliferation in a dose-dependent way, resulting in about 40% inhibitory rate at 20 μM. SST-14 enhanced the suppression of Notch1-activated Hela-ICN1 cell growth, resulting in 12% inhibition at 20 μM.

FIG. 12 shows that SST-14 suppresses Hela-GFP ("Hela" in FIG. 12) cell proliferation in a dose-dependent way, resulting in about 40% inhibitory rate at 20 μM. SST-14 enhances the growth suppression of Hela-ICN1 cells in which Notch1 signaling was activated, further resulting in 12% inhibition at 20 μM, but with less impact on Hela-ICN1 cells. This indicates that overexpression of ICN1 may result in a greater amount of SST being produced via Notch-activated SST gene expression (FIG. 12).

Example Set B

Materials and Methods

Unless otherwise provided below, all materials and methods are the same as those provided in Example Set A.

RT-PCR and Real-Time PCR

For real-time PCR, the primers are the same as described in Table 1 except SSTR1 primers (Forward: 5' ATC TGC TGG ATG CCT TTC TAC G 3', Reverse: 5' CAG GTG CCA TTA CGG AAG ACG 3') and SSTR2 primers (Forward: 5' GAG AAG AAG GTC ACC CGA ATG G 3', Reverse: 5' TTG TCC TGC TTA CTG TCA CTC CGC 3'). Real-time PCR assays were performed as before. Assays were set up using iScript™ cDNA Synthesis Kit and iQ™ SYBR Green Supermix (Bio-Rad). The cDNA synthesis was run for one cycle of 25° C. for 5 min, 42° C. for 30 min, 85° C. for 5 min, and held at 4° C. PCR reactions were run in 20 μl reactions. Each reaction contained 1 μl cDNA, 10 μl iQ SYBR Green Supermix (Bio-Rad) and 1 μl each of the corresponding forward and reverse primers. PCR was further run under the conditions below: one cycle of 95° C. for 5 min for initial denaturation and 40 cycles of 95° C. for 30 s and 58° C. (SSTR1), 57° C. (SSTR2), 65° C. (SSTR3 and SSTR5), 60° C. (SSTR4), and 56° C. (SST) for 30 s for primer annealing and product elongation. β-actin was used as internal control. Results were calculated applying the comparative $2^{-\Delta\Delta CT}$ methods as described above.

Cell Colony Formation Assay

Two hundred Hela-GFP and Hela-ICN1 cells were added in each well of 6-well plate, respectively. The plates were continuously incubated for 7-8 days until cell colonies were visible. Colonies were fixed with 100% methanol at room temperature for 15 min and washed with PBS. Colonies were further stained with 0.1% crystal violet at room temperature for 1 hr, rinsed with water, and photographed after air-dry.

Cell Cycle Analysis

Cell cycle analysis was analyzed by flow cytometry. Cells ($2\times10^6$) were harvested, washed with PBS and fixed in 70% of ethanol overnight at −20° C. Cells after centrifuge (5 min, 200×g) were re-suspended in 5 ml PBS, incubated for 60 sec and centrifuged for 5 min at 200×g. Cell pellets were suspended in 1 ml of PBS with 0.1% Triton-100, 20 μg propidium iodide (PI) (Sigma p4864), and 200 μg DNase-free RNase A (Sigma R6513). They were kept for 1 hour at room temperature, and sent to Tulane Cancer Center for flow cytometry analysis.

Results

Activation of Notch1 Signaling Induces Anti-Cell Proliferation

Figure 13:
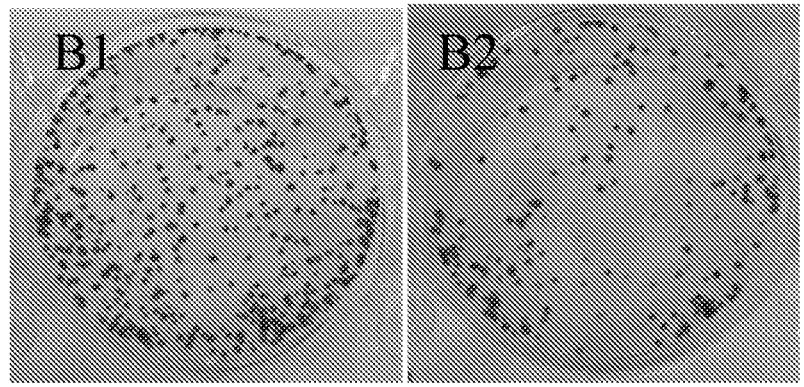
FIG. 13. Notch activation suppressed the formation of cervical cancer Hela cell colonies. Panel B1 shows Hela-GFP colonies. Panel B2 shows Hela-ICN colonies, which exhibited activated Notch signaling. Hela-ICN demonstrated lower cell proliferation than the Hela-GFP control cell colony.

MTT assays showed that Notch1 activation suppressed Hela cell (Hela-ICN1) proliferation, with an average inhibitory rate 46% (Table 3). Cell colony formation assay showed that Notch1 signaling reduced colony formation (FIG. 13). The proliferation markers PCNA and p21 were found to be regulated via Notch1 activation. The change is identical as Notch1's anti-proliferation function. PCNA were downregulated but p21 was upregulated via Notch1 activation (Table 2).

Activation of Notch1 Signaling Induces Apoptosis and Cell Cycle Arrest

Figure 14:
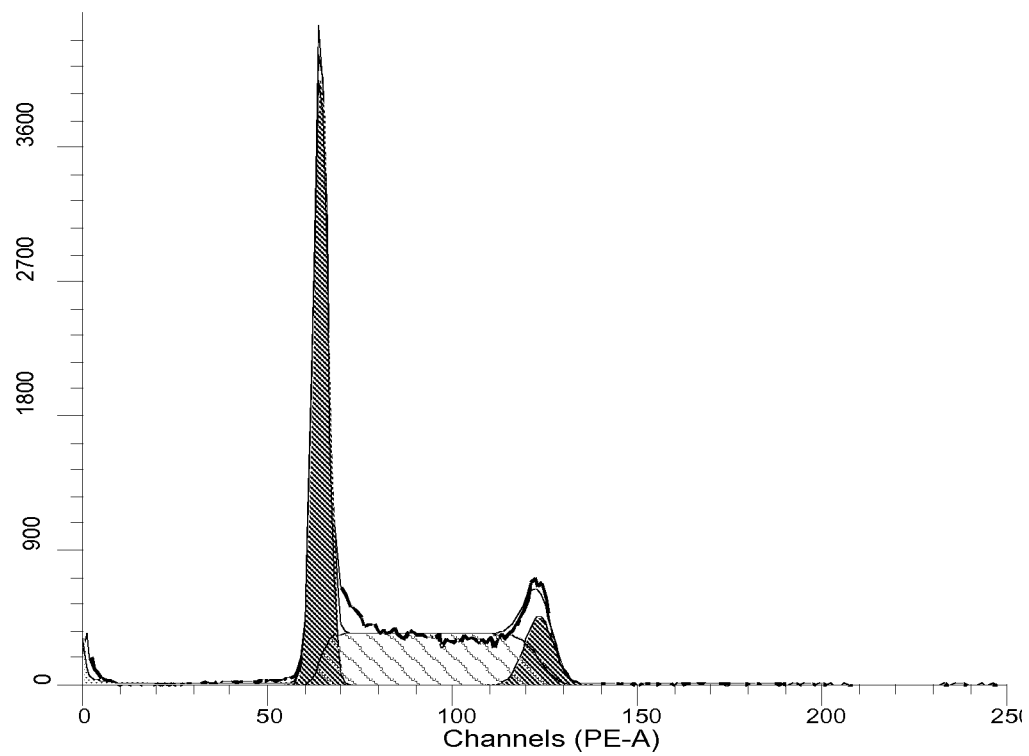
FIG. 14. The Hela-GFP control did not demonstrate apoptosis.
Figure 15:
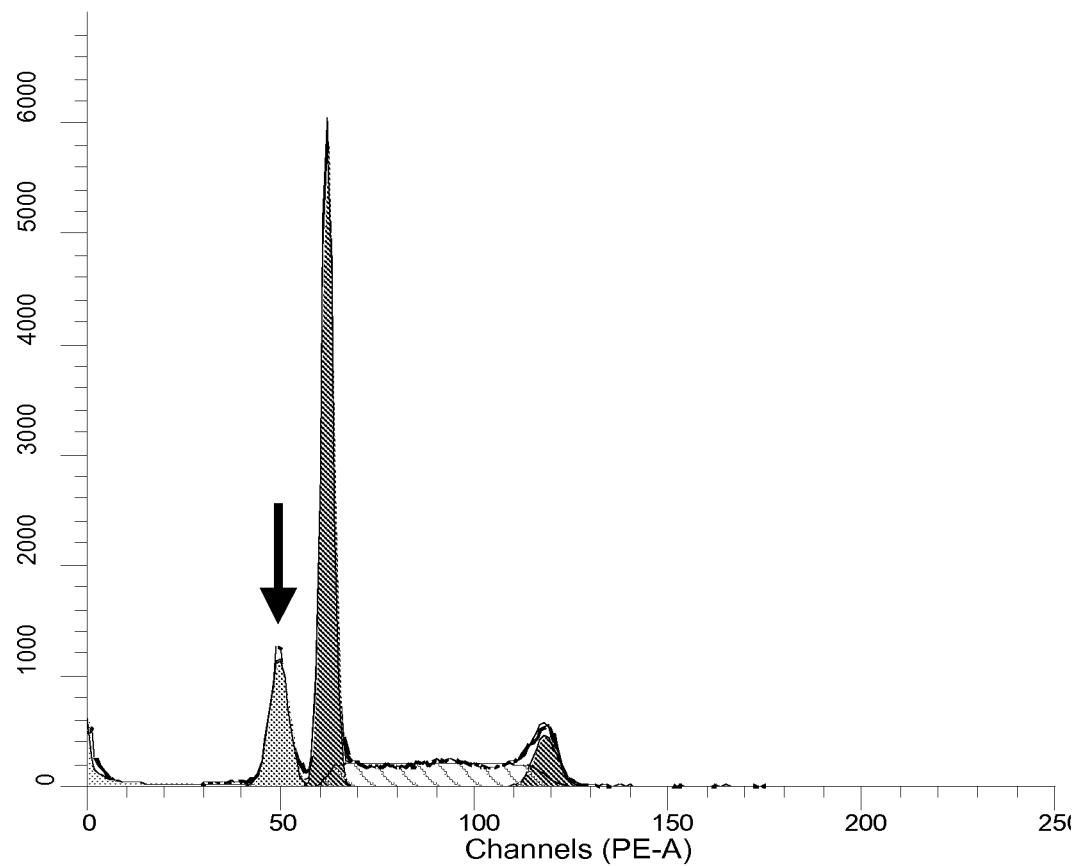
FIG. 15. The Hela-ICN cells, in which the arrow shows apoptosis. These results, compared with the control Hela-GFP shown in FIG. 14, demonstrate that activating Notch signaling induced tumor cell apoptosis.

Both Hela-GFP and Hela-ICN1 cells were analyzed for apoptosis and cell cycle by FACS. The results in Table 3, FIG. 14, and FIG. 15 showed that activated Notch1 signaling resulted in cell cycle arrest at phase S during which DNA damage often takes place, and induced 16% of cell apoptosis (FIG. 15). The expression of cell cycle and apoptotic markers were assessed. Anti-apoptotic BCL-2 was downregulated, but cell cycle marker p21 was upregulated in Hela-ICN1 cells, with no obvious change of p53, MDM2 expression. P21 is a cyclin-dependent kinase inhibitor which is induced by both p53-dependent and -independent mechanisms. Induction of p21 may cause cell cycle arrest.

TABLE 3

Cell cycle analysis on Hela-ICN cells with Notch1 activation.

| Compounds | Hela-GFP (%) | Hela-ICN1 (%) |
|---|---|---|
| Cell cycle progression | | |
| G0/G1 | 61.88 ± 3.13 | 49.67 ± 8.90 |

TABLE 3-continued

Cell cycle analysis on Hela-ICN cells with Notch1 activation.

| Compounds | Hela-GFP (%) | Hela-ICN1 (%) |
|---|---|---|
| S | 31.35 ± 2.43 | 41.05 ± 4.56 |
| G2/M | 6.77 ± 0.93 | 9.27 ± 0.78 |
| Apoptosis | | 16.84 ± 6.10 |
| Proliferation | 97.10 ± 1.35 | 53.96 ± 2.76 |

Notch Stimulators Suppress Cell Growth and Induce SST Signaling

Figure 16:
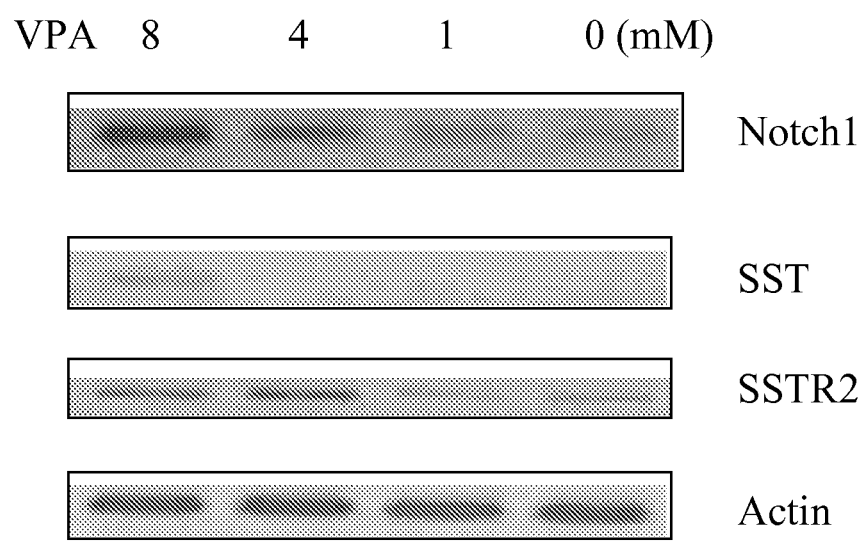
FIG. 16. The effects of different concentrations of Notch stimulator VPA on Notch1, SST, and SSTR2 expression in cervical cancer Hela cells, with beta-actin as control. VPA activated expression of Notch1, SST, and SSTR2.
Figure 17:
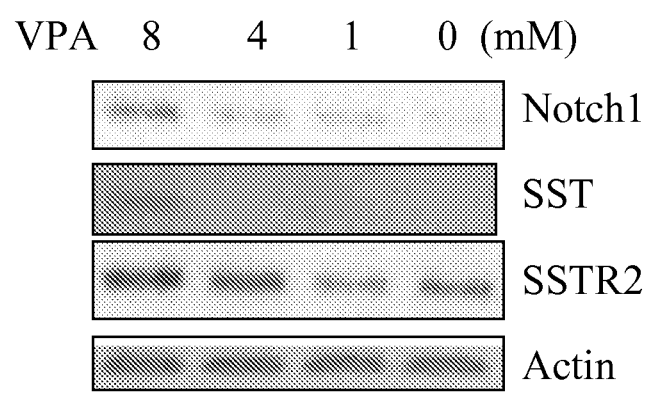
FIG. 17. The effects of different concentrations of VPA on Notch1, SST, and SSTR2 expression in pancreatic carcinoid BON cells, with beta-actin as control. VPA activated expression of Notch1, SST, and SSTR2 in BON cells.
Figure 18:
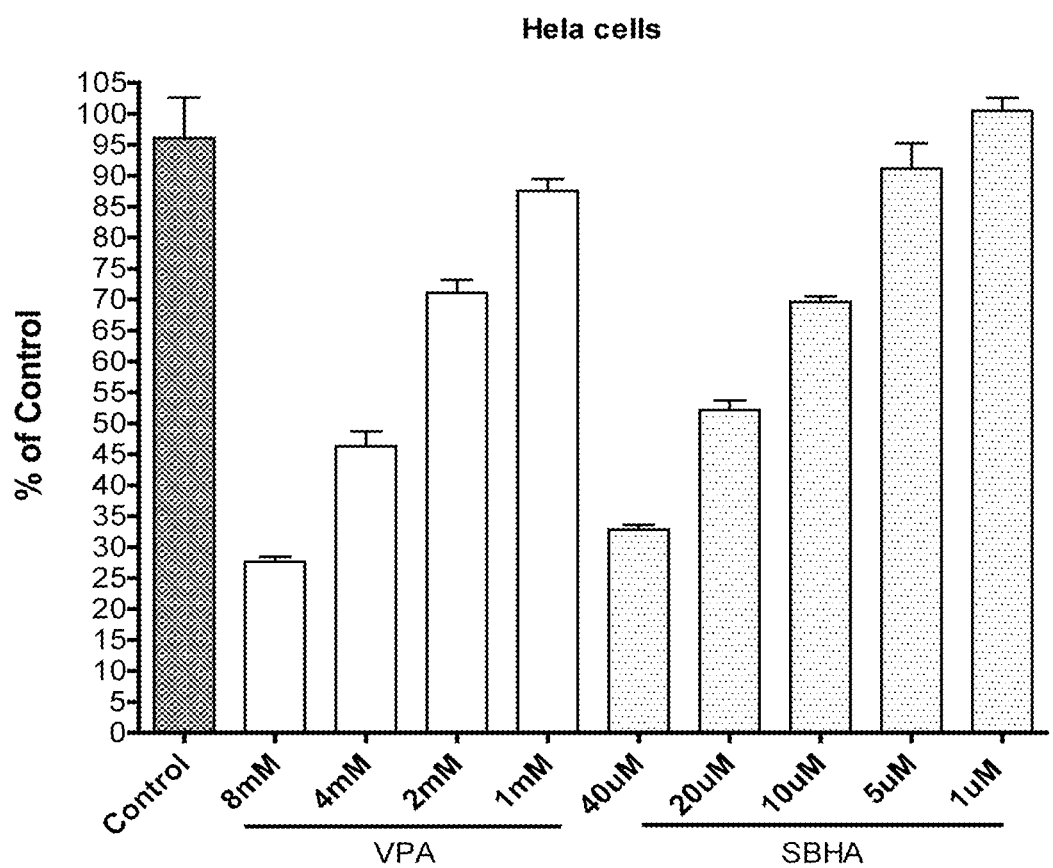
FIG. 18. Small molecule Notch stimulators VPA and SBHA suppressed cervical cancer Hela cell growth.
Figure 19:
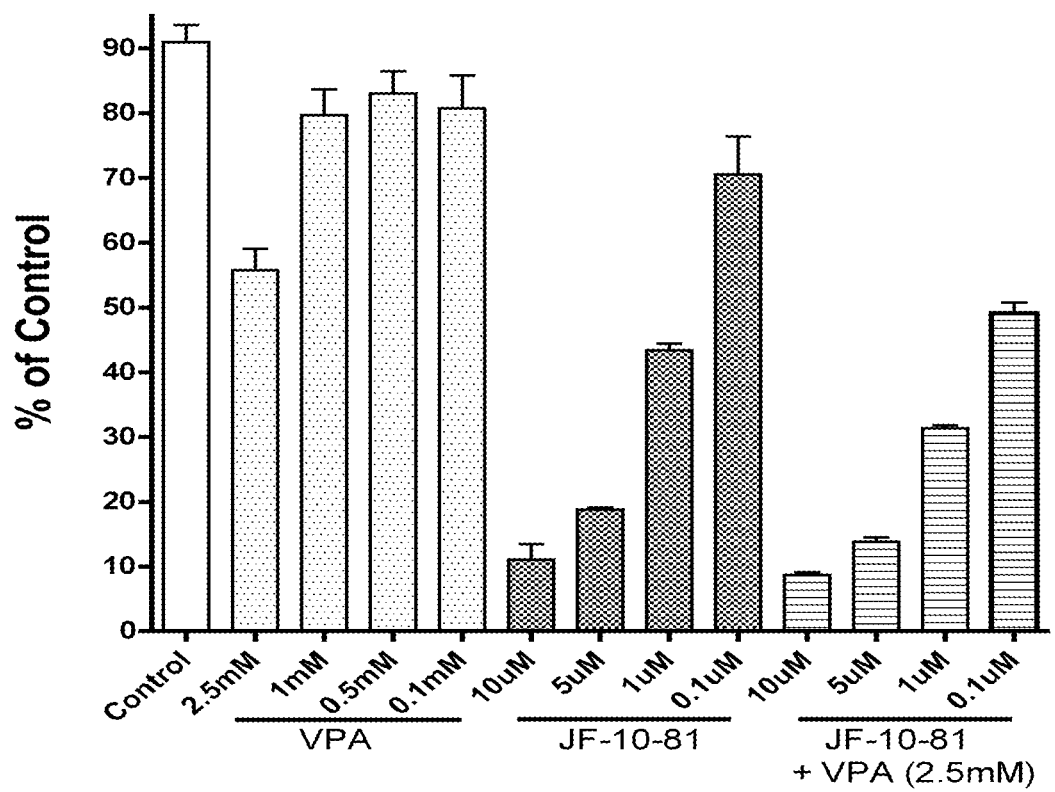
FIG. 19. The result of combination therapy of VPA and the CPT-SST conjugate (JF-10-81) to cervical cancer Hela cell growth. As seen, 2.5 mM VPA enhanced the suppression of the CPT-SST conjugate (JF-10-81) on Hela cell growth.
Figure 20:
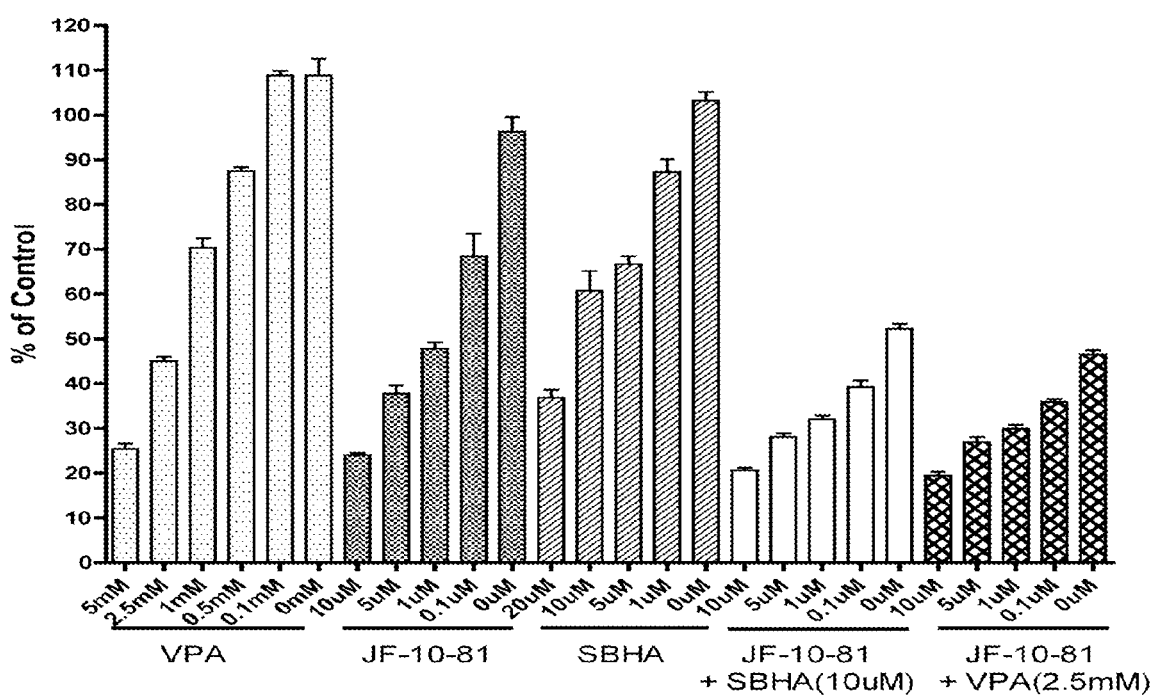
FIG. 20. The result of combination therapy of VPA/SBHA and the CPT-SST conjugate (JF-10-81) to pancreatic carcinoid BON cell growth. 2.5 mM VPA or 10 uM SBHA enhanced the suppression of the CPT-SST conjugate (JF-10-81) on BON cell growth.
Figure 21:
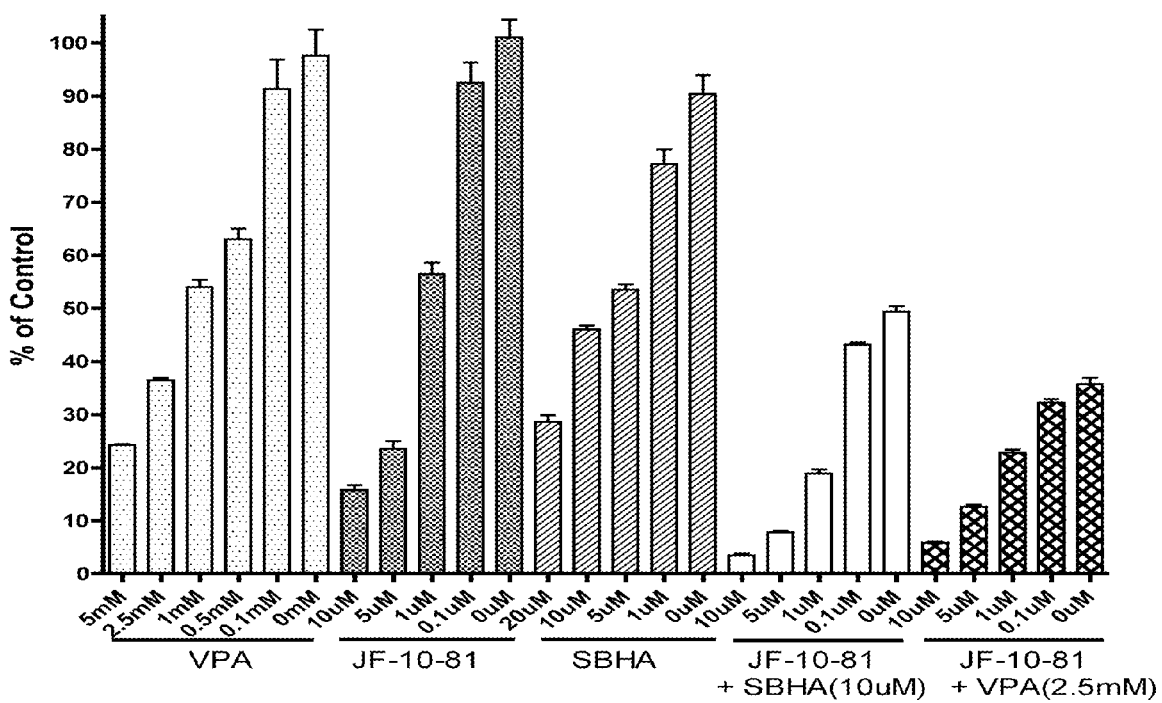
FIG. 21. The result of combination therapy of VPA/SBHA and the CPT-SST conjugate (JF-10-81) to lung cancer DMS-53 cell growth. 2.5 mM VPA or 10 uM SBHA enhanced the suppression of the CPT-SST conjugate (JF-10-81) on DMS-53 cell growth.
Figure 22:
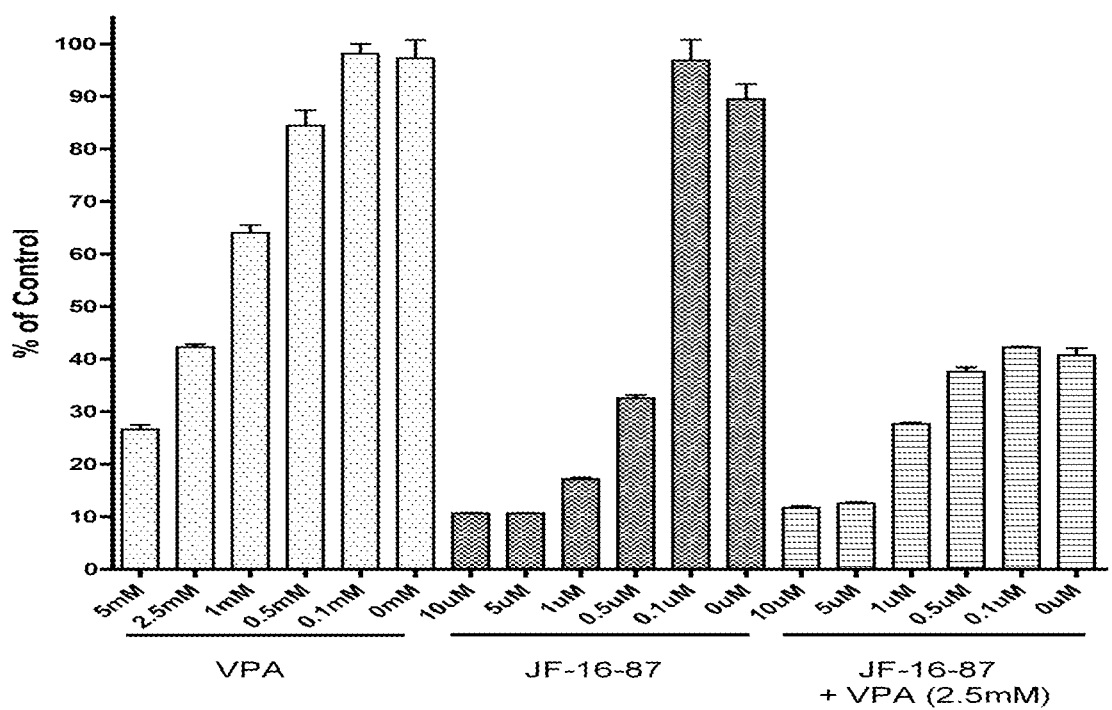
FIG. 22. The result of combination therapy of VPA and the colchicine-SST conjugate (JF-16-87) to cervical cancer Hela cell growth. 2.5 mM VPA enhanced the suppression of the colchicine-SST conjugate (JF-16-87) on Hela cell growth.
Figure 23:
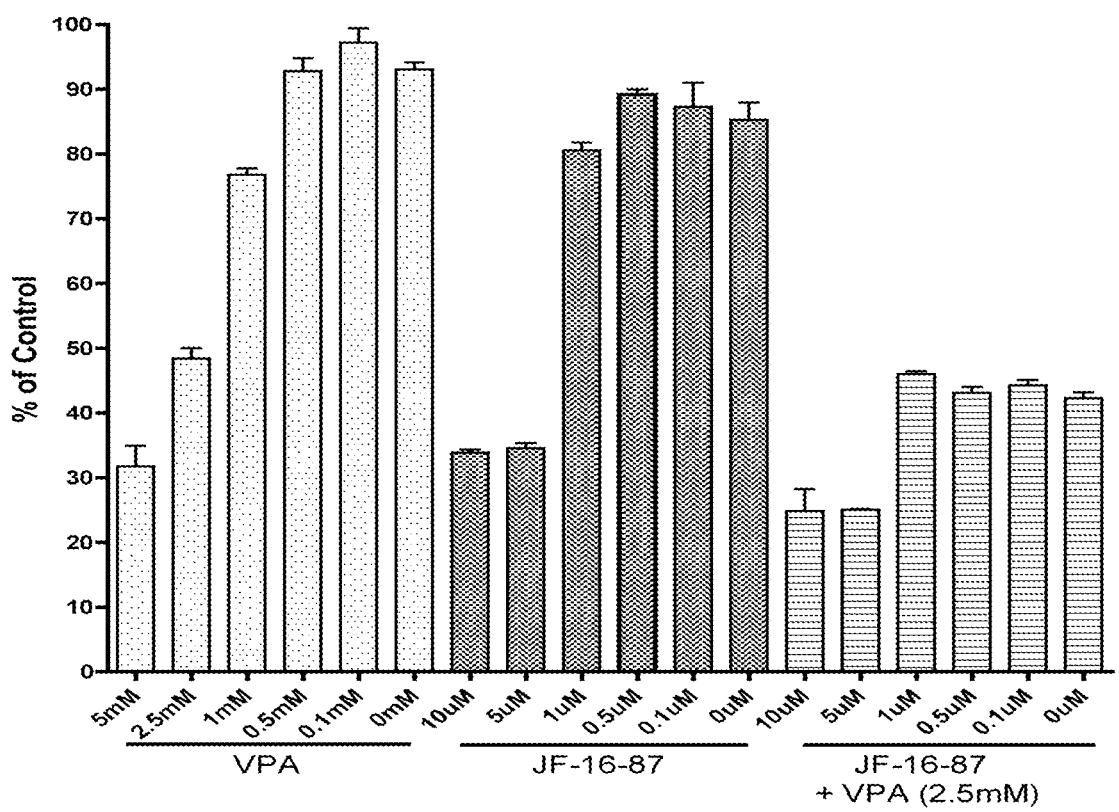
FIG. 23. The result of combination therapy of VPA and the colchicine-SST conjugate (JF-16-87) to pancreatic carcinoid BON cell growth. 2.5 mM VPA enhanced the suppression of the colchicine-SST conjugate (JF-16-87) on BON cell growth.

Notch stimulator VPA was found to induce the expression of Notch1, SST, and VPA-mediated increase of Notch1, SST, and SSTR2 in cervical cancer Hela cells and pancreatic carcinoid BON cells (FIGS. 16 and 17). Using MTT assays, VPA also displayed growth inhibition to Hela cells, BON cells, and small cell lung cancer DMS53 cells (FIGS. 18, 19, 20, 21, 22, 23, and 24). Another Notch stimulator SBHA also displayed its anti-proliferation ability by MTT assays (FIGS. 18, 20, and 21)

Activation of Notch1 Signaling May be Involved in Epithelial-Mesenchymal Transition (EMT).

Figure 25:
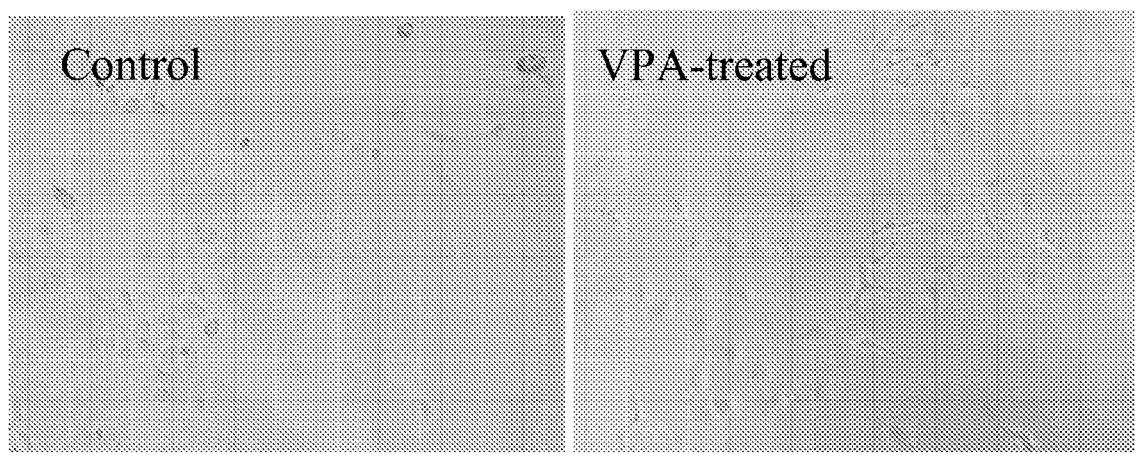
FIG. 25. The morphological change of Hela cells after treatment with VPA at 8 mM, indicating possible epithelial-mesenchymal transition (EMT).

We also observed that cell morphology changed via VPA-induced Notch1 activation (FIG. 25). The expression of some epithelial specific markers such as E-cadherin, β-catenin and mesenchymal markers such as vimentin, N-cadherin, MMP-2, fibronectin were investigated in Hela cells after Notch1 activation. The transcription factors twist (a known mediator of mesodermal tissue development), snail and slug were also detected in Notch1-activated Hela-ICN1 cells. Snail and slug promote EMT. Slug, snail, and twist are transcription factors that regulate the expression of tumor suppressors such as E-cadherin. We found E-cadherin was down regulated. Snail, slug, and twist were up-regulated via Notch1 activation. However, there was no obvious change of the expression of β-catenin, vimentin, N-cadherin, and fibronectin. These findings suggest that Notch1 activation may promote EMT.

Notch-Mediated Upregulation of SST and SSTRs

Figure 26:
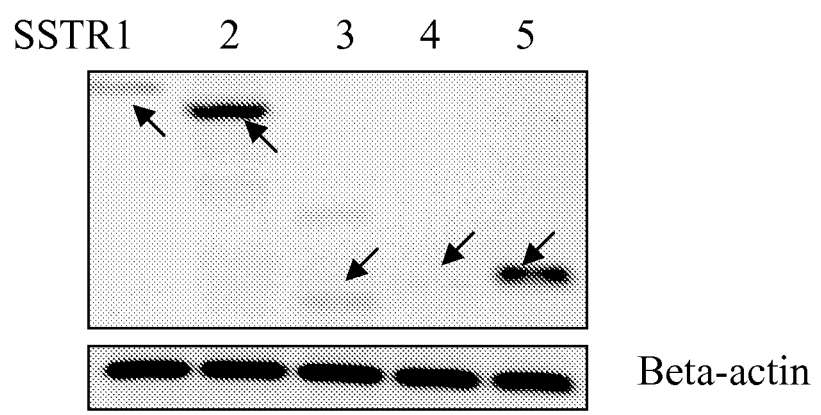
FIG. 26. The expression of SSTR subtypes in native Hela cells. There were abundant SSTR2 and SSTR5, with less SSTR1, and no or trace SSTR3 and SSTR4.
Figure 27:
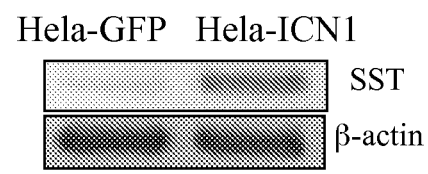
FIG. 27. Activation of Notch signaling (Hela-ICN1) up-regulated the expression of SST. There was no expression or trace expression of SST in Hela-GFP control.
Figure 28:
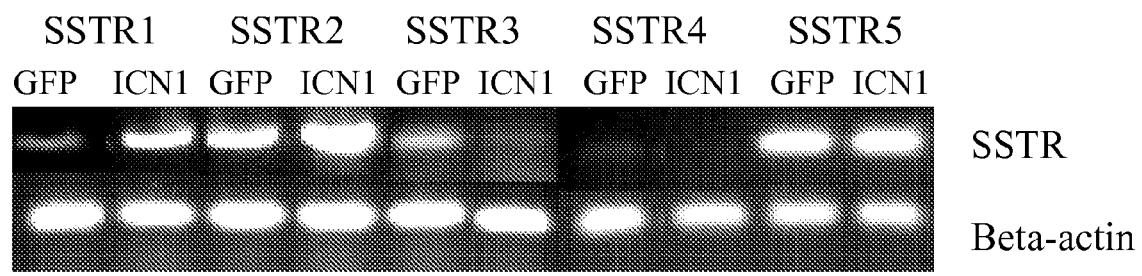
FIG. 28. Activation of Notch signaling in Hela-ICN1 cells induced up-regulation of SSTR1 and SSTR2, down-regulation of SSTR3, and provided no change of SSTR4 and SSTR5. GFP represents Hela-GFP, and ICN1 represents Hela-ICN1.

RT-PCR and real-time PCR were used to investigate the expression of SST and all 5 SSTR subtypes in HeLa-GFP and HeLa-ICN1 cells. Firstly, we investigated the background of SST and all SSTRs in Hela cells. We found that SSTR2 and SSTR5 are highly expressed in native Hela cells, with less expression of SSTR1 and SSTR3, and no or trace expression of SSTR4 (FIG. 26). The results from RT-PCR showed an increase in the expression of SST (FIG. 27), SSTR1 and SSTR2; SSTR3 showed a decrease in expression and no obvious change of SSTR4 and SSTR5 (FIG. 28) in Hela-ICN1 cells. Further, using real-time PCR, we found a similar trend in the increase in SST, SSTR1, and SSTR2 as in RT-PCR. Activated Notch signaling activated SST transcription with over 2200-fold higher in Hela-ICN1 than in Hela-GFP (FIGS. 8 & 10), and with an increase of SSTR1 (16 fold) and SSTR2 (21 fold), with decrease of SSTR3 (4 fold) and no obvious change of SSTR4 and SSTR5 (less than 2 fold). These data suggest that inhibition of Notch signaling in Hela tumor growth might correlate with the activation of SST and SSTR1/2.

Anti-Cell Proliferation of SST and SST Conjugates

We performed cell proliferation assays by treating Hela cells with SST-14 at different concentrations (20, 10, and 1 μM) and found that SST-14 inhibited Hela cell proliferation in a dose-dependent fashion; 40% inhibition at 20 μM, and 28% inhibition at 10 μM, but almost no effect at 1 μM. SST treatment in Hela-ICN1 cells showed limited inhibition as observed in Hela-GFP cells. The inhibition rates of SST to Hela-ICN1 cells at 20, 10, and 1 μM were 12, 8, and 2%, respectively, less than that in Hela-GFP cells (FIG. 12).

Reversals of SST Knockdown on Notch1-Induced Decrease of BCL-2 Gene Expression

Figure 29:
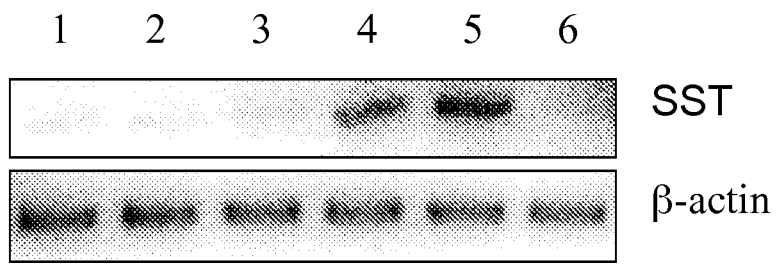
FIG. 29. SST knockdown via SST siRNA. Hela-ICN1 cells over-expressing SST were treated with SST siRNA at 5 μl (lane 1), 15 μl (lane 2), 30 μl (lane 3), Control siRNA at 15 μl (lane 4). Lane 5 and lane 6 are control Hela-ICN1 and Hela-GFP cells, respectively.
Figure 30:
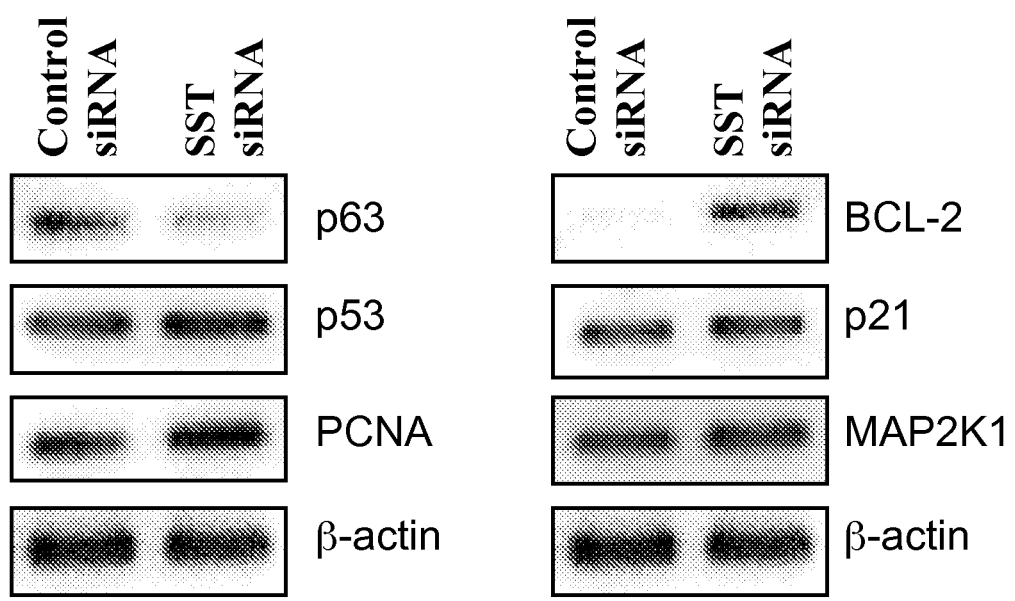
FIG. 30. The effects of SST knockdown on the expression of certain genes in Hela-ICN1 cells via SST siRNA. The knockdown of anti-apoptosis gene BCL-2 via Notch1 activation was reversed via SST siRNA, suggesting Notch1-mediated apoptosis is through SST signaling pathway. Control siRNA (15 μl), SST siRNA (15 μl).

Notch1 activation decreased the expression of anti-apoptotic BCL-2. SST siRNA transfected into the above Notch1-activated cells knocked down SST (FIG. 29) and recovered BCL-2 decreased by Notch1 activation (FIG. 30). These findings suggest that SST signaling is involved in Notch1-induced Hela cell apoptosis.

Application of SST Signaling Activation in the Combination Cancer Therapy

Figure 31:
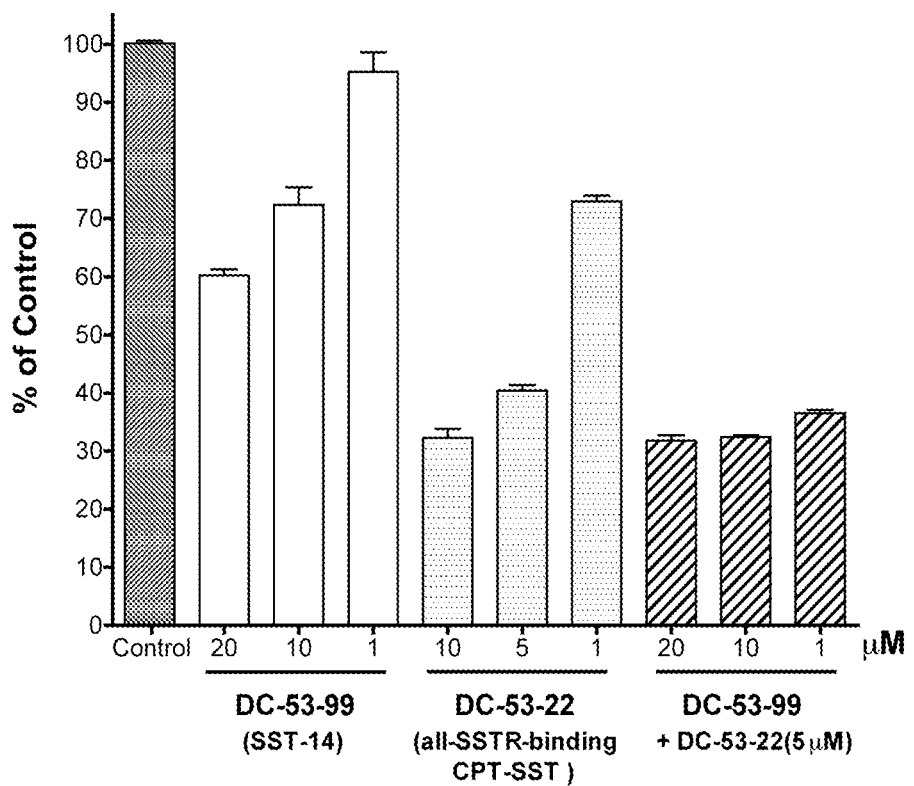
FIG. 31. SST-14 suppressed Hela-GFP cell proliferation. DC-53-22 enhanced the suppression.
Figure 32:
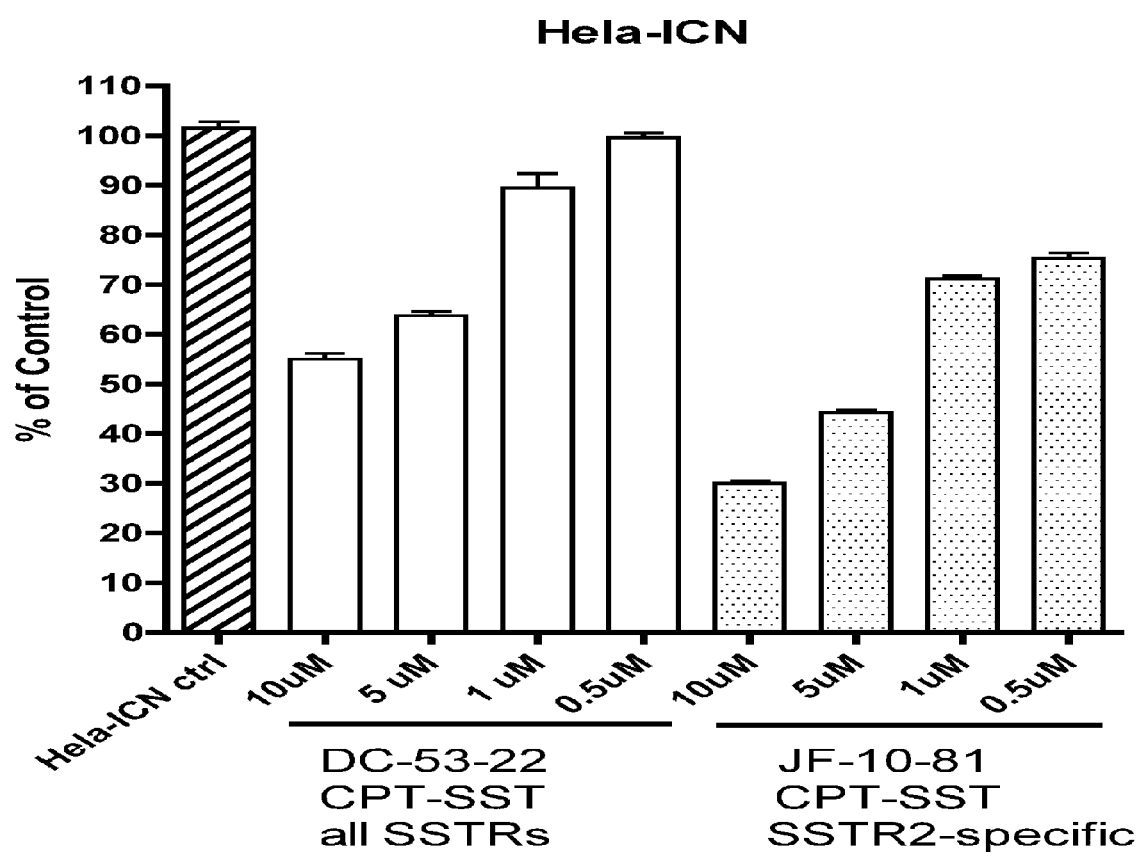
FIG. 32. Both conjugates JF-10-81 and DC-53-22 enhanced the suppression induced via Notch1 activation in Hela-ICN1 cells.
Figure 33:
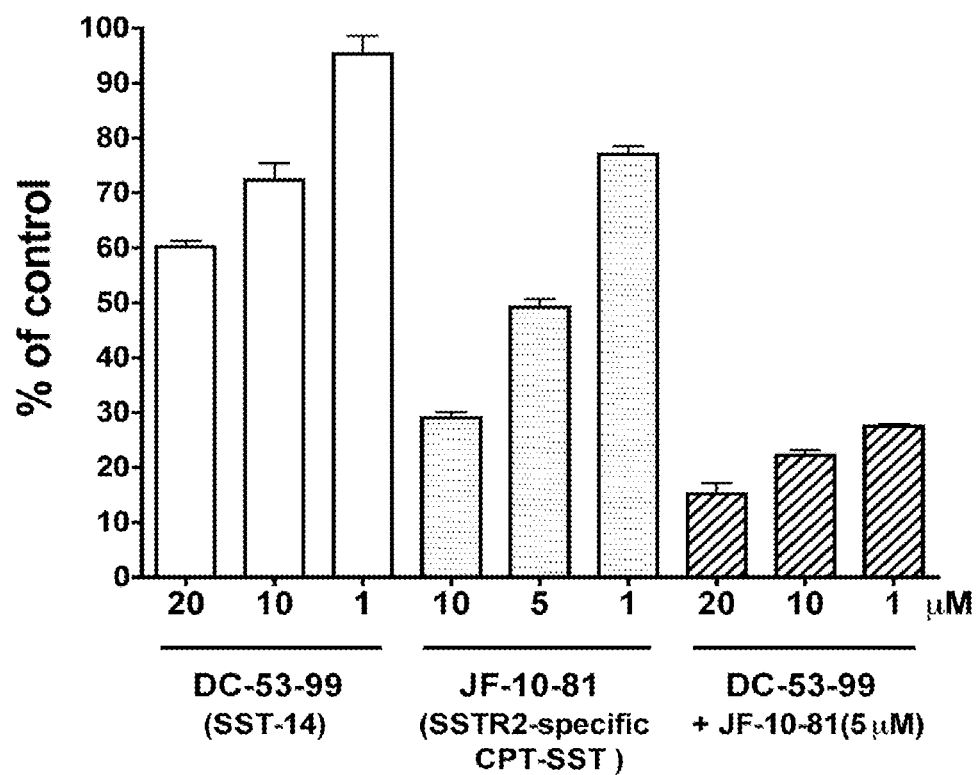
FIG. 33. SST-14 suppressed Hela-GFP cell proliferation. Conjugate CPT-SST (JF-10-81) enhanced the suppression.

The DC-53-22 conjugate suppressed cell growth of Hela-GFP cells with growth inhibition rate 32, 40, and 73% respectively under the conjugate treatment at 1, 5, and 10 μM (FIGS. 31 & 32). Conjugate JF-10-81 also displayed anti-proliferation ability (FIGS. 32 & 33).

Figure 24:
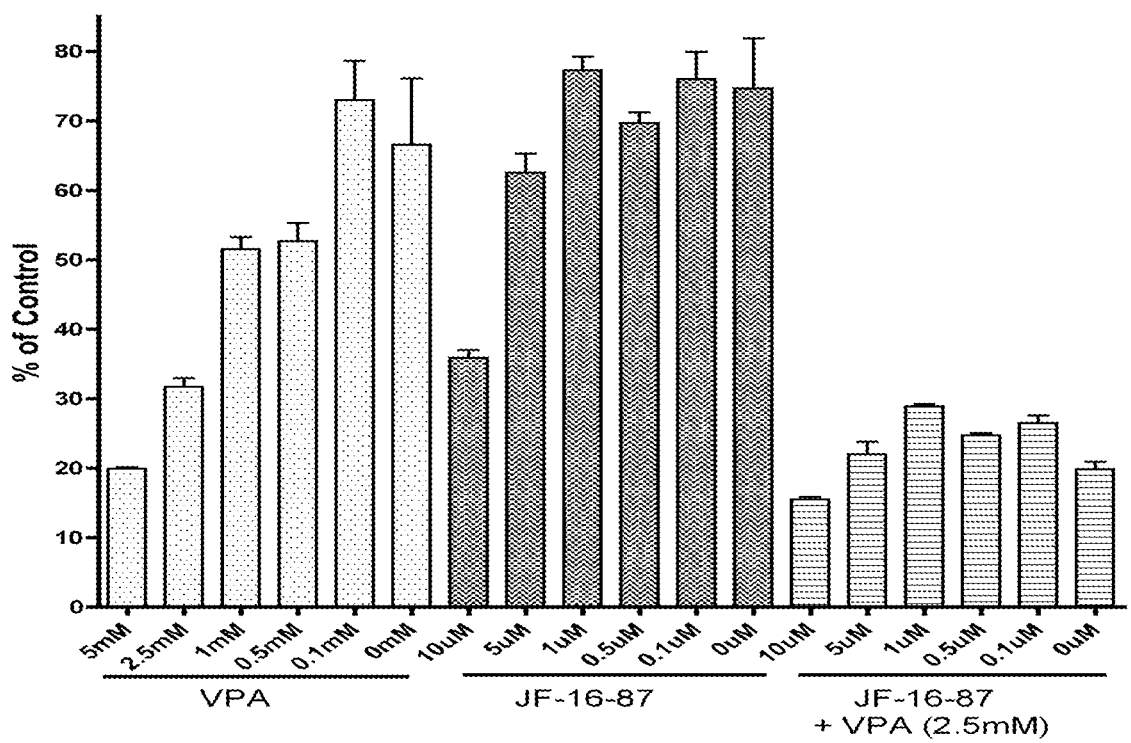
FIG. 24. The result of combination therapy of VPA and the colchicine-SST conjugate (JF-16-87) to lung cancer DMS-53 cell growth. 2.5 mM VPA enhanced the suppression of the colchicine-SST conjugate (JF-16-87) on DMS-53 cell growth.
Figure 34:
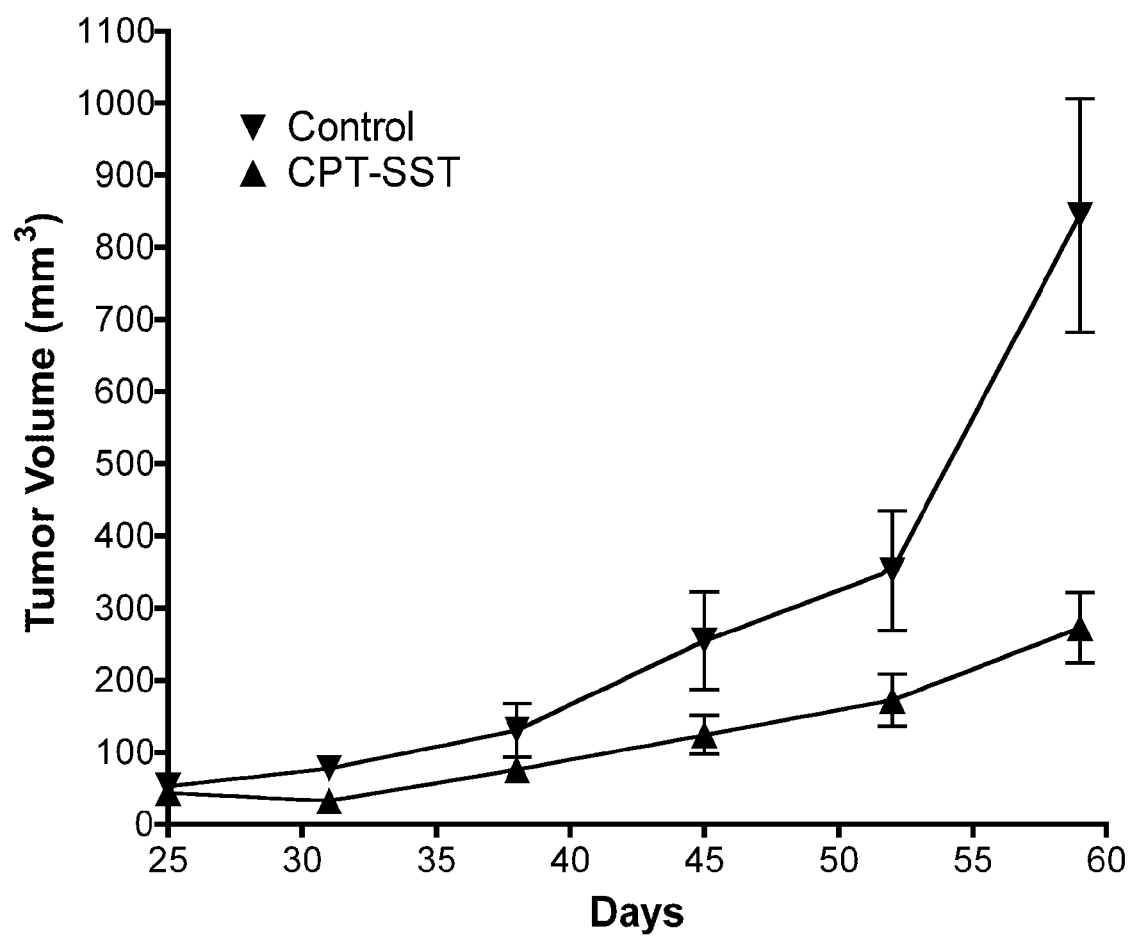
FIG. 34. The effects of conjugate JF-10-81 on pancreatic carcinoid BON tumor growth. In this experiment, BON tumors were treated with 2 mg/kg JF-10-81 once a day, 5 times per week, forming a total of 21 injections. The conjugate JF-10-81 suppressed pancreatic carcinoid BON cell growth.
Figure 35:
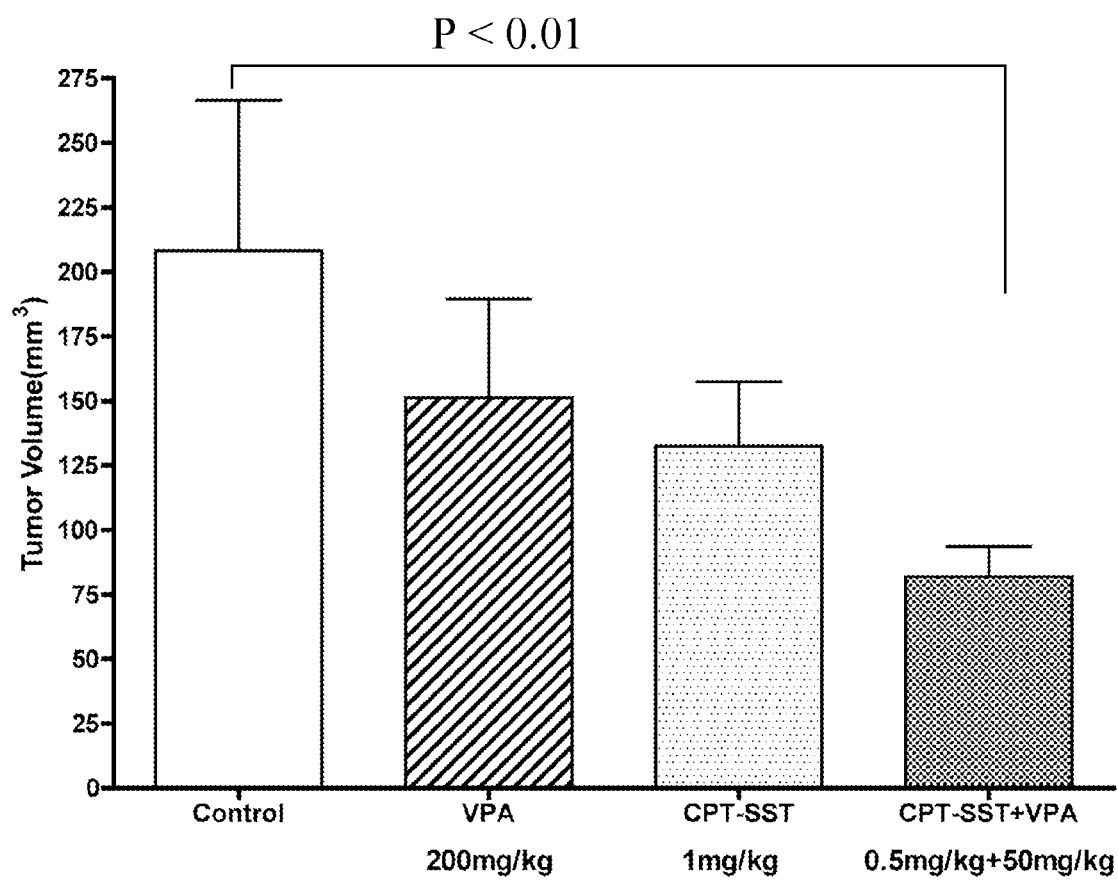
FIG. 35. The effects of conjugate JF-10-81 and/or Notch/SSTR2 inducer VPA on pancreatic carcinoid BON tumor growth. Nude mice carrying BON tumors were treated every other day, 3 times a week, totaling 12 injections. Combination therapy of VPA (50 mg/kg) and the conjugate JF-10-81 (0.5 mg/kg) at lower dose displayed a more potent anti-tumor ability than single VPA (200 mg/kg, 4-fold higher) or JF-10-81 (1 mg/kg, 2-fold higher) at higher doses. The combination therapy of VPA and the SSTR2-specific conjugate JF-10-81 enhanced the suppression to pancreatic carcinoid BON tumor growth.

We conducted in vitro and in vivo assays with Notch stimulators and SSTR-targeted cytotoxic SST conjugates. Notch stimulators VPA and SBHA were used in conjunction with the conjugates CPT-SST (JF-10-81) or Colichicine-SST (JF-16-87). From in vitro assays, we found that the combination of VPA/JF-10-81 or VPA/JF-16-87 enhanced growth suppression of cervical cancer Hela cells (FIGS. 19 & 22), pancreatic carcinoid BON cells (FIGS. 20 & 23), and small cell lung cancer DMS-53 cells (FIGS. 21 & 24). Through an in vivo assay, we demonstrated that the conjugate JF-10-81 alone could suppress carcinoid BON tumor growth (FIG. 34). Furthermore, we found that the combination therapy of VPA (50 mg/kg) and the CPT-SST conjugate (JF-10-81) (0.5 mg/kg) showed a more potent anti-tumor ability than single VPA (200 mg/kg, 4-fold higher) or CPT-SST (1 mg/kg, 2-fold higher) at higher doses (FIG. 35).

VPA-Enhanced Anti-Tumor Efficacy of SSTR2-Targeted CPT-SST Conjugate

Figure 36:
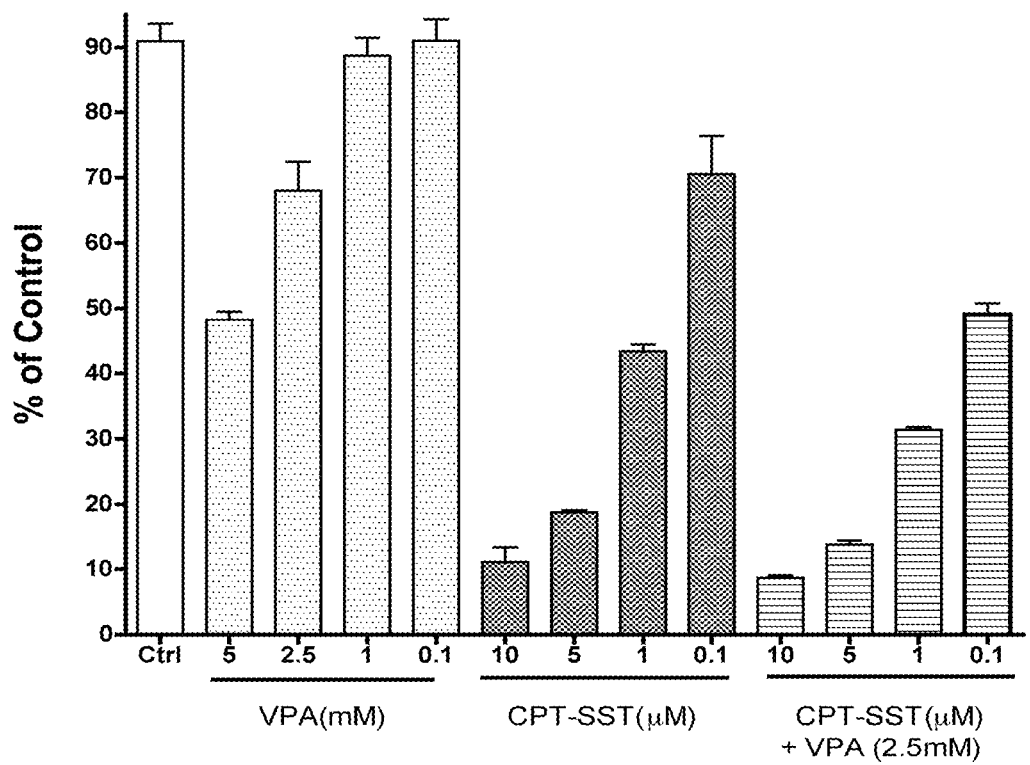
FIG. 36. Cell proliferation assay showed that VPA and conjugate CPT-SST alone suppressed cervical cancer Hela cell growth in a dose-dependent manner, but a combination treatment together enhanced the suppression.

We investigated the effects of VPA on Hela cell proliferation using in vitro MTT assays. We found that VPA itself suppressed cell proliferation in a dose-dependent manner (0-5 mM) (FIG. 36). In addition, the conjugate CPT-SST also induced growth arrest of Hela cells in a dose-dependent manner (0-10 μM). And it was observed that a combination treatment of both VPA and CPT-SST enhanced cell growth suppression (FIG. 36).

Figure 37:
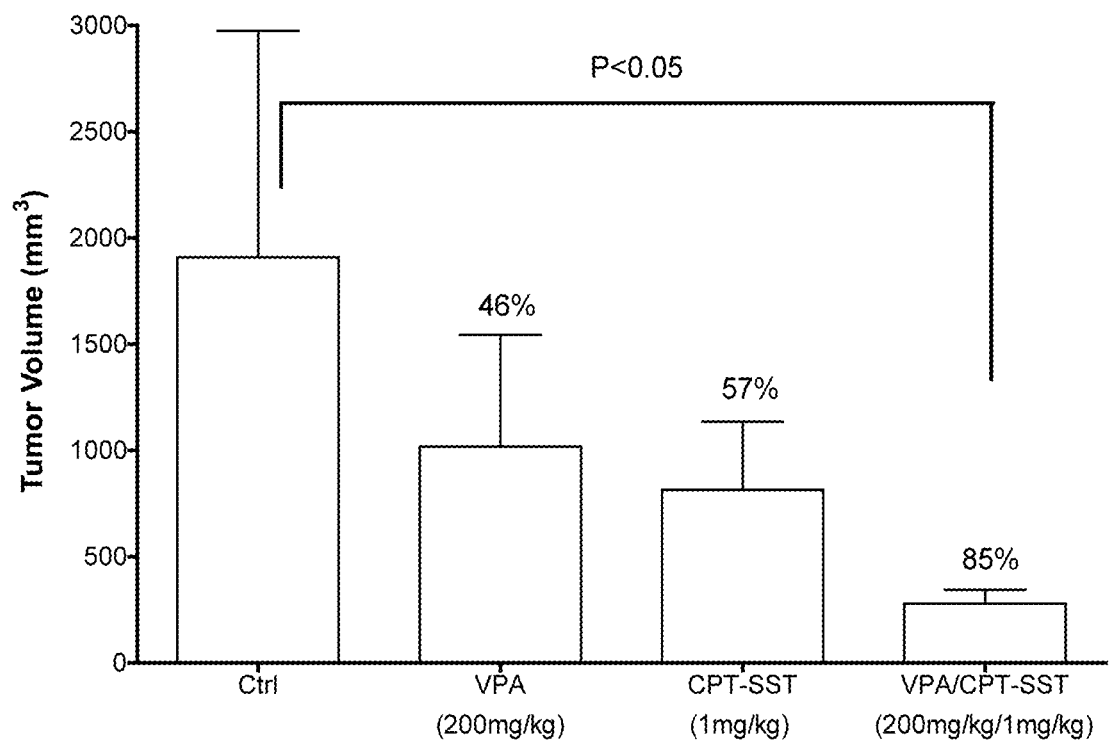
FIG. 37. Tumors grown from cervical cancer Hela cells were treated by VPA and CPT-SST. The tumor inhibitory rates induced via VPA at a dose of 200 mg/kg and CPT-SST at a dose of 1 mg/kg were 46% and 57%, respectively. The inhibitory effect of the combination treatment with VPA and CPT-SST increased to 85%.

We carried out an in vivo anti-tumor assay demonstrating that a combination treatment with both VPA and CPT-SST suppressed cervical cancer Hela tumor growth to a greater extent than individual treatment. As shown in FIG. 37, the inhibitory effects from treatments of VPA at 200 mg/kg and CPT-SST at 1 mg/kg are 46% and 57%, respectively. However, the inhibition from the combination therapy with VPA at 200 mg/kg and CPT-SST at 1 mg/kg was 85%. The suppressive ability of combination therapy is better than that via VPA or CPT-SST alone (FIG. 37) and these in vivo results suggest that VPA-mediated SSTR2 up-regulation could increase the uptake and anti-tumor efficacy of SSTR2-targeting conjugates, such as CPT-SST.

Example Set C

Materials and Methods

Unless otherwise provided below, all materials and methods are the same as those provided in Example Set A.

Cell Culture

Human osteosarcoma U2OS cells, pancreatic carcinoid BON cells, cervical cancer Hela and Hela-ICN1 cells (Notch1 activation, Hela cells transduced with ICN1), ovarian cancer OVCAR8 cells, pancreatic cancer CFPAC-1 cells, and colonrectal cancer HT-29 cells were cultured in medium supplemented with 10% FBS at 37° C. in a 5% $CO_2$ atmosphere.

Cell Proliferation Assay (MTT)

The cell proliferation assay was performed as described previously in Sun et al., Bioorg Med Chem Lett, 2004, Vol. 14, pp. 2041-2046. Briefly, 50 μl aliquots of medium with different concentrations of compounds were added to 96-well plates. All compound concentrations were tested in triplicate. Another 50 μl of the cell stock ($1\times10^5$ cells/ml of media) was dispensed into each test well and the plates were incubated at 37° C. in a $CO_2$ incubator for 3 days. Following the incubation period, 15 μl of the dye solution was added to each well and the plates were then incubated at 37° C. for 4 hours, followed by the addition of 100 μl per well of the solubilization solution. The plates were incubated at 37° C. until the contents in each well became a uniform-colored solution. The absorbance was measured and recorded at 570 nm by a Victor Plate Reader.

In Vivo Tumor Growth and Treatment

After being harvested during exponential growth phase, cells were washed 3 times with ice-cold PBS and then re-suspended in ice-cold PBS at a cell density of $4\times10^7$ cells/ml. Subcutaneous implantation of 100 μl aliquots of the cell suspension was placed in the flanks of 5-7 week old nude mice (NCI, Frederick, Md.) as described previously in Sun et al., Drug Deliv., 2004, Vol. 11, pp. 231-238. Tumor-carrying mice were separated into four groups (n=8-10) for further treatment using s.c. injections that was applied in the flank opposite of the tumors. A control group was injected with PBS, and three tested groups were treated with compounds. One group received conjugate COL-SST (2 mg/kg) and one group received 200 mg/kg of VPA. The last group was treated with 100 mg/kg of VPA in combination with 1 mg/kg of COL-SST. All mice were injected once a day, five times a week. Tumor volumes were measured and bodyweights taken once a week.

Figure 38:
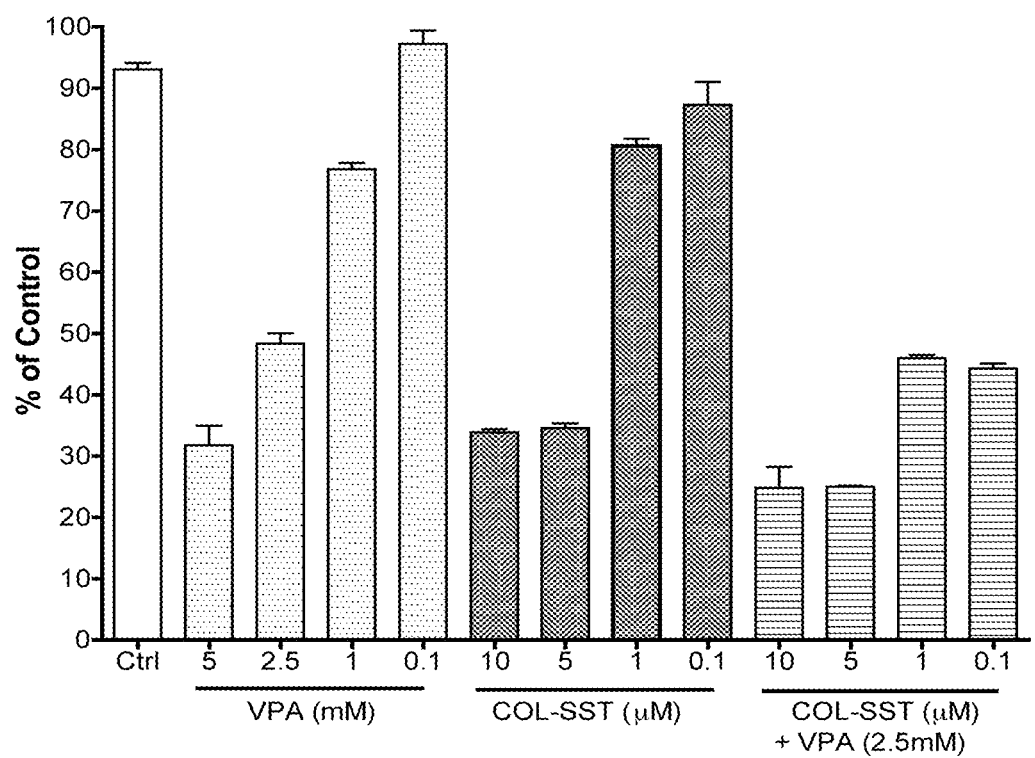
FIG. 38. VPA induced growth arrest of pancreatic carcinoid BON cells and enhanced the suppression of conjugate COL-SST (Colchicine-SST) for BON cells.
Figure 39:
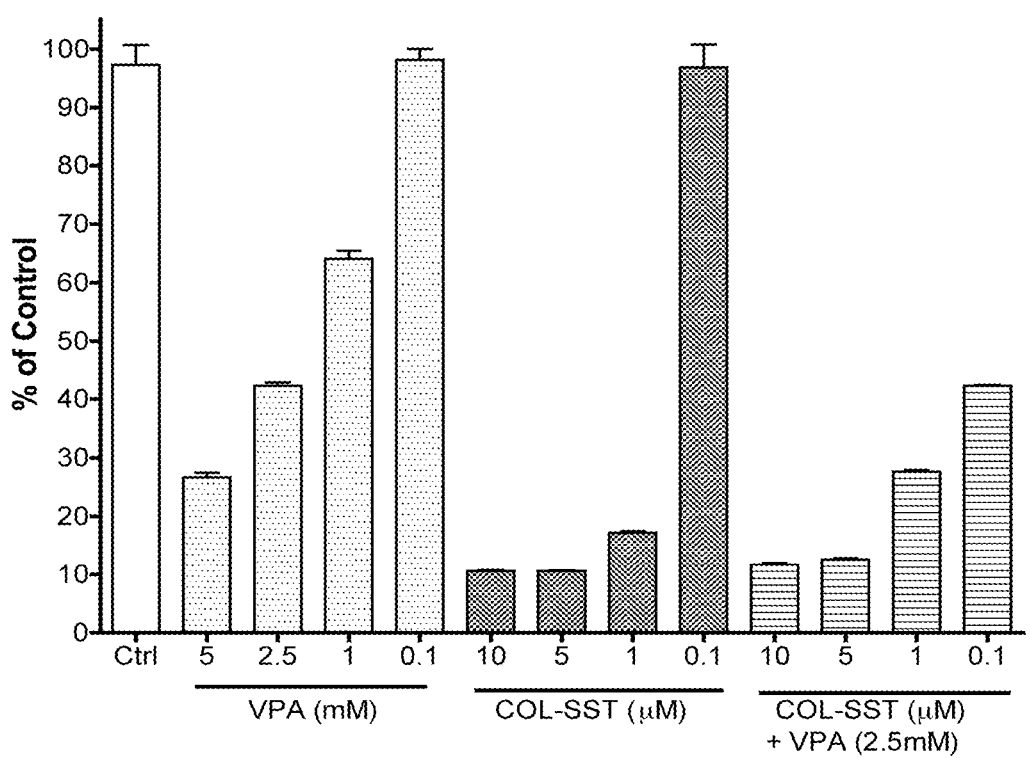
FIG. 39. VPA induced growth arrest of cervical cancer Hela cells and enhanced the suppression of conjugate COL-SST (Colchicine-SST) for Hela cells.
Figure 48:
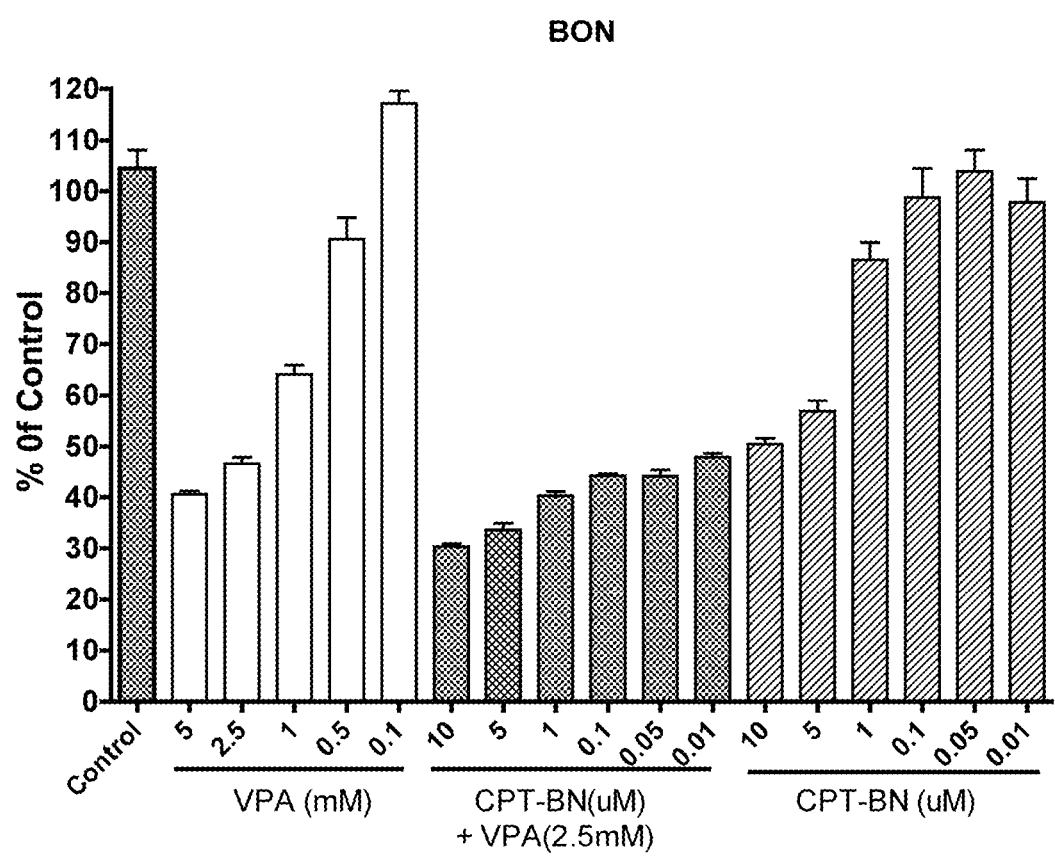
FIG. 48. VPA suppressed growth of pancreatic carcinoid BON cells and enhanced CPT-BN-induced suppression.
Figure 49:
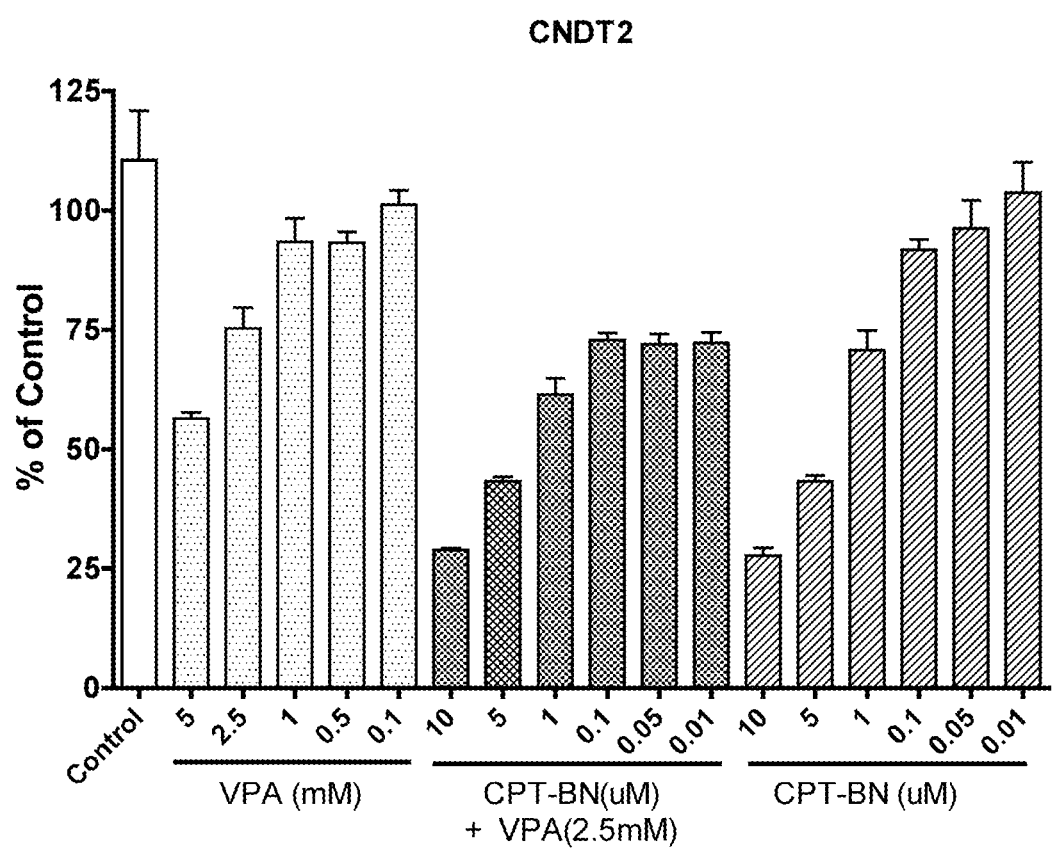
FIG. 49. VPA suppressed growth of CNDT2 cells and enhanced CPT-BN-induced suppression.
Figure 50:
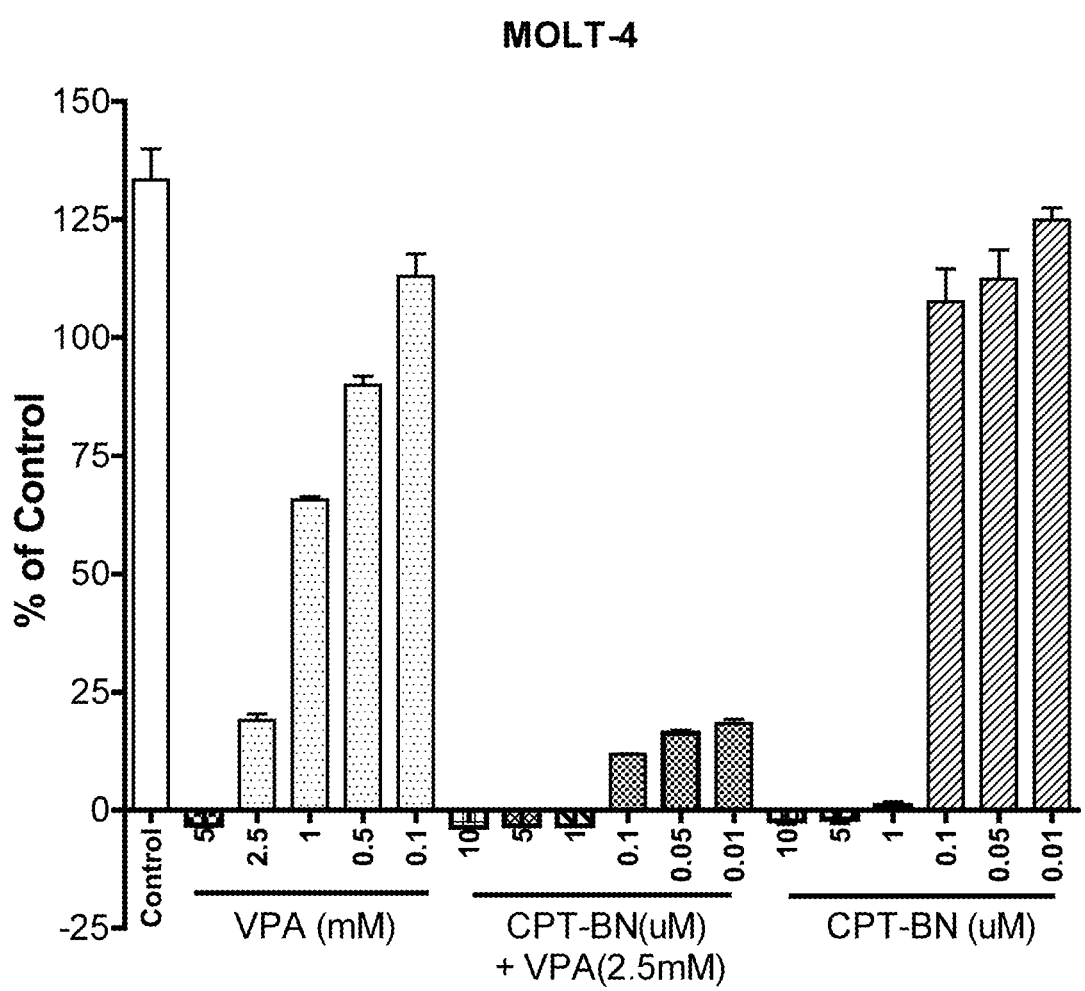
FIG. 50. VPA suppressed growth of Leukemic MOLT-4 cells and enhanced CPT-BN-induced suppression.

VPA Suppressed Cell Proliferation and Enhanced Anti-Proliferation of Receptor-Targeted Cytotoxic Peptide Conjugates VPA induced growth arrest of pancreatic carcinoid BON cells (FIG. 38), small-cell lung cancer (SCLC) DMS53 cells, medullary thyroid cancer (MTC) TT cells, and cervical cancer Hela cells (FIG. 39). These cancer cells have been identified with Notch signaling acting as a tumor suppressor. We further investigated the effects of VPA in combination with SSTR2-targeted cytotoxic SST conjugates on proliferation of cancer cells tested above via using in vitro MTT assays. VPA suppressed growth of these cancer cells in a dose-dependent manner (0-5 mM). The conjugates CPT-SST and COL-SST also induced growth arrest of these cancer cells in a dose-dependent manner (0-10 uM). It was also observed that a combination treatment of VPA with CPT-SST and VPA with COL-SST (FIG. 38 and FIG. 39) compared to each single agent alone, enhanced the growth suppression in the tested cancer cells (e.g., Hela cells in FIG. 39 and BON cells in FIG. 38). We also observed that VPA and CPT-BN conjugate enhanced anti-cell proliferation in treating certain cancer cells (FIGS. 48 to 50).

Figure 40:
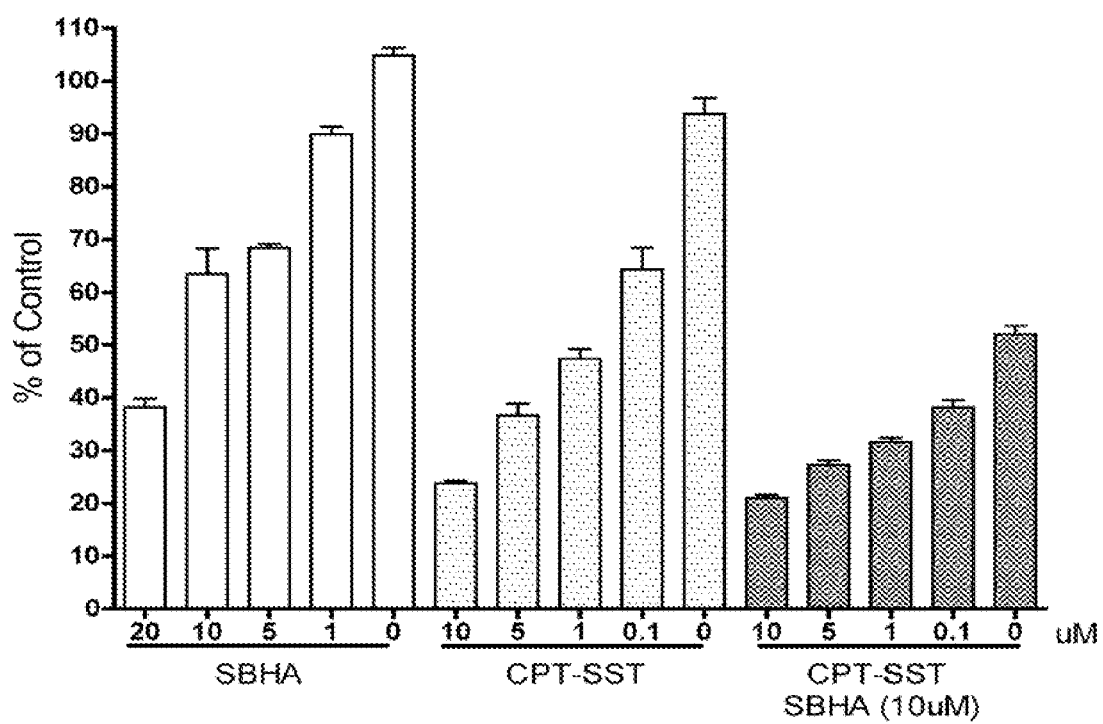
FIG. 40. SBHA (suberoyl bis-hydroxamic acid) induced growth suppression of pancreatic carcinoid BON cells and enhanced the suppression of conjugate CPT-SST on BON cell growth.
Figure 41:
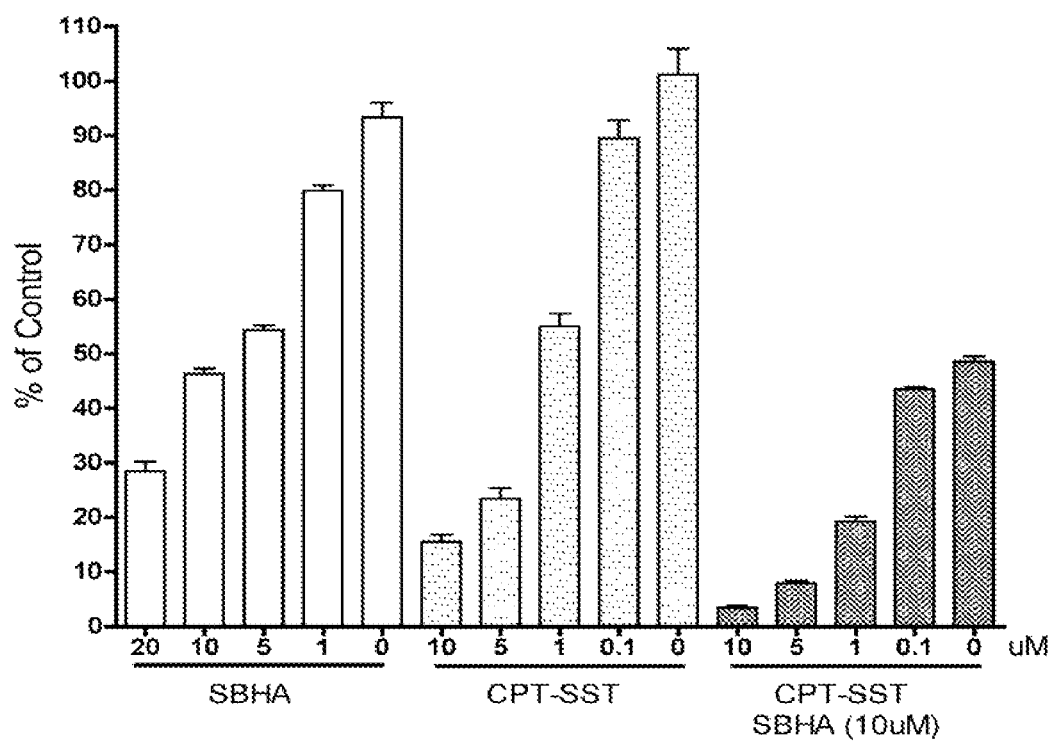
FIG. 41. SBHA induced growth suppression of small cell lung cancer (SCLC) DMS53 cells and enhanced the suppression of conjugate CPT-SST on DMS-53 cell growth.

With SBHA treatments, growth arrest was observed in many tested cancer cells with Notch acting as a tumor suppressor. SBHA also enhanced anti-cell proliferation of the conjugate CPT-SST on cancer cells such as pancreatic carcinoid BON cells (FIG. 40) and small cell lung cancer DMS-53 cells (FIG. 41).

Figure 42:
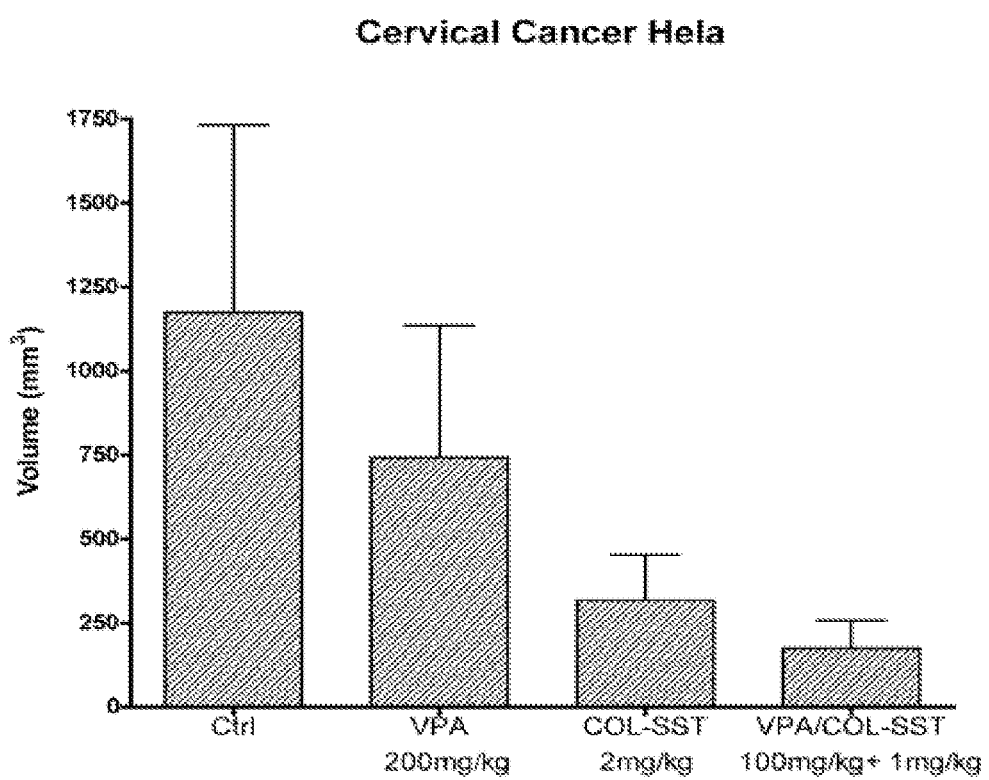
FIG. 42. VPA induced suppression of cervical cancer Hela tumors in nude mice and enhanced the suppression of conjugate COL-SST for Hela tumors.
Figure 43:
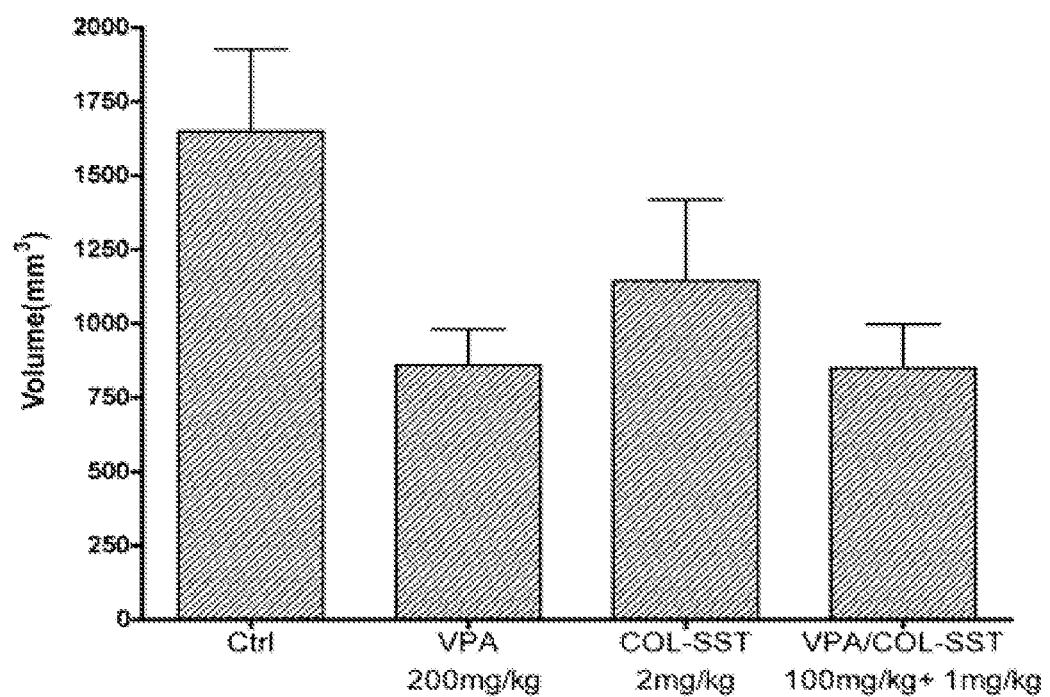
FIG. 43. VPA induced suppression of pancreatic carcinoid BON tumors in nude mice and enhanced the suppression of conjugate COL-SST for BON tumors.

The HDAC Inhibitor VPA Enhanced In Vivo Anti-Tumor Efficacy of SST Conjugate COL-SST A combination treatment with both VPA and the cytotoxic SST conjugate COL-SST suppressed cervical cancer Hela tumor growth, better than did each alone. As shown in FIG. 42, the inhibitory rates from treatments with VPA at 200 mg/kg or COL-SST at 2 mg/kg were 36.7% and 72.9%, respectively. However, the inhibition from the combination therapy with low doses of VPA at 100 mg/kg and COL-SST at 1 mg/kg was 85.8% (FIG. 42). Similar results were observed in treating pancreatic carciniod BON tumors with VPA and COL-SST (FIG. 43). The inhibitory rates from treatments of VPA at 200 mg/kg, COL-SST at 2 mg/kg, and the combination of VPA at 100 mg/kg and COL-SST at 1 mg/kg were 47.9%, 31.6%, and 48.5%, respectively (FIG. 43).

Figure 44:
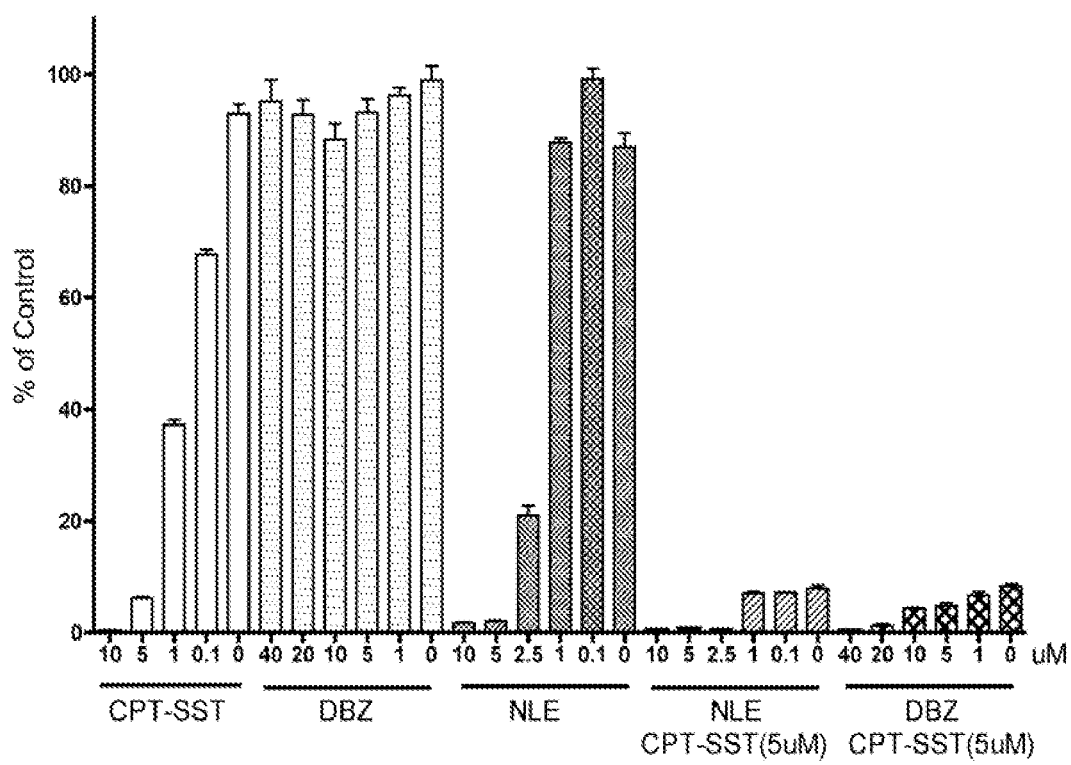
FIG. 44. The effects of conjugate CPT-SST and Notch inhibitors DBZ (dibenzazepine) and NLE on ovarian cancer OVCAR8 cell growth and the enhanced effects of the combination treatments with CPT-SST with DBZ and CPT-SST with Nle.
Figure 45:
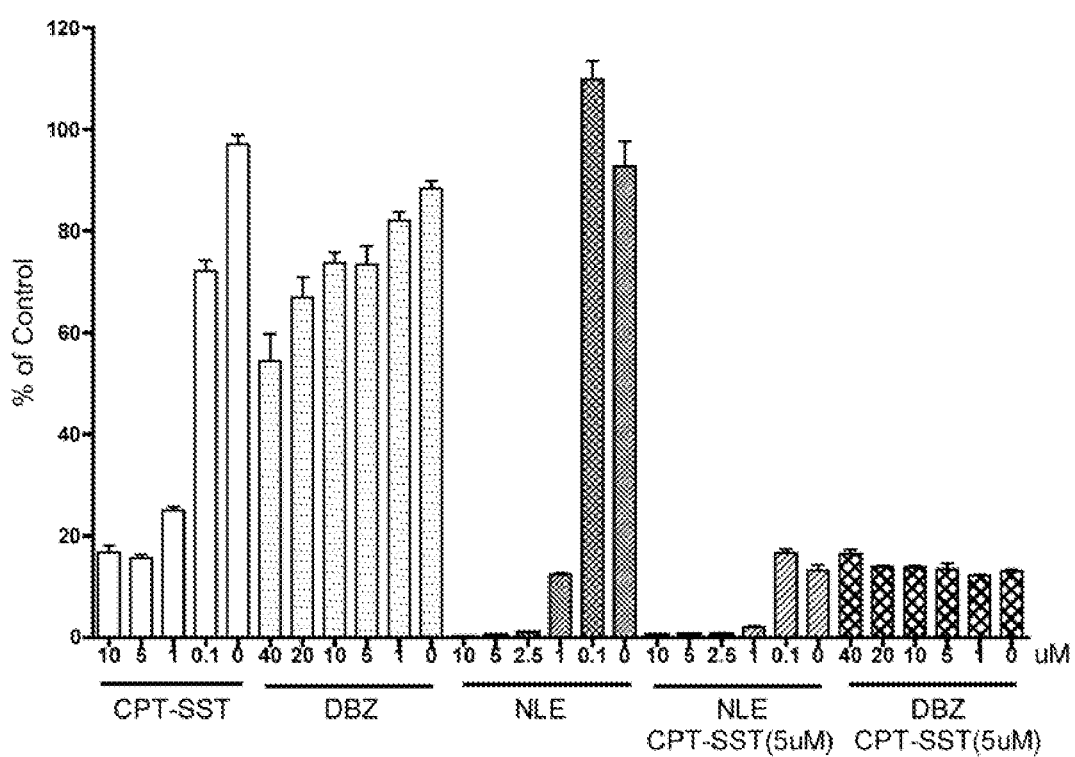
FIG. 45. The effects of conjugate CPT-SST and Notch inhibitors DBZ and NLE on pancreatic cancer CFPAC-1 cell growth and the enhanced effects of the combination treatments of CPT-SST with DBZ and CPT-SST with NLE.
Figure 46:
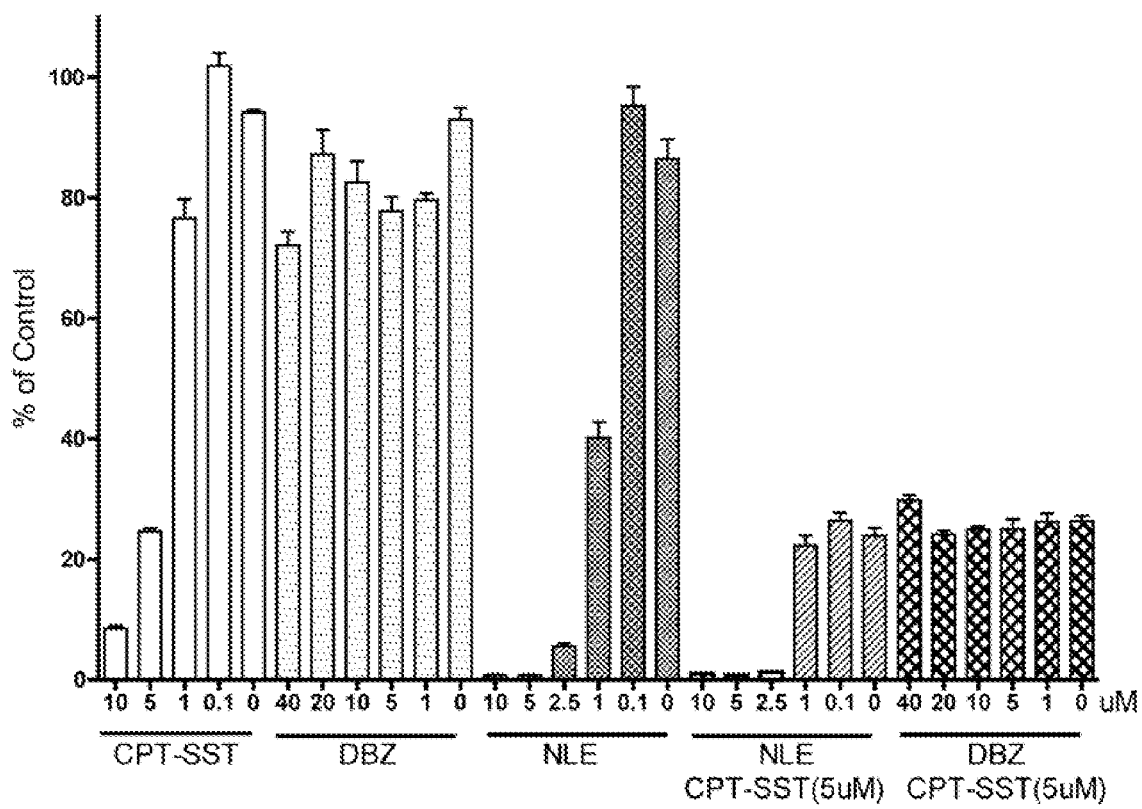
FIG. 46. The effects of conjugate CPT-SST and Notch inhibitors DBZ and NLE on colonrectal cancer HT-29 cell growth and the enhanced effects of the combination treatments of CPT-SST with DBZ and CPT-SST with NLE.

Notch Inhibitors Suppressed Cell Proliferation and Enhanced Anti-Proliferation of Conjugates We also investigated that the effects of some Notch inhibitors such as Z-Leu-Leu-Nle-CHO (Nle=Norleucine) (NLE) and dibenzazepine (DBZ) on cancer cell proliferation. These inhibitors induced cell growth arrest and enhanced the in vitro anti-proliferative effects of the ted conjugate CPT-SST in ovarian cancer OVCAR8 cells (FIG. 44), pancreatic cancer CFPAC-1 cells (FIG. 45), and colonrectal cancer HT-29 cells (FIG. 46).

Example Set D

Materials and Methods

Unless otherwise provided below, all materials and methods are the same as those provided in Example Set A.

Cell Culture

Human pancreatic carcinoid BON cells were a gift of Dr. Courtney Townsend (University of Texas—Galveston) and were grown as described in Sun et al. 2007. Cervical cancer Hela-ICN1 cells (Notch1 activation, Hela cells transduced with ICN1) were a gift from Dr. Lizi Wu (University of Florida) and were grown as described in Sun et al. 2007. Human T-cell acute lymphoblastic leukemia (T-ALL) HPB-ALL cells were maintained in RPMI-1640 medium. Osteosarcoma U2OS cells were cultured in McCoy's 5A medium. Lymphoma Jurkat cells were grown in RPMI-1640 medium. Cervical cancer Hela cells were cultured in F-12 medium supplemented with 10% FBS. Small cell lung cancer (SCLC) DMS53 were maintained in Waymouth's medium; medullary thyroid cancer (MTC) TT cells were maintained in F-12 medium; hepatoma HB-8064 (Hep3B) and HTB-52 cells were maintained in MEM medium; ovarian cancer OVCAR8, SKOV3 and NCI/ADR-RES cells were maintained in RPMI-1640 medium. All culture media was supplemented with 10% FBS. The other cancer cells including prostate cancer DU-145 cells, prostate cancer PC-3 cells, pancreatic cancer CFPAC-1 cells, lung cancer A549, Leukemia MOLT-4 cells, and colon cancer HT-29 cells were cultured as described in Sun et al. 2007 and Sun et al., J Drug Target, 2011, Vol. 19, pp. 719-30 (Sun et al. 2011).

RT-PCR, Real-Time PCR

RT-PCR was performed on total RNA that was isolated from tumor cells as described in the protocol (Invitrogen, Carlsbad, Calif.). All primers for SST, BN, and PACAP receptors were obtained from previously published reports, such as Sun et al. 2011. The other primers and conditions for RT-PCR analyses are shown in Table 4. The PCR amplification is regularly 35 cycles, with more or less cycles due to the difference in RNA abundance of these investigated genes. Primers used for real-time PCR analyses were identical to those described above. Real-time PCR assays were performed as described in Sun et al 2011. β-actin was used as the internal control and results were calculated by applying $2^{-\Delta\Delta C_T}$ methods as described above.

TABLE 4

Primer sequences and PCR conditions for gene amplification

| Receptor | Primers | PCR conditions | PCR products (bp) | Ref./GeneBank No |
|---|---|---|---|---|
| Notch1 | F: 5' GGC CAC CTG GGC CGG AGC TTC 3' R: 5' GCG ATC TGG GAC TGC ATG CTG 3' | 35 cycles (95° C., 40 s, 65° C., 30 s, 72° C., 30 s) | 365 | Ref. 1 |
| Notch2 | F: 5' GGC CCC CTG CCC ACC ATG TAC 3' R: 5' CCC GCT GAC CTC CTC CAG C 3' | 35 cycles (95° C., 40 s, 65° C., 30 s, 72° C., 30 s) | 343 | Ref. 1 |
| Notch3 | F: 5' TTC TTA GAT CTT GGG GGC CT 3' R: 5' GGA AGA AGG AGG TCC CAG AC 3' | 35 cycles (95° C., 40 s, 58° C., 30 s, 72° C., 30s) | 218 | Ref. 2 |
| Notch4 | F: 5' AGC AGA CAA ACT GCA GTG GA 3' R: 5' CTG TTG TCC TGG GCA TCT TT 3' | 35 cycles (95° C., 40 s, 55° C., 30 s, 72° C., 30 s) | 233 | NM_004557 |
| PCNA | F: 5' AGC ACG CAC CCT GCC ACA AT 3' R: 5' ACA GCC CAG CAG CAG CAT GA 3' | 35 cycles (95° C., 60 s, 63.8° C., 30 s, 72° C., 60 s) | 230 | NM_005618 |
| COX2 | F: 5' AAC AGC CCG GTG AAT GCC GA 3' R: 5' ACA CAA GCC GCC GTT GAA GCA 3' | 35 cycles (95° C., 60 s, 55° C., 30 s, 72° C., 60 s) | 287 | NG_008256 |

TABLE 4-continued

Primer sequences and PCR conditions for gene amplification

| Receptor | Primers | PCR conditions | PCR products (bp) | Ref./GeneBank No |
|---|---|---|---|---|
| BCL-2 | F: 5' TGA TTC CTG CCG CCC AGC TT 3'<br>R: 5' TGT AAC CGC AGT GGC GCC TT 3' | 35 cycles (95° C., 60 s, 63.8° C., 30 s, 72° C., 60 s) | 205 | NM_019074 |
| MMP2 | F: 5' AAC GAC CGC AAC CGC ATC GT 3'<br>R: 5' AAA GTG GGC AAC GCC CGT GT 3' | 35 cycles (95° C., 60 s, 58.9° C., 30 s, 72° C., 60 s) | 195 | NM_000214 |
| p53 | F: 5' CAG CAT CTT ATC CGA GTG GAA GG 3'<br>R: 5' CAC AAA CAC GCA CCT CAA AGC 3' | 35 cycles (95° C., 60 s, 59° C., 30 s, 72° C., 60 s) | 253 | NM_001126117 |
| p21 | F: 5' TGA TGC GCT AAT GGC GGG CT 3'<br>R: 5' TGC TGG TCT GCC GCC GTT TT 3' | 35 cycles (95° C., 60 s, 60° C., 30 s, 72° C., 60 s) | 338 | NM_001220778 |
| p63 | F: 5' TCC TCA GGG AGC TGT TAT CC 3'<br>R: 5' ACA TAC TGG GCA TGG CTG TT 3' | 35 cycles (95° C., 60 s, 56° C., 30 s, 72° C., 60 s) | 171 | NM_001114982 |

Ref 1 - Primer sequence found in Talora et al., Genes & Dev., 2002, Vol. 16, pp. 22520-2263.
Ref. 2 - Primer sequence found in Bellavia et al., EMBO J., 2007, Vol. 26, pp. 1670-1680.

VPA-Induced Cell Morphological Change

The assay for VPA-induced cell morphological change was performed by adding 50 µl of cells ($1\times10^5$ cells/ml) and 50 µl of culture media, with or without the test compound VPA, to each well of 96-well plates. The cancer cells were inspected and photographed under an inverted light microscope at 10× magnification.

Cell Proliferation Assay (MTT)

The cell proliferation assay (Promega, Madison, Wis.) was performed as described in Sun et al., Bioorg Med Chem Lett, 2004, Vol. 14, pp. 2041-2046. The absorbance was measured and recorded at 570 nm by a Victor Plate Reader (PerkinElmer, Boston, Mass.).

In Vivo Tumor Growth and Treatment

After being harvested during their exponential growth phase, cells were washed 3 times with ice-cold PBS and then re-suspended in ice-cold PBS at a cell density of $4\times10^7$ cells/ml. Subcutaneous implantations of 100 µl aliquots of the cell suspension were placed in the flanks of 5-7 week old nude mice (NCI, Frederick, Md.) as described previously in Sun et al., Clin Med Oncol, 2008; Vol. 2, pp. 491-9. Tumor-carrying mice were separated into four groups (n=8-10) for further treatment using s.c. injections that were applied in the flank opposite to the tumors. A control group was injected with PBS and three tested groups were treated with compounds. One group received conjugate COL-SST (2 mg/kg) and one group received 200 mg/kg of VPA. The last group was treated with 100 mg/kg of VPA in combination with 1 mg/kg of COL-SST. All mice were injected once a day, five times a week. Tumor volumes were measured and bodyweights taken once a week.

Results

VPA Suppresses Cell Proliferation and Tumor Growth

Figure 47:
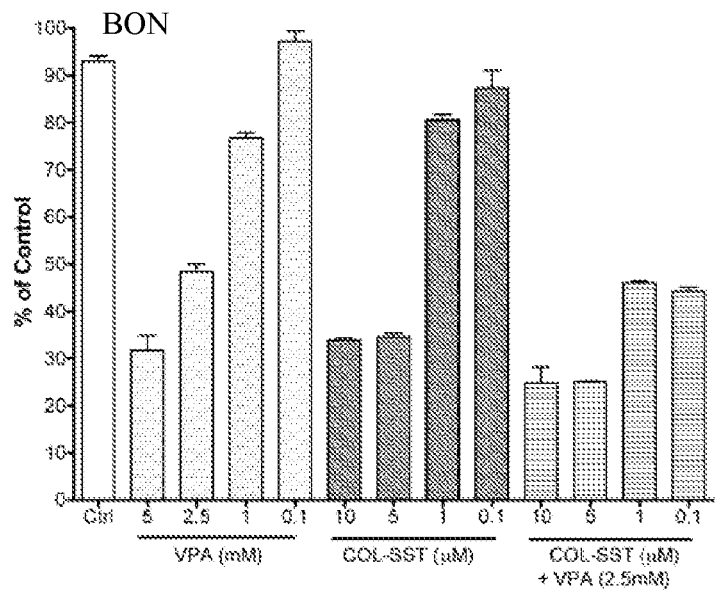
FIG. 47. Cell proliferation assay. VPA enhanced the antiproliferation ability of conjugate COL-SST in pancreatic carcinoid BON and cervical cancer Hela cells.
Figure 47:
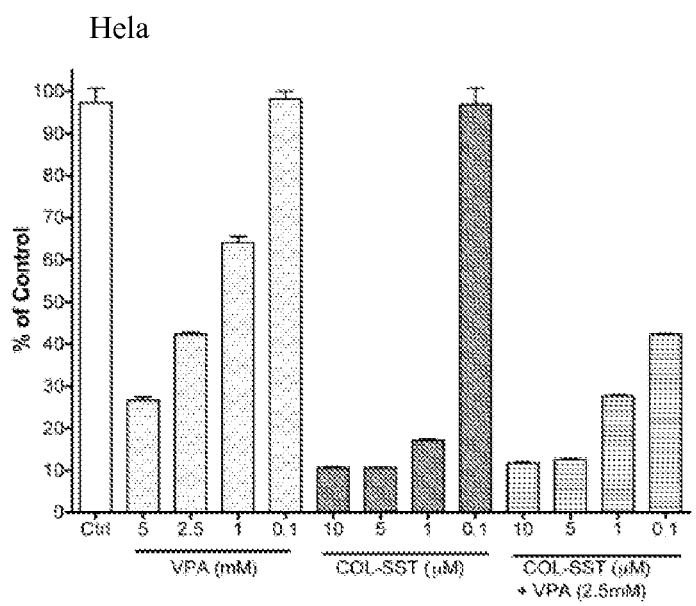
Figure 51:
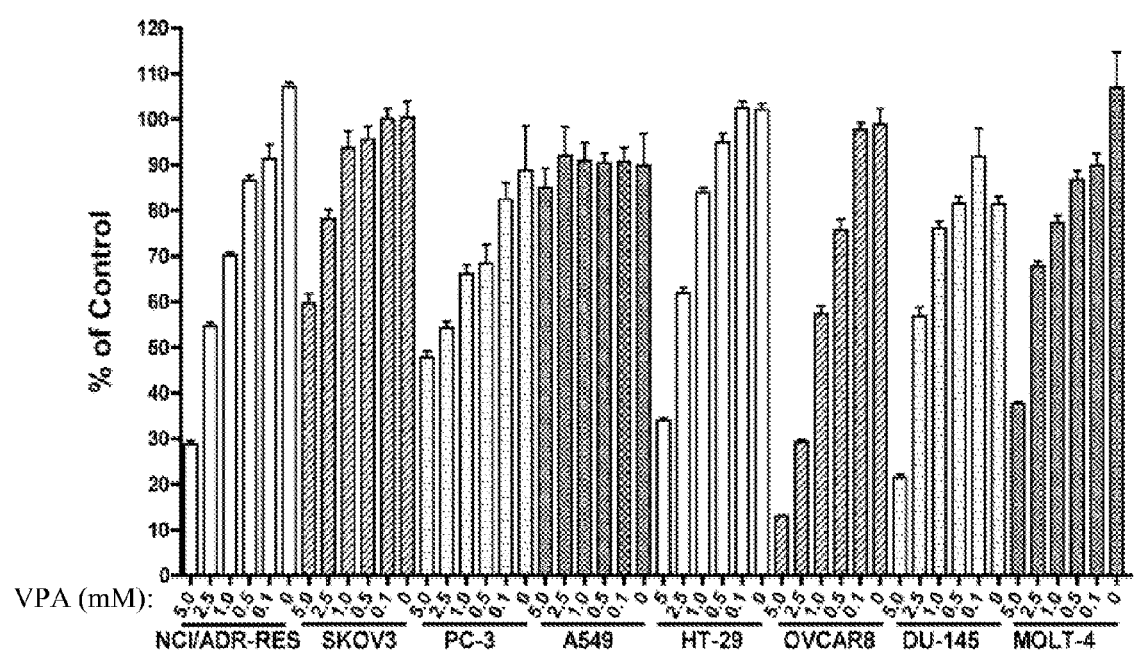
FIG. 51. Cell proliferation assay. Shown are the six representative cancer cell lines chosen from the sixteen different types of cancer cells tested with VPA. VPA displays its antiproliferation ability in leukemia MOLT-4, prostate cancer DU-145, prostate cancer PC-3, colon cancer HT-29, ovarian cancer OVCAR8, SKOV3, and NCI/ADR-RES cells but was not apparent in lung cancer A549 cells.

VPA induced growth arrest of pancreatic carcinoid BON cells (FIG. 47), SCLC DMS-53 cells, MTC TT cells and cervical cancer Hela cells (FIG. 47). These cancer cells have been identified with Notch signaling acting as a tumor suppressor. Furthermore, we found that, via in vivo anti-tumor assays as described below, VPA suppressed growth of Hela and BON tumors, with inhibitory rates of 36.7% and 47.9%, respectively (FIG. 42 and FIG. 43). VPA also displayed its anti-proliferative ability in many other cancer cells such as hepatoma HB-8064, HTB-52, ovarian cancer OVCAR8, SKOV3 and NCI/ADR-RES cells, prostate cancer DU-145 and PC-3 cells, pancreatic cancer CFPAC-1 cells, T-ALL HPB-ALL cells, Leukemia MOLT-4 and Jurkat cells, osteosarcoma U2OS cells, and colon cancer HT-29 cells. Some of these cells have been reported with Notch signaling acting as an oncogene. Shown in FIG. 51 are part of the results of many of these VPA-treated cancer cells. However, VPA had little effect on lung cancer A549 cell proliferation.

VPA Appeared to Regulate Notch Expression in Cancer Cells

We found that Notch2 was detectable in pancreatic carcinoid BON cells, with less expression of TT, DMS-53, and HTB-52 genes. In SCLC DMS53 cells, Notch1, Notch2, and Notch4 were detected; Notch3 was undetectable. In MTC TT cells, all Notch genes were detectable with low expression. In hepatoma HTB-52 cells, Notch1 and Notch2 receptors were expressed at a higher level compared to the trace or undetected expression of Notch3 and Notch4 (data not shown).

Figure 52:
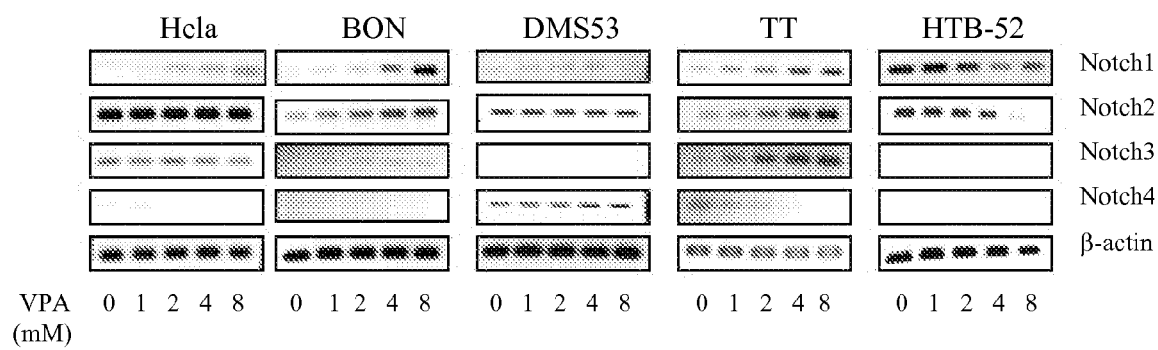
FIG. 52. RT-PCR detection of the VPA-mediated Notch expression in cervical cancer Hela, pancreatic carcinoid BON, SCLC DMS-53, MTC TT, and hepatoma HTB-52 cells.

We investigated the effects of VPA on the expression of Notch receptors in these cells. Cancer cells were treated with VPA at serial doses and then Notch expression was analyzed via RT-PCR. We found that VPA increased Notch1 expression in Hela cells, with no obvious change in the expression of other Notch genes. As for pancreatic carcinoid BON cells, VPA treatment increased the expression of Notch1, Notch2, and Notch3; Notch4 was undetectable. In DMS-53 cells, VPA increased the expression of Notch1 and Notch2, with no obvious change of expression in the others. Real-time PCR analysis further confirmed VPA-induced Notch1 increase (>2-fold). In TT cells, VPA treatments were found to significantly increase Notch1, Notch2, and Notch3, with a decrease of Notch4 expression. But in HTB-52 cells, we observed that VPA treatment decreased Notch1 and Notch2, whereas Notch3 and Notch4 were undetectable (FIG. 52). Our findings indicate that VPA increased Notch1 expression in the four types of cancer cells in which Notch signaling reportedly acts as a tumor suppressor. However, VPA decreased Notch signaling in HTB-52 cells in which VPA acts as a Notch inhibitor or Notch signaling may act as an oncogene.

The Involvement of VPA-Mediated Signaling Pathways

Several genes including COX2 (prognostic marker), MMP2 (cell invasive and metastasis marker), BCL-2 (anti-apoptotic marker), p53 (tumor suppressor), p21 (tumor suppressor), p63 (tumor suppressor), PCNA (proliferation marker), and SST (growth hormone-releasing inhibitory factor) were investigated for their effects of ICN1 and VPA on Hela cells via RT-PCR and real-time PCR.

The Expression of VPA-Mediated Tumor-Related Markers

Figure 53:
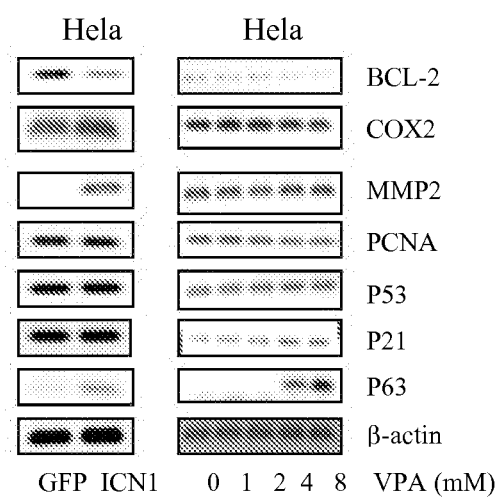
FIG. 53. RT-PCR detection of the VPA-mediated expression of certain cancer-related genes (BCL-2, COX2, MMP2, PCNA, p53, p21, and p63) in Hela cells. The effects of ICN1 activation on these genes were also investigated in Hela cells (Hela-ICN1).

ICN1 induced an increase in COX2 (11.8-fold, MMP2 (47.6-fold) and SST (342-fold) and a decrease in BCL-2 (4.5-fold) and PCNA (2.2-fold) in Hela cells, confirmed by real-time PCR. VPA did the same in Hela cells (FIG. 53 and FIG. 54), with an increase in COX2 (3.7-fold, MMP2 (25-fold) and SST (1.4-fold) and a decrease in BCL-2 (42.2-fold) and PCNA (476-fold). We also observed that an increase of COX2, MMP, SST and a decrease of BCL-2 and PCNA in BON, TT, DMS53 and HTB-52 cancer cells (data not shown).

VPA-Mediated p53 Family Signaling

The effects of VPA and ICN1 on p53 and the p53 family were also investigated. Analysis by RT-PCR and real-time PCR showed that the two genes p21 and p63 were up-regulated by ICN1 and VPA in Hela cells. The ICN1-induced increase of p21 and p63 was 7.4 and 9.0-fold higher than controls, respectively. The VPA-induced increase of p21 and p63 was 18 and 12, respectively. However, the change of p53 induced by ICN1 and VPA was different. p53 was increased by ICN1 (1.6-fold), but decreased by VPA (3.1-fold). The same change trends of p53, p21, and p63 induced by VPA was also observed in BON, TT, DMS53, and HTB-52 cancer cells (data not shown).

VPA-Mediated pTEN/PI3K/Akt Signaling

We compared the effects of ICN1 and VPA on pTEN/PI3K/Akt signaling in Hela cells (Tables 2 and 5). We observed that an increase of PI3K resulted from both ICN1 (6.7-fold) and VPA (2-fold) treatments, with a difference of the expression of Akt and pTEN in two treatments. Akt and pTEN were down-regulated by ICN1 (3.44- and 1.8-fold, respectively) and up-regulated by VPA (2.1- and 1.9-fold, respectively) (Table 5 and FIG. 53). VPA- and ICN1-mediated PI3K/Akt signaling in Hela cells may be through different signaling pathway cascades. We also investigated the expression of gene-related signaling and the expression of certain GPCR members (discussed below).

TABLE 5

Expression of certain genes in cervical cancer Hela cells Real-time PCR.

| Genes | VPA | ICN1 |
|---|---|---|
| PI3K | 2.00 ± 0.21 | 6.72 ± 2.19 |
| Akt | 2.10 ± 0.28 | −3.44 ± 0.49 |
| pTEN | 1.87 ± 0.22 | −1.77 ± 0.13 |
| Snail | 52.9 ± 20 | 1.42 ± 0.14 |
| Slug | 35.1 ± 14.4 | 1.24 ± 0.05 |
| Twist | 3.36 ± 0.91 | 2267 ± 1253 |
| E-cadherin | 24.7 ± 4.68 | −2.75 ± 0.46 |

TABLE 5-continued

Expression of certain genes in cervical cancer Hela cells Real-time PCR.

| Genes | VPA | ICN1 |
|---|---|---|
| N-cadherin | 13.67 ± 5.96 | 150.1 ± 27.41 |
| Fibronectin | 38.55 ± 19.42 | 3411 ± 1809 |

Figure 54:
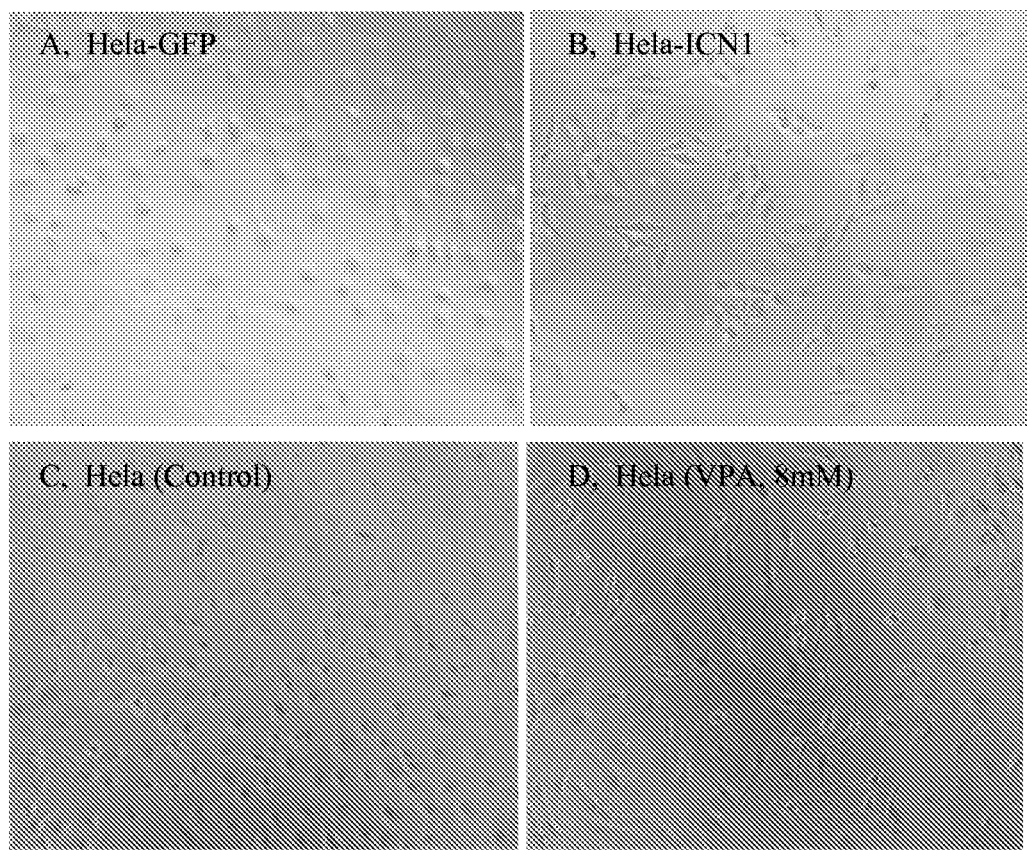
FIG. 54. VPA- and ICN1-induced Hela cell morphological change. (A) Hela-GFP cells (Control) and (B) Hela-ICN1 cells (Notch1 activation via ICN1). (C) and (D) show Hela cells treated with VPA at 0 (C) and 8 mM (D).

VPA-Induced Epithelial-Mesenchymal Transformation/Transition (EMT) in Cervical Cancer Cells We observed morphological changes in the Notch1-activated Hela-ICN1 cells (FIG. 54). We also found that VPA could induce morphological change in cervical cancer Hela (FIG. 54), osteosarcoma U2OS, hepatoma HTB-52, and pancreatic carcinoid BON cells, with no effect on all other tested cancer cells, including lung cancer A549, SCLC DMS53, pancreatic cancer DU-145, leukemia MOLT-4, Jurkat and HPB-ALL, ovarian cancer NCI/ADR-RES, and MTC TT.

Cervical cancer Hela cells were chosen to compare the difference between ICN1- and VPA-induced gene expression in EMT. We initially investigated the effects of ICN1 on EMT and the expression of the EMT-relevant genes and observed that snail (1.4-fold), slug (1.2-fold), twist (2267-fold), fibronectin (3411) and N-cadherin (150-fold) were up-regulated and E-cadherin (2.8-fold) was down-regulated in Hela-ICN1 cells (Table 5). As mentioned above, MMP2 (47.6-fold) was also increased in cervical cancer Hela-ICN1 cells. The gene twist may initiate the EMT process induced by ICN1. These findings support that Notch1 activation via ICN1 induced EMT in cervical cancer Hela cells. We further investigated the effects of VPA on the expression of these EMT-related genes in Hela cells. We found that VPA mediated the up-regulation of these genes, including snail (53-fold), slug (35-fold), twist (3.4-fold), N-cadherin (14-fold), fibronectin (39-fold) and MMP2 (25-fold as mentioned above). Moreover, we found an increase of VPA-induced E-cadherin (25-fold) (Table 5), different from the ICN1-induced decrease. The expression level of genes snail, slug, and twist induced by VPA is different from that in ICN1-induced Hela cells (Hela-ICN1) although both ICN1 and VPA mediated an increase in these genes (Table 5). These indicate that VPA might induce EMT via snail and slug VPA Induced the Expression of Certain GPCRs We investigated the effects of Notch1 activation in Hela-ICN1 cells and VPA in five cancer cell lines (Hela, BON, TT, DMS53, and HTB-52) on the expression of the SST, BN, and PACAP receptors (SSTR1-5, GRPR, BRS3, NMBR, PAC1, VPAC1, and VPAC2).

Figure 55:
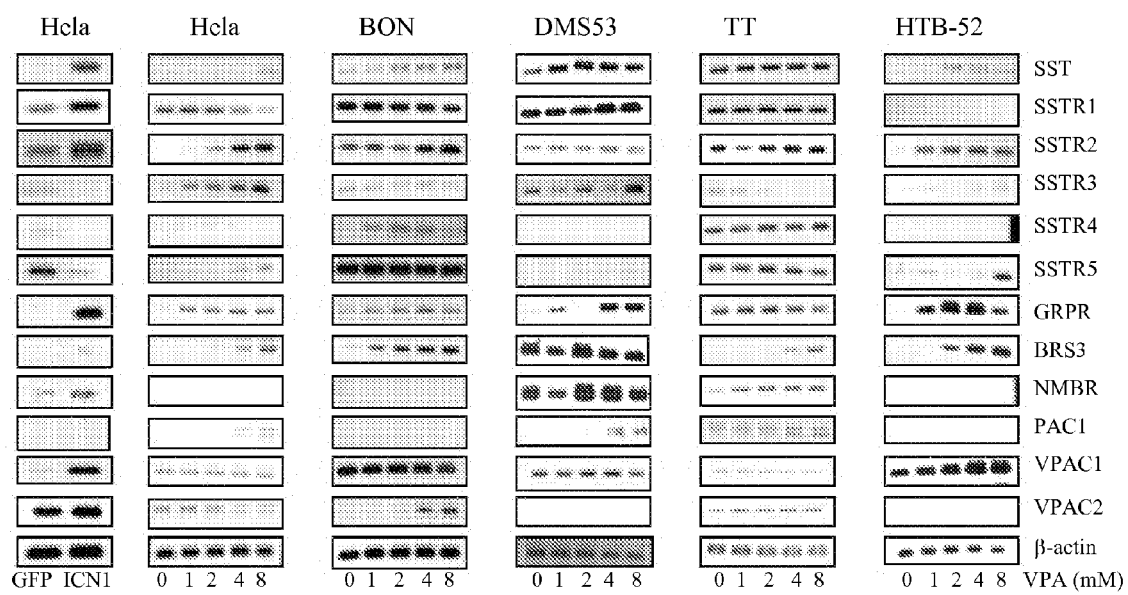
FIG. 55. RT-PCR detection of the VPA-mediated expression of certain GPCR members and somatostatin (SST) in cervical cancer Hela, pancreatic carcinoid BON, SCLC DMS-53, MTC TT, hepatoma HTB-52 cells and also in cervical cancer Hela-ICN1 cells with Notch1 activation. The tested GPCRs include SSTR1, SSTR2, SSTR3, SSTR4, SSTR5, GRPR, BRS3, NMBR, PAC1, VPAC1, and VPAC2.

First, we confirmed the increase in SSTR1 and SSTR2 in Hela-ICN1 cells using both RT-PCR and real-time PCR. We also found that the receptors GRPR, BRS3, NMBR, VPAC1, and VPAC2 were up-regulated in Hela-ICN1 cells, and that SSTR3, SSTR4, and SSTR5 were down-regulated (FIG. 55). VPA was further investigated for its effects on these receptors in the five tested cancer cells.

Cervical Cancer Hela Cells

With respect to VPA treatments, we found that SSTR2 (20-fold, confirmed by real-time PCR), SSTR3, SSTR5, PAC1, GRPR, and BRS3 were up-regulated and SSTR1 and VPAC2 were down-regulated, with no change of VPAC in Hela cells. The change of SSTR1, SSTR3, SSTR5, VPAC2, and VPAC1 are different between Hela-ICN1 and VPA-treated Hela cells (FIG. 55).

Pancreatic Carcinoid BON Cells

VPA induced the expression of SSTR2 (25-fold, confirmed by real-time PCR), SSTR4, BRS3, GRPR, and VPAC2 and suppressed SSTR1 in BON cells in a dose-dependent manner, with no change in the others (FIG. 55). SSTR5 is highly expressed in these cells but does not appear to change with VPA treatment. Real-time PCR further showed a slight decrease of SSTR5 (0.9-fold).

Small Cell Lung Cancer DMS-53 Cells

We investigated the expression of these receptors in VPA-treated DMS53 cells and found SSTR2 (5.4-fold, confirmed by real-time PCR), SSTR3, GRPR, and PAC1 increased, with no obvious change in SSTR1, SSTR2, VPAC1, NMBR, and BRS3, while SSTR4, SSTR5, PAC1 and VPAC2 were undetectable in native DMS-53 cells (FIG. 55).

Medullary Thyroid Cancer TT Cells

With VPA treatment, we found that SSTR2 (2.2-fold, confirmed by real-time PCR), BRS3, NMBR, and VPAC2 increased and SSTR3 and VPAC1 decreased, with no obvious change in the others (FIG. 55).

Hepatoma Cancer HTB-52 Cells

We found that VPA increased the expression of SSTR2 (19.8-fold, confirmed by real-time PCR), SSTR3, SSTR5, GRPR, BRS3, and VPAC1 in HTB-52 cancer cells. The other receptors are undetectable and not affected by VPA treatment (FIG. 55).

VPA Enhanced In Vivo Anti-Tumor Efficacy of the Conjugate

Our in vitro assay showed that VPA induced growth arrest in various tumor cells as described above and that VPA also up-regulates SSTR2's expression in many cancer cells. Our in vitro assay showed that a combination treatment of VPA with CPT-SST and VPA with COL-SST (FIG. 47), compared to each single agent alone, could significantly enhance the growth suppression in eleven tested cancer cells, such as Hela (FIG. 42), BON (FIG. 43), TT, HTB-52, DU-145, PC-3, OVCAR8, HT-29, CFPAC-1, SKOV3, and DMS-53 (data not shown). We also observed that VPA and CPT-BN conjugate enhanced anti-cell proliferation in treating BON cancer cells (FIG. 48), CNDT2 cancer cells (FIG. 49), and MOLT-4 cancer cells (FIG. 50), as measured using MTT proliferation assays.

A combination treatment with both VPA and COL-SST suppressed Hela tumor growth, better than did each alone. As shown in FIG. 42 and FIG. 43, the inhibitory rates from treatments with VPA at 200 mg/kg or COL-SST at 2 mg/kg are 36.7% and 72.9%, respectively. However, the inhibition from the combination therapy with low doses of VPA at 100 mg/kg and COL-SST at 1 mg/kg was 85.8% (FIG. 42 and FIG. 43). Similar results were observed in treating pancreatic carciniod BON tumors with VPA and COL-SST. The inhibitory rates from treatments of VPA at 200 mg/kg, COL-SST at 2 mg/kg and the combination of VPA at 100 mg/kg and COL-SST at 1 mg/kg are 47.9%, 31.6%, and 48.5%, respectively (FIG. 42 and FIG. 43). The results from both in vivo experiments suggest that VPA-mediated SSTR2 up-regulation could increase the uptake and anti-tumor efficacy of conjugate COL-SST.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

Detailed descriptions of one or more embodiments are provided herein. It is to be understood, however, that the present invention may be embodied in various forms. Therefore, specific details disclosed herein (even if designated as preferred or advantageous) are not to be interpreted as limiting, but rather are to be used as a basis for the claims and as a representative basis for teaching one skilled in the art to employ the present invention in any appropriate manner.

A number of embodiments have been described. Nevertheless it will be understood that various modifications may be made without departing from the spirit and scope of the invention. Accordingly, other embodiments are included as part of the invention and may be encompassed by the attached claims. Furthermore, the foregoing description of various embodiments does not necessarily imply exclusion. For example, "some" embodiments, "exemplary" embodiments, or "other" embodiments may include all or part of "some," "other," and "further" embodiments within the scope of this invention.

---

---

What is claimed is:

1. A method for treating cancer in an animal in need thereof comprising administering a multicomponent composition to the animal, wherein the multicomponent composition comprises a first component and a second component, where the first component is a composition comprising a notch influencing molecule and the second component is a composition comprising a GPCR targeted molecule, wherein the GPCR targeted molecule is selected from SST-14, an SST analog, or a molecule of Formula (I), $$X-Y-Z-Q \quad (I),$$

where X is

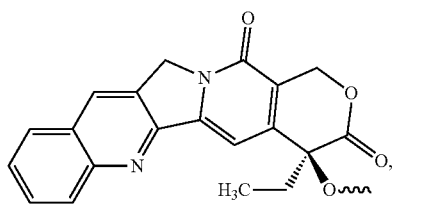

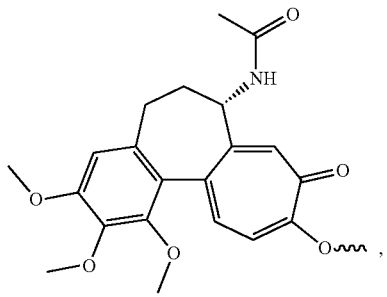

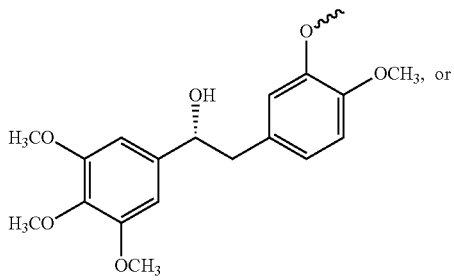

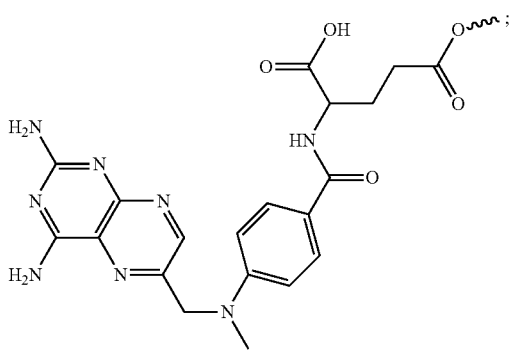

Y is a bond or

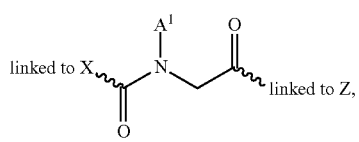

where $A^1$ is —$CH_2$—$CH_2$—$NH_2$, —$CH_2$—$CH_2$—NH—$CH_3$, —$CH_2$—$CH_2$—N—$(CH_3)_2$, —$CH_2$—$CH_2$—$CH_2$—$NH_2$, or —$CH_2$—$CH_2$—OH;

Z is a bond, {linked to Y}-NMeAmEtGly-Gaba-{linked to Q}, {linked to Y}-Gly-(Gaba)-{linked to Q}, {linked to Y}-(Gaba)-{linked to Q}, {linked to Y}-(D-Lys)-(D-Tyr)-Lys-(D-Tyr)-(D-Lys)-{linked to Q}, or {linked to Y}-(D-Ser)-(Nle)-(D-Tyr)-(D-Ser)-{linked to Q}; and Q is ∿∿Cys-Phe-(D-Trp)-Lys-Thr-Cys-Thr-$NH_2$,
    |                             |
    S————————S ∿∿(D-Phe)-Cys-Phe-(D-Trp)-Lys-Thr-Cys-Thr-$NH_2$,
           |                            |
           S————————S ∿∿(D-Ser)-(D-Lys)-Gln-Trp-Ala-Val-(β-Ala)-His-Phe-Nle-$NH_2$, ∿∿(D,-L-Ser)$_{14}$-(D-Ser)-(D-Lys)-Gln-Trp-Ala-Val-(β-Ala)-His-Phe-Nle-$NH_2$, ∿∿(D-Ser)-(D-Tyr)-Gln-Trp-Ala-Val(β-Ala)-His-Phe-Nle-$NH_2$, ∿∿Gly-(D-Ser)-(D-Tyr)-Gln-Trp-Ala-Val-(β-Ala)-His-Phe-Nle-$NH_2$, ∿∿Cys-Lys-Asn-Phe-Phe-(D-Trp)-Lys-Thr-Ser-Cys-$NH_2$,
    |                                   |
    S————————————S ∿∿Gaba-Cys-Lys-Asn-Phe-Phe-(D-Trp)-Lys-Thr-Phe-Thr-Ser-Cys-$NH_2$,
          |                                   |
          S————————————S ∿∿His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-$NH_2$, or ∿∿His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg-Val-Lys-Asn-Lys-$NH_2$.

2. The method of claim 1, wherein the notch influencing molecule is selected from the group consisting of a notch ligand, a notch receptor, a notch inhibitor, a carboxylate, VPA, trichostatin A, SBHA, a benzamide, an epoxyketone, a cyclic peptide, a hybrid molecule, a cyclostellettamine, and a carbamazepine.

3. The method of claim 1, wherein the notch influencing molecule is selected from the group consisting of VPA, SBHA, DBZ, and NLE.

4. The method of claim 1, wherein the GPCR targeted molecule is a molecule of Formula (I) or an SST analog.

5. The method of claim 1, wherein the GPCR targeted molecule is selected from the group consisting of COL-SST, CPT-SST, and CPT-BN.

6. The method of claim 1, wherein the notch influencing molecule is VPA and the GPCR targeted molecule is CPT-SST.

7. The method of claim 1, wherein the notch influencing molecule is VPA and the GPCR targeted molecule is COL-SST.

8. The method of claim 1, wherein the administering occurs orally, intranasally, or by injection.

9. The method of claim 1, wherein the administering occurs by intravenous injection, by intraperitoneal injection, by intramuscular injection, or by subcutaneous injection.

10. The method of claim 1, wherein the animal is a mammal.

11. The method of claim 1, wherein the animal is a human or a rodent.

12. The method of claim 1, wherein the cancer is selected from the group consisting of cervical cancer, pancreatic cancer, pancreatic carcinoid, lung cancer, small cell lung cancer (SCLC), skin cancer, medullary thyroid cancer (MTC), cutaneous squamous cell carcinoma, colonrectal cancer, osteosarcoma, hepatoma, leukemia, ovarian cancer, tumors, and endocrine tumors.

13. The method of claim 1, wherein the treating suppresses epithelial-mesenchymal transition in cancer cells.

* * * * *